United States Patent
Kostamo

(10) Patent No.: US 9,827,209 B2
(45) Date of Patent: Nov. 28, 2017

(54) DISPLAY SYSTEM

(71) Applicant: Microsoft Technology Licensing, LLC, Redmond, WA (US)

(72) Inventor: Pasi Kostamo, Espoo (FI)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 14/617,683

(22) Filed: Feb. 9, 2015

(65) Prior Publication Data
US 2016/0231478 A1    Aug. 11, 2016

(51) Int. Cl.
| | |
|---|---|
| G02B 5/18 | (2006.01) |
| G02B 6/34 | (2006.01) |
| G02B 27/01 | (2006.01) |
| G03F 7/20 | (2006.01) |
| A61K 31/047 | (2006.01) |
| A61K 31/70 | (2006.01) |
| A61K 51/04 | (2006.01) |
| G01N 33/60 | (2006.01) |

(Continued)

(52) U.S. Cl.
CPC ............ *A61K 31/047* (2013.01); *A61K 31/70* (2013.01); *A61K 45/06* (2013.01); *A61K 51/04* (2013.01); *A61K 51/0491* (2013.01); *G01N 33/60* (2013.01); *G01N 33/6896* (2013.01)

(58) Field of Classification Search
None
See application file for complete search history.

(56) References Cited

U.S. PATENT DOCUMENTS

| | | |
|---|---|---|
| 3,227,888 A | 1/1966 | Turnbull et al. |
| 3,410,774 A | 11/1968 | Barson et al. |
| 3,542,453 A | 11/1970 | Kantor |

(Continued)

FOREIGN PATENT DOCUMENTS

| | | |
|---|---|---|
| CN | 1440513 | 9/2003 |
| CN | 101029968 | 9/2007 |

(Continued)

OTHER PUBLICATIONS

Berger et al. "Photonic bandgaps and holography" J. appl. Phys., vol. 82(1) pp. 60-64 (Jul. 1997).*

(Continued)

*Primary Examiner* — Martin Angebranndt

(57) ABSTRACT

In making an optical component, one or more portions of a substrate's surface are patterned. At least a region of the substrate's surface is coated in negative photoresist, the region encompassing said portions. The negative photoresist becomes undevelopable when exposed to light. Light which forms a grating structure is projected over each of the portions. Light of substantially uniform intensity over the entirety of the region but for the portions, thereby leaving the negative photoresist outside of the portions undevelopable. The negative photoresist is developed so as to embody the grating structure in the photoresist covering the portions. The substrate's surface is patterned to impose the grating structure on the substrate's surface from the developed photoresist; the undevelopable photoresist inhibits patterning of the surface region outside of the portions. The optical component comprises the patterned substrate.

20 Claims, 19 Drawing Sheets

(51) Int. Cl.
*G01N 33/68* (2006.01)
*A61K 45/06* (2006.01)

(56) References Cited

U.S. PATENT DOCUMENTS

| | | | |
|---|---|---|---|
| 3,836,258 A | 9/1974 | Courten et al. | |
| 3,906,528 A | 9/1975 | Johnson | |
| 3,971,065 A | 7/1976 | Bayer | |
| 4,200,395 A | 4/1980 | Smith et al. | |
| 4,294,507 A | 10/1981 | Johnson | |
| 4,343,890 A * | 8/1982 | Phillips | G02B 5/1857 148/277 |
| 4,402,610 A | 9/1983 | Lacombat | |
| 4,560,249 A * | 12/1985 | Nishiwaki | G02B 5/32 359/3 |
| 4,664,524 A | 5/1987 | Hattori et al. | |
| 4,711,512 A | 12/1987 | Upatnieks | |
| 4,758,087 A | 7/1988 | Hicks, Jr. | |
| 4,799,752 A | 1/1989 | Carome | |
| 4,822,145 A | 4/1989 | Staelin | |
| 4,860,361 A | 8/1989 | Sato et al. | |
| 4,900,129 A | 2/1990 | Vanderwerf | |
| 4,957,351 A | 9/1990 | Shioji | |
| 5,004,673 A | 4/1991 | Vlannes | |
| 5,019,808 A | 5/1991 | Prince et al. | |
| 5,019,898 A | 5/1991 | Chao et al. | |
| 5,106,181 A | 4/1992 | Rockwell, III | |
| 5,114,236 A | 5/1992 | Matsugu et al. | |
| 5,146,355 A | 9/1992 | Prince et al. | |
| 5,162,656 A | 11/1992 | Matsugu et al. | |
| 5,216,257 A * | 6/1993 | Brueck | G03F 9/7049 250/237 G |
| 5,305,389 A | 4/1994 | Palmer | |
| 5,309,169 A | 5/1994 | Lippert | |
| 5,313,535 A | 5/1994 | Williams | |
| 5,359,444 A | 10/1994 | Piosenka et al. | |
| 5,413,884 A | 5/1995 | Koch et al. | |
| 5,453,877 A | 9/1995 | Gerbe et al. | |
| 5,455,458 A | 10/1995 | Quon et al. | |
| 5,459,611 A | 10/1995 | Bohn et al. | |
| 5,483,307 A | 1/1996 | Anderson | |
| 5,491,580 A | 2/1996 | O'Meara | |
| 5,543,588 A | 8/1996 | Bisset et al. | |
| 5,549,212 A | 8/1996 | Kanoh et al. | |
| 5,574,473 A | 11/1996 | Sekiguchi | |
| 5,579,830 A | 12/1996 | Giammaruti | |
| 5,583,609 A | 12/1996 | Mizutani et al. | |
| 5,606,455 A | 2/1997 | Eichenlaub | |
| 5,614,941 A | 3/1997 | Hines | |
| 5,630,902 A | 5/1997 | Galarneau et al. | |
| 5,648,643 A | 7/1997 | Knowles et al. | |
| 5,651,414 A | 7/1997 | Suzuki et al. | |
| 5,673,146 A | 9/1997 | Kelly | |
| 5,705,321 A * | 1/1998 | Brueck | B82Y 10/00 257/E21.027 |
| 5,708,449 A | 1/1998 | Heacock et al. | |
| 5,712,995 A | 1/1998 | Cohn | |
| 5,714,967 A | 2/1998 | Okamura et al. | |
| 5,737,171 A | 4/1998 | Buller et al. | |
| 5,751,476 A | 5/1998 | Matsui et al. | |
| 5,771,042 A | 6/1998 | Santos-Gomez | |
| 5,771,320 A | 6/1998 | Stone | |
| 5,772,903 A | 6/1998 | Hirsch | |
| 5,856,842 A | 1/1999 | Tedesco | |
| 5,861,931 A | 1/1999 | Gillian et al. | |
| 5,880,725 A | 3/1999 | Southgate | |
| 5,886,822 A | 3/1999 | Spitzer | |
| 5,940,149 A | 8/1999 | Vanderwerf | |
| 5,959,664 A | 9/1999 | Woodgate | |
| 5,982,553 A | 11/1999 | Bloom et al. | |
| 5,991,087 A | 11/1999 | Rallison | |
| 6,101,008 A | 8/2000 | Popovich | |
| 6,144,439 A | 11/2000 | Carollo | |
| 6,160,667 A | 12/2000 | Smoot | |
| 6,169,829 B1 | 1/2001 | Laming et al. | |
| 6,181,852 B1 | 1/2001 | Adams et al. | |
| 6,200,711 B1 | 3/2001 | Kurihara et al. | |
| 6,226,178 B1 | 5/2001 | Broder et al. | |
| 6,239,502 B1 | 5/2001 | Grewe et al. | |
| 6,264,787 B1 | 7/2001 | Burbank | |
| 6,271,808 B1 | 8/2001 | Corbin | |
| 6,307,142 B1 | 10/2001 | Allen et al. | |
| 6,323,949 B1 | 11/2001 | Lading et al. | |
| 6,323,970 B1 | 11/2001 | Popovich | |
| 6,377,401 B1 | 4/2002 | Bartlett | |
| 6,385,641 B1 | 5/2002 | Jiang | |
| 6,411,512 B1 | 6/2002 | Mankaruse et al. | |
| 6,417,892 B1 | 7/2002 | Sharp et al. | |
| 6,446,442 B1 | 9/2002 | Batchelor et al. | |
| 6,466,198 B1 | 10/2002 | Feinstein | |
| 6,470,289 B1 | 10/2002 | Peters et al. | |
| 6,481,851 B1 | 11/2002 | McNelley et al. | |
| 6,483,580 B1 | 11/2002 | Xu et al. | |
| 6,496,218 B2 | 12/2002 | Takigawa et al. | |
| 6,529,331 B2 | 3/2003 | Massof et al. | |
| 6,542,307 B2 | 4/2003 | Gleckman et al. | |
| 6,545,650 B1 | 4/2003 | Yamada et al. | |
| 6,553,165 B1 | 4/2003 | Temkin et al. | |
| 6,554,428 B2 | 4/2003 | Fergason et al. | |
| 6,577,411 B1 | 6/2003 | David | |
| 6,580,529 B1 | 6/2003 | Amitai et al. | |
| 6,606,152 B2 | 8/2003 | Littau | |
| 6,621,702 B2 | 9/2003 | Elias et al. | |
| 6,631,755 B1 | 10/2003 | Kung et al. | |
| 6,635,999 B2 | 10/2003 | Belliveau | |
| 6,639,201 B2 | 10/2003 | Almogy et al. | |
| 6,661,436 B2 | 12/2003 | Barksdale et al. | |
| 6,735,499 B2 | 5/2004 | Ohki et al. | |
| 6,753,828 B2 | 6/2004 | Tuceryan et al. | |
| 6,775,460 B2 | 8/2004 | Steiner et al. | |
| 6,792,328 B2 | 9/2004 | Laughery et al. | |
| 6,804,115 B2 | 10/2004 | Lai | |
| 6,809,925 B2 | 10/2004 | Belady et al. | |
| 6,819,426 B2 | 11/2004 | Sezginer et al. | |
| 6,825,987 B2 | 11/2004 | Repetto et al. | |
| 6,829,093 B1 | 12/2004 | Nakai | |
| 6,829,095 B2 | 12/2004 | Amitai | |
| 6,867,753 B2 | 3/2005 | Chinthammit et al. | |
| 6,877,134 B1 | 4/2005 | Fuller et al. | |
| 6,888,613 B2 | 5/2005 | Robins et al. | |
| 6,889,755 B2 | 5/2005 | Zuo et al. | |
| 6,898,596 B2 | 5/2005 | Aikens et al. | |
| 6,906,901 B1 | 6/2005 | Liu | |
| 6,916,584 B2 | 7/2005 | Sreenivasan et al. | |
| 6,919,867 B2 | 7/2005 | Sauer | |
| 6,947,020 B2 | 9/2005 | Kiser et al. | |
| 6,964,731 B1 | 11/2005 | Krisko et al. | |
| 6,971,443 B2 | 12/2005 | Kung et al. | |
| 6,974,714 B2 | 12/2005 | Uno | |
| 6,992,738 B2 | 1/2006 | Ishihara et al. | |
| 6,997,241 B2 | 2/2006 | Chou et al. | |
| 7,006,215 B2 | 2/2006 | Hoff et al. | |
| 7,015,876 B1 | 3/2006 | Miller | |
| 7,020,848 B2 | 3/2006 | Rosenzweig et al. | |
| 7,031,894 B2 | 4/2006 | Niu et al. | |
| 7,048,385 B2 | 5/2006 | Beeson et al. | |
| 7,061,624 B2 | 6/2006 | Ishizuka | |
| 7,069,975 B1 | 7/2006 | Haws et al. | |
| 7,072,049 B2 | 7/2006 | Niu et al. | |
| 7,099,005 B1 | 8/2006 | Fabrikant et al. | |
| 7,113,605 B2 | 9/2006 | Rui et al. | |
| 7,116,555 B2 | 10/2006 | Kamath et al. | |
| 7,151,635 B2 | 12/2006 | Bidnyk et al. | |
| 7,159,174 B2 | 1/2007 | Johnson et al. | |
| 7,181,699 B2 | 2/2007 | Morrow et al. | |
| 7,184,615 B2 | 2/2007 | Levola | |
| 7,189,362 B2 | 3/2007 | Nordin et al. | |
| 7,191,820 B2 | 3/2007 | Chou et al. | |
| 7,193,584 B2 | 3/2007 | Lee et al. | |
| 7,196,758 B2 | 3/2007 | Crawford et al. | |
| 7,206,107 B2 | 4/2007 | Levola | |
| 7,212,709 B2 | 5/2007 | Hosoi | |
| 7,212,723 B2 | 5/2007 | McLeod et al. | |
| 7,250,930 B2 | 7/2007 | Hoffman et al. | |

(56) References Cited

U.S. PATENT DOCUMENTS

| | | |
|---|---|---|
| 7,253,445 B2 | 8/2007 | Heremans et al. |
| 7,261,453 B2 | 8/2007 | Morejon et al. |
| 7,261,827 B2 | 8/2007 | Ootsu et al. |
| 7,271,795 B2 | 9/2007 | Bradski |
| 7,277,282 B2 | 10/2007 | Tate |
| 7,301,587 B2 | 11/2007 | Uehara et al. |
| 7,324,754 B2 | 1/2008 | Kobayashi et al. |
| 7,333,690 B1 | 2/2008 | Peale et al. |
| 7,337,018 B2 | 2/2008 | Espinoza-Ibarra et al. |
| 7,359,420 B2 | 4/2008 | Shchegrov et al. |
| 7,365,734 B2 | 4/2008 | Fateh et al. |
| 7,369,101 B2 | 5/2008 | Sauer et al. |
| 7,372,565 B1 | 5/2008 | Holden et al. |
| 7,376,852 B2 | 5/2008 | Edwards |
| 7,396,133 B2 | 7/2008 | Burnett et al. |
| 7,399,420 B2 * | 7/2008 | Paek .................. B29C 59/022 216/24 |
| 7,412,306 B2 | 8/2008 | Katoh et al. |
| 7,416,017 B2 | 8/2008 | Haws et al. |
| 7,417,617 B2 | 8/2008 | Eichenlaub |
| 7,418,170 B2 | 8/2008 | Mukawa et al. |
| 7,428,001 B2 | 9/2008 | Schowengerdt et al. |
| 7,430,349 B2 | 9/2008 | Jones |
| 7,430,355 B2 | 9/2008 | Heikenfeld et al. |
| 7,437,678 B2 | 10/2008 | Awada et al. |
| 7,455,102 B2 | 11/2008 | Cheng |
| 7,496,642 B2 | 2/2009 | Gill et al. |
| 7,505,269 B1 | 3/2009 | Cosley et al. |
| 7,513,627 B2 | 4/2009 | Larson et al. |
| 7,515,143 B2 | 4/2009 | Keam et al. |
| 7,515,279 B2 | 4/2009 | Raymond |
| 7,518,740 B2 | 4/2009 | Chard et al. |
| 7,532,227 B2 | 5/2009 | Nakajima et al. |
| 7,539,371 B2 | 5/2009 | Martinelli et al. |
| 7,542,665 B2 | 6/2009 | Lei |
| 7,551,814 B1 | 6/2009 | Smits |
| 7,576,916 B2 | 8/2009 | Amitai |
| 7,583,327 B2 | 9/2009 | Takatani |
| 7,587,419 B2 | 9/2009 | Thorpe et al. |
| 7,607,111 B2 | 10/2009 | Vaananen et al. |
| 7,612,882 B2 | 11/2009 | Wu et al. |
| 7,619,895 B1 | 11/2009 | Wertz et al. |
| 7,631,687 B2 | 12/2009 | Yang |
| 7,634,478 B2 | 12/2009 | Yang et al. |
| 7,646,606 B2 | 1/2010 | Rytka et al. |
| 7,646,950 B2 | 1/2010 | Park et al. |
| 7,649,594 B2 | 1/2010 | Kim et al. |
| 7,656,912 B2 | 2/2010 | Brueck et al. |
| 7,660,500 B2 | 2/2010 | Konttinen et al. |
| 7,668,842 B2 | 2/2010 | LaChapelle et al. |
| 7,679,641 B2 | 3/2010 | Lipton et al. |
| 7,693,292 B1 | 4/2010 | Gross et al. |
| 7,693,911 B2 | 4/2010 | Wories et al. |
| 7,701,716 B2 | 4/2010 | Blanco, Jr. et al. |
| 7,706,785 B2 | 4/2010 | Lei et al. |
| 7,716,003 B1 | 5/2010 | Wack et al. |
| 7,716,317 B2 | 5/2010 | Kumar et al. |
| 7,719,769 B2 | 5/2010 | Sugihara et al. |
| 7,728,933 B2 | 6/2010 | Kim et al. |
| 7,730,113 B1 | 6/2010 | Payette et al. |
| 7,764,413 B2 | 7/2010 | Levola |
| 7,768,534 B2 | 8/2010 | Pentenrieder et al. |
| 7,777,944 B2 | 8/2010 | Ho et al. |
| 7,783,669 B2 | 8/2010 | Qiu et al. |
| 7,788,474 B2 | 8/2010 | Switzer et al. |
| 7,817,104 B2 | 10/2010 | Ryu et al. |
| 7,826,508 B2 | 11/2010 | Reid et al. |
| 7,832,885 B2 | 11/2010 | Hsiao et al. |
| 7,843,691 B2 | 11/2010 | Reichert et al. |
| 7,871,811 B2 | 1/2011 | Fang et al. |
| 7,882,115 B2 | 2/2011 | Hirsch |
| 7,890,882 B1 | 2/2011 | Nelson |
| 7,894,613 B1 | 2/2011 | Ong et al. |
| 7,903,409 B2 | 3/2011 | Patel et al. |
| 7,904,832 B2 | 3/2011 | Ubillos |
| 7,908,273 B2 | 3/2011 | DiMaria et al. |
| 7,909,958 B2 | 3/2011 | Washburn et al. |
| 7,941,231 B1 | 5/2011 | Dunn |
| 7,949,214 B2 | 5/2011 | DeJong |
| 7,966,184 B2 | 6/2011 | O'Conor et al. |
| 7,986,462 B2 | 7/2011 | Kobayashi et al. |
| 8,004,621 B2 | 8/2011 | Woodgate et al. |
| 8,014,644 B2 | 9/2011 | Morimoto et al. |
| 8,033,709 B2 | 10/2011 | Kao et al. |
| 8,035,896 B2 | 10/2011 | Taira et al. |
| 8,046,616 B2 | 10/2011 | Edwards |
| 8,061,411 B2 | 11/2011 | Xu et al. |
| 8,085,948 B2 | 12/2011 | Thomas et al. |
| 8,092,064 B2 | 1/2012 | Erchak et al. |
| 8,108,430 B2 | 1/2012 | Wong et al. |
| 8,125,579 B2 | 2/2012 | Khan et al. |
| 8,128,800 B2 | 3/2012 | Seo et al. |
| 8,139,504 B2 | 3/2012 | Mankins et al. |
| 8,150,893 B2 | 4/2012 | Bohannon et al. |
| 8,160,411 B2 | 4/2012 | Levola et al. |
| 8,162,524 B2 | 4/2012 | Van Ostrand et al. |
| 8,165,988 B2 | 4/2012 | Shau et al. |
| 8,176,436 B2 | 5/2012 | Arend et al. |
| 8,189,263 B1 | 5/2012 | Wang et al. |
| 8,195,220 B2 | 6/2012 | Kim et al. |
| 8,200,704 B2 | 6/2012 | Petakov et al. |
| 8,233,204 B1 | 7/2012 | Robbins et al. |
| 8,233,273 B2 | 7/2012 | Chen et al. |
| 8,244,667 B1 | 8/2012 | Weinberger et al. |
| 8,246,170 B2 | 8/2012 | Yamamoto et al. |
| 8,274,614 B2 | 9/2012 | Yokote et al. |
| 8,280,861 B1 | 10/2012 | Park et al. |
| 8,291,349 B1 | 10/2012 | Park et al. |
| 8,300,614 B2 | 10/2012 | Ankaiah et al. |
| 8,320,032 B2 | 11/2012 | Levola |
| 8,332,402 B2 | 12/2012 | Forstall et al. |
| 8,358,400 B2 | 1/2013 | Escuti |
| 8,384,999 B1 | 2/2013 | Crosby et al. |
| 8,392,035 B2 | 3/2013 | Patel et al. |
| 8,395,898 B1 | 3/2013 | Chamseddine et al. |
| 8,418,083 B1 | 4/2013 | Lundy et al. |
| 8,434,019 B2 | 4/2013 | Nelson |
| 8,446,340 B2 | 5/2013 | Aharoni |
| 8,466,953 B2 | 6/2013 | Levola |
| 8,472,119 B1 | 6/2013 | Kelly |
| 8,482,920 B2 | 7/2013 | Tissot et al. |
| 8,571,539 B1 | 10/2013 | Ranganathan et al. |
| 8,576,143 B1 | 11/2013 | Kelly |
| 8,589,341 B2 | 11/2013 | Golde et al. |
| 8,593,734 B2 | 11/2013 | Laakkonen |
| 8,594,702 B2 | 11/2013 | Naaman et al. |
| 8,605,700 B2 | 12/2013 | Gurin |
| 8,611,014 B2 | 12/2013 | Valera et al. |
| 8,627,228 B2 | 1/2014 | Yosef et al. |
| 8,629,815 B2 | 1/2014 | Brin et al. |
| 8,634,139 B1 | 1/2014 | Brown et al. |
| 8,638,498 B2 | 1/2014 | Bohn et al. |
| 8,645,871 B2 | 2/2014 | Fong et al. |
| 8,666,212 B1 | 3/2014 | Amirparviz |
| 8,693,500 B2 | 4/2014 | Ludwig et al. |
| 8,698,845 B2 | 4/2014 | Lemay |
| 8,700,931 B2 | 4/2014 | Gudlavenkatasiva et al. |
| 8,712,598 B2 | 4/2014 | Dighde et al. |
| 8,717,676 B2 | 5/2014 | Rinko |
| 8,745,513 B2 | 6/2014 | Crystal |
| 8,754,831 B2 | 6/2014 | Kollin et al. |
| 8,793,282 B2 | 7/2014 | Hedinsson et al. |
| 8,796,012 B2 | 8/2014 | Sinclair et al. |
| 8,810,600 B2 | 8/2014 | Bohn et al. |
| 8,817,350 B1 | 8/2014 | Robbins et al. |
| 8,819,079 B2 | 8/2014 | Bush et al. |
| 8,823,531 B1 | 9/2014 | McCleary et al. |
| 8,843,744 B2 | 9/2014 | Sentinelli et al. |
| 8,885,997 B2 | 11/2014 | Nguyen et al. |
| 8,909,384 B1 | 12/2014 | Beitelmal et al. |
| 8,917,453 B2 | 12/2014 | Bohn |
| 8,934,235 B2 | 1/2015 | Rubenstein et al. |
| 8,941,683 B2 | 1/2015 | Son et al. |
| 8,989,535 B2 | 3/2015 | Robbins |

(56) References Cited

U.S. PATENT DOCUMENTS

| | | |
|---|---|---|
| 8,990,255 B2 | 3/2015 | Metsatahti et al. |
| 9,003,162 B2 | 4/2015 | Lomet et al. |
| 9,304,235 B2 | 4/2016 | Sainiemi et al. |
| 9,372,347 B1 * | 6/2016 | Levola ............... G02B 27/0172 |
| 9,423,360 B1 | 8/2016 | Kostamo et al. |
| 9,429,692 B1 | 8/2016 | Saarikko et al. |
| 9,513,480 B2 | 12/2016 | Saarikko et al. |
| 9,514,211 B2 | 12/2016 | Sengupta et al. |
| 9,535,253 B2 | 1/2017 | Levola et al. |
| 2001/0043208 A1 | 11/2001 | Furness, III et al. |
| 2002/0035455 A1 | 3/2002 | Niu et al. |
| 2002/0038196 A1 | 3/2002 | Johnson et al. |
| 2002/0041735 A1 | 4/2002 | Cai et al. |
| 2002/0044152 A1 | 4/2002 | Abbott et al. |
| 2002/0044162 A1 | 4/2002 | Sawatari |
| 2002/0063820 A1 | 5/2002 | Broer et al. |
| 2002/0097558 A1 | 7/2002 | Stone et al. |
| 2002/0138772 A1 | 9/2002 | Crawford et al. |
| 2002/0171939 A1 | 11/2002 | Song |
| 2002/0180659 A1 | 12/2002 | Takahashi |
| 2003/0006364 A1 | 1/2003 | Katzir et al. |
| 2003/0023889 A1 | 1/2003 | Hofstee et al. |
| 2003/0137706 A1 | 7/2003 | Rmanujam et al. |
| 2003/0179543 A1 | 9/2003 | Mori et al. |
| 2003/0204698 A1 | 10/2003 | Sachedina et al. |
| 2003/0214728 A1 | 11/2003 | Olczak |
| 2004/0011503 A1 | 1/2004 | Kung et al. |
| 2004/0024580 A1 | 2/2004 | Salmonsen et al. |
| 2004/0042724 A1 | 3/2004 | Gombert et al. |
| 2004/0085649 A1 | 5/2004 | Repetto et al. |
| 2004/0108971 A1 | 6/2004 | Waldern et al. |
| 2004/0109234 A1 | 6/2004 | Levola |
| 2004/0135209 A1 | 7/2004 | Hsieh et al. |
| 2004/0139169 A1 | 7/2004 | O'Brien et al. |
| 2004/0151466 A1 | 8/2004 | Crossman-Bosworth et al. |
| 2004/0176928 A1 | 9/2004 | Johnson |
| 2004/0267990 A1 | 12/2004 | Lin |
| 2005/0089328 A1 | 4/2005 | Nishiki et al. |
| 2005/0100272 A1 | 5/2005 | Gilman |
| 2005/0174737 A1 | 8/2005 | Meir |
| 2005/0207120 A1 | 9/2005 | Tseng et al. |
| 2005/0243107 A1 | 11/2005 | Haim et al. |
| 2005/0246352 A1 | 11/2005 | Moore et al. |
| 2005/0248705 A1 | 11/2005 | Smith et al. |
| 2005/0285878 A1 | 12/2005 | Singh et al. |
| 2006/0018025 A1 | 1/2006 | Sharon et al. |
| 2006/0032616 A1 | 2/2006 | Yang |
| 2006/0038881 A1 | 2/2006 | Starkweather et al. |
| 2006/0054787 A1 | 3/2006 | Olsen et al. |
| 2006/0072206 A1 | 4/2006 | Tsuyuki et al. |
| 2006/0080401 A1 | 4/2006 | Gill et al. |
| 2006/0118280 A1 | 6/2006 | Liu |
| 2006/0126181 A1 | 6/2006 | Levola |
| 2006/0129951 A1 | 6/2006 | Vaananen et al. |
| 2006/0132806 A1 | 6/2006 | Shchegrov et al. |
| 2006/0132914 A1 | 6/2006 | Weiss et al. |
| 2006/0139447 A1 | 6/2006 | Unkrich |
| 2006/0152646 A1 | 7/2006 | Schrader |
| 2006/0155723 A1 | 7/2006 | Kumar et al. |
| 2006/0164382 A1 | 7/2006 | Kulas et al. |
| 2006/0183331 A1 | 8/2006 | Hofmann |
| 2006/0196643 A1 | 9/2006 | Hata et al. |
| 2006/0215244 A1 | 9/2006 | Yosha et al. |
| 2006/0221448 A1 | 10/2006 | Nivon et al. |
| 2006/0228073 A1 | 10/2006 | Mukawa et al. |
| 2006/0249765 A1 | 11/2006 | Hsieh |
| 2006/0250541 A1 | 11/2006 | Huck |
| 2007/0002412 A1 | 1/2007 | Aihara |
| 2007/0005334 A1 | 1/2007 | Salmonsen |
| 2007/0008456 A1 | 1/2007 | Lesage et al. |
| 2007/0023703 A1 | 2/2007 | Sunaoshi et al. |
| 2007/0027591 A1 | 2/2007 | Goldenberg et al. |
| 2007/0041684 A1 | 2/2007 | Popovich et al. |
| 2007/0097019 A1 | 5/2007 | Wynne-Powell et al. |
| 2007/0147673 A1 | 6/2007 | Crandall |
| 2007/0153395 A1 | 7/2007 | Repetto et al. |
| 2007/0171328 A1 | 7/2007 | Freeman et al. |
| 2007/0177260 A1 | 8/2007 | Kuppenheimer et al. |
| 2007/0208687 A1 | 9/2007 | O'Conor et al. |
| 2007/0214180 A1 | 9/2007 | Crawford |
| 2007/0236959 A1 | 10/2007 | Tolbert |
| 2007/0284093 A1 | 12/2007 | Bhatti et al. |
| 2007/0288478 A1 | 12/2007 | DiMaria et al. |
| 2008/0005348 A1 | 1/2008 | Kosiba et al. |
| 2008/0008076 A1 | 1/2008 | Raguin et al. |
| 2008/0014534 A1 | 1/2008 | Barwicz et al. |
| 2008/0025350 A1 | 1/2008 | Arbore et al. |
| 2008/0043100 A1 | 2/2008 | Sobel et al. |
| 2008/0043425 A1 | 2/2008 | Hebert et al. |
| 2008/0059535 A1 | 3/2008 | Lindsley et al. |
| 2008/0088603 A1 | 4/2008 | Eliasson et al. |
| 2008/0088624 A1 | 4/2008 | Long et al. |
| 2008/0106677 A1 | 5/2008 | Kuan et al. |
| 2008/0117341 A1 | 5/2008 | McGrew |
| 2008/0141681 A1 | 6/2008 | Arnold |
| 2008/0150913 A1 | 6/2008 | Bell et al. |
| 2008/0174735 A1 | 7/2008 | Quach et al. |
| 2008/0189303 A1 | 8/2008 | Bush et al. |
| 2008/0232680 A1 | 9/2008 | Berestov et al. |
| 2008/0248852 A1 | 10/2008 | Rasmussen |
| 2008/0285140 A1 | 11/2008 | Amitai |
| 2008/0297535 A1 | 12/2008 | Reinig |
| 2008/0303918 A1 | 12/2008 | Keithley |
| 2008/0311386 A1 | 12/2008 | Wendt |
| 2009/0002939 A1 | 1/2009 | Baugh et al. |
| 2009/0015742 A1 | 1/2009 | Liao et al. |
| 2009/0021908 A1 | 1/2009 | Patel et al. |
| 2009/0051283 A1 | 2/2009 | Cok et al. |
| 2009/0059376 A1 | 3/2009 | Hayakawa |
| 2009/0084525 A1 | 4/2009 | Satou et al. |
| 2009/0084757 A1 | 4/2009 | Erokhin et al. |
| 2009/0092261 A1 | 4/2009 | Bard |
| 2009/0097127 A1 | 4/2009 | Amitai |
| 2009/0113301 A1 | 4/2009 | Fisher et al. |
| 2009/0128449 A1 | 5/2009 | Brown et al. |
| 2009/0128901 A1 | 5/2009 | Tilleman et al. |
| 2009/0144642 A1 | 6/2009 | Crystal |
| 2009/0180250 A1 | 7/2009 | Holling et al. |
| 2009/0188610 A1 | 7/2009 | Yamamoto |
| 2009/0189974 A1 | 7/2009 | Deering |
| 2009/0190003 A1 | 7/2009 | Park et al. |
| 2009/0193024 A1 | 7/2009 | Dhananjaya |
| 2009/0195756 A1 | 8/2009 | Li et al. |
| 2009/0199128 A1 | 8/2009 | Matthews et al. |
| 2009/0222147 A1 | 9/2009 | Nakashima et al. |
| 2009/0224416 A1 | 9/2009 | Laakkonen et al. |
| 2009/0235203 A1 | 9/2009 | Iizuka |
| 2009/0244413 A1 | 10/2009 | Ishikawa et al. |
| 2009/0246707 A1 | 10/2009 | Li et al. |
| 2009/0256837 A1 | 10/2009 | Deb et al. |
| 2009/0262419 A1 | 10/2009 | Robinson et al. |
| 2009/0303599 A1 | 12/2009 | Levola |
| 2010/0002989 A1 | 1/2010 | Tokushima |
| 2010/0018858 A1 | 1/2010 | Seki |
| 2010/0021108 A1 | 1/2010 | Kang et al. |
| 2010/0053151 A1 | 3/2010 | Marti et al. |
| 2010/0060551 A1 | 3/2010 | Sugiyama et al. |
| 2010/0061078 A1 | 3/2010 | Kim |
| 2010/0074291 A1 | 3/2010 | Nakamura |
| 2010/0079865 A1 | 4/2010 | Saarikko et al. |
| 2010/0084674 A1 | 4/2010 | Paetzold et al. |
| 2010/0096617 A1 | 4/2010 | Shanks |
| 2010/0103078 A1 | 4/2010 | Mukawa et al. |
| 2010/0134534 A1 | 6/2010 | Seesselberg et al. |
| 2010/0138809 A1 | 6/2010 | Shenfield et al. |
| 2010/0141905 A1 | 6/2010 | Burke |
| 2010/0149073 A1 | 6/2010 | Chaum et al. |
| 2010/0188353 A1 | 7/2010 | Yoon et al. |
| 2010/0191783 A1 | 7/2010 | Mason |
| 2010/0200736 A1 | 8/2010 | Laycock et al. |
| 2010/0201953 A1 | 8/2010 | Freeman et al. |
| 2010/0202725 A1 | 8/2010 | Popovich et al. |
| 2010/0205178 A1 | 8/2010 | Bush et al. |
| 2010/0211575 A1 | 8/2010 | Collins et al. |

(56) References Cited

U.S. PATENT DOCUMENTS

| | | |
|---|---|---|
| 2010/0213467 A1 | 8/2010 | Lee et al. |
| 2010/0220439 A1 | 9/2010 | Qin |
| 2010/0229853 A1 | 9/2010 | Vandal et al. |
| 2010/0238270 A1 | 9/2010 | Bjelkhagen et al. |
| 2010/0245387 A1 | 9/2010 | Bachelder et al. |
| 2010/0259889 A1 | 10/2010 | Chen et al. |
| 2010/0271467 A1 | 10/2010 | Akeley |
| 2010/0277421 A1 | 11/2010 | Charlier et al. |
| 2010/0277439 A1 | 11/2010 | Charlier et al. |
| 2010/0277779 A1 | 11/2010 | Futterer et al. |
| 2010/0277803 A1 | 11/2010 | Pockett et al. |
| 2010/0278484 A1 | 11/2010 | Scheerlinck et al. |
| 2010/0281382 A1 | 11/2010 | Meaney et al. |
| 2010/0284085 A1 | 11/2010 | Laakkonen |
| 2010/0300654 A1 | 12/2010 | Edwards |
| 2010/0309687 A1 | 12/2010 | Sampsell et al. |
| 2010/0315781 A1 | 12/2010 | Agostini |
| 2010/0317132 A1 | 12/2010 | Rogers et al. |
| 2010/0321609 A1 | 12/2010 | Qi et al. |
| 2010/0321781 A1 | 12/2010 | Levola |
| 2010/0328351 A1 | 12/2010 | Tan |
| 2011/0012814 A1 | 1/2011 | Tanaka |
| 2011/0021251 A1 | 1/2011 | Lindén |
| 2011/0025605 A1 | 2/2011 | Kwitek |
| 2011/0026128 A1 | 2/2011 | Baker et al. |
| 2011/0032482 A1 | 2/2011 | Agurok |
| 2011/0038049 A1 | 2/2011 | Vallius et al. |
| 2011/0050547 A1 | 3/2011 | Mukawa |
| 2011/0050655 A1 | 3/2011 | Mukawa |
| 2011/0055765 A1 | 3/2011 | Neubrand et al. |
| 2011/0063795 A1 | 3/2011 | Yeh et al. |
| 2011/0075442 A1 | 3/2011 | Chiang |
| 2011/0084893 A1 | 4/2011 | Lee et al. |
| 2011/0090343 A1 | 4/2011 | Alt et al. |
| 2011/0091156 A1 | 4/2011 | Laughlin |
| 2011/0096401 A1 | 4/2011 | Levola |
| 2011/0099512 A1 | 4/2011 | Jeong |
| 2011/0114823 A1 | 5/2011 | Katzir et al. |
| 2011/0115340 A1 | 5/2011 | Lee |
| 2011/0127024 A1 | 6/2011 | Patel et al. |
| 2011/0134017 A1 | 6/2011 | Burke |
| 2011/0134645 A1 | 6/2011 | Hitchcock et al. |
| 2011/0141388 A1 | 6/2011 | Park et al. |
| 2011/0148931 A1 | 6/2011 | Kim |
| 2011/0163986 A1 | 7/2011 | Lee et al. |
| 2011/0175930 A1 | 7/2011 | Hwang et al. |
| 2011/0194029 A1 | 8/2011 | Herrmann et al. |
| 2011/0205251 A1 | 8/2011 | Auld |
| 2011/0210946 A1 | 9/2011 | Goertz et al. |
| 2011/0214082 A1 | 9/2011 | Osterhout et al. |
| 2011/0215349 A1 | 9/2011 | An et al. |
| 2011/0221658 A1 | 9/2011 | Haddick et al. |
| 2011/0221659 A1 | 9/2011 | King et al. |
| 2011/0222236 A1 | 9/2011 | Luo et al. |
| 2011/0227820 A1 | 9/2011 | Haddick et al. |
| 2011/0227913 A1 | 9/2011 | Hyndman |
| 2011/0231192 A1 | 9/2011 | O'Conor et al. |
| 2011/0235179 A1 | 9/2011 | Simmonds |
| 2011/0242145 A1 | 10/2011 | Nishimura et al. |
| 2011/0242392 A1 | 10/2011 | Chiang |
| 2011/0242670 A1 | 10/2011 | Simmonds |
| 2011/0242757 A1 | 10/2011 | Tracy et al. |
| 2011/0248904 A1 | 10/2011 | Miyawaki et al. |
| 2011/0248958 A1 | 10/2011 | Gruhlke et al. |
| 2011/0267799 A1 | 11/2011 | Epstein et al. |
| 2011/0283223 A1 | 11/2011 | Vaittinen et al. |
| 2011/0295913 A1 | 12/2011 | Enbutsu |
| 2011/0299044 A1 | 12/2011 | Yeh et al. |
| 2011/0304640 A1 | 12/2011 | Noge |
| 2011/0309378 A1 | 12/2011 | Lau et al. |
| 2011/0310232 A1 | 12/2011 | Wilson et al. |
| 2011/0310312 A1 | 12/2011 | Yokote et al. |
| 2012/0013651 A1 | 1/2012 | Trayner et al. |
| 2012/0019434 A1 | 1/2012 | Kuhlman et al. |
| 2012/0026161 A1 | 2/2012 | Chen et al. |
| 2012/0030616 A1 | 2/2012 | Howes et al. |
| 2012/0033306 A1 | 2/2012 | Valera et al. |
| 2012/0038629 A1 | 2/2012 | Brown et al. |
| 2012/0041721 A1 | 2/2012 | Chen |
| 2012/0044573 A1 | 2/2012 | Simmonds et al. |
| 2012/0050144 A1 | 3/2012 | Morlock |
| 2012/0052934 A1 | 3/2012 | Maharbiz et al. |
| 2012/0062998 A1 | 3/2012 | Schultz et al. |
| 2012/0069413 A1 | 3/2012 | Schultz |
| 2012/0084710 A1 | 4/2012 | Sirpal et al. |
| 2012/0105487 A1 | 5/2012 | Son et al. |
| 2012/0106170 A1 | 5/2012 | Matthews et al. |
| 2012/0111544 A1 | 5/2012 | Senatori |
| 2012/0113092 A1 | 5/2012 | Bar-Zeev et al. |
| 2012/0120493 A1 | 5/2012 | Simmonds et al. |
| 2012/0127577 A1 | 5/2012 | Desserouer |
| 2012/0134623 A1 | 5/2012 | Boudreau et al. |
| 2012/0144331 A1 | 6/2012 | Tolonen et al. |
| 2012/0157114 A1 | 6/2012 | Alameh et al. |
| 2012/0162764 A1 | 6/2012 | Shimizu |
| 2012/0176322 A1 | 7/2012 | Karmi et al. |
| 2012/0176474 A1 | 7/2012 | Border |
| 2012/0182687 A1 | 7/2012 | Dighde et al. |
| 2012/0188205 A1 | 7/2012 | Jansson et al. |
| 2012/0195553 A1 | 8/2012 | Hasegawa et al. |
| 2012/0200495 A1 | 8/2012 | Johansson |
| 2012/0206589 A1 | 8/2012 | Crandall |
| 2012/0206880 A1 | 8/2012 | Andres et al. |
| 2012/0218301 A1 | 8/2012 | Miller |
| 2012/0227006 A1 | 9/2012 | Amm |
| 2012/0235885 A1 | 9/2012 | Miller et al. |
| 2012/0242561 A1 | 9/2012 | Sugihara |
| 2012/0256856 A1 | 10/2012 | Suzuki et al. |
| 2012/0256963 A1 | 10/2012 | Suzuki et al. |
| 2012/0262657 A1 | 10/2012 | Nakanishi et al. |
| 2012/0287381 A1 | 11/2012 | Li et al. |
| 2012/0292535 A1 | 11/2012 | Choi et al. |
| 2012/0304092 A1 | 11/2012 | Jarrett et al. |
| 2012/0311481 A1 | 12/2012 | Reyna |
| 2013/0000871 A1 | 1/2013 | Olson et al. |
| 2013/0019273 A1 | 1/2013 | Ma et al. |
| 2013/0033485 A1 | 2/2013 | Kollin et al. |
| 2013/0081779 A1 | 4/2013 | Liao et al. |
| 2013/0093741 A1 | 4/2013 | Akimoto et al. |
| 2013/0106674 A1 | 5/2013 | Wheeler et al. |
| 2013/0148864 A1 | 6/2013 | Dolson et al. |
| 2013/0158957 A1 | 6/2013 | Lee et al. |
| 2013/0162673 A1 | 6/2013 | Bohn |
| 2013/0163089 A1 | 6/2013 | Bohn |
| 2013/0170031 A1 | 7/2013 | Bohn |
| 2013/0170802 A1 | 7/2013 | Pitwon |
| 2013/0186596 A1 | 7/2013 | Rubenstein |
| 2013/0186598 A1 | 7/2013 | Rubenstein |
| 2013/0187943 A1 | 7/2013 | Bohn et al. |
| 2013/0198176 A1 | 8/2013 | Kim |
| 2013/0207964 A1 | 8/2013 | Fleck |
| 2013/0208003 A1 | 8/2013 | Bohn |
| 2013/0208362 A1 | 8/2013 | Bohn |
| 2013/0208482 A1 | 8/2013 | Fleck |
| 2013/0215081 A1 | 8/2013 | Levin et al. |
| 2013/0226931 A1 | 8/2013 | Hazel et al. |
| 2013/0242056 A1 | 9/2013 | Fleck |
| 2013/0242555 A1 | 9/2013 | Mukawa |
| 2013/0250431 A1 | 9/2013 | Robbins et al. |
| 2013/0252628 A1 | 9/2013 | Kuehnel |
| 2013/0254412 A1 | 9/2013 | Menezes et al. |
| 2013/0257848 A1 | 10/2013 | Westerinen et al. |
| 2013/0258701 A1 | 10/2013 | Westerinen et al. |
| 2013/0267309 A1 | 10/2013 | Robbins |
| 2013/0294030 A1 | 11/2013 | Wang et al. |
| 2013/0305184 A1 | 11/2013 | Kim et al. |
| 2013/0307875 A1 | 11/2013 | Anderson |
| 2013/0314789 A1 | 11/2013 | Saarikko et al. |
| 2013/0314793 A1 | 11/2013 | Robbins |
| 2013/0322810 A1 | 12/2013 | Robbins |
| 2013/0332159 A1 | 12/2013 | Federighi et al. |
| 2013/0335671 A1 | 12/2013 | Fleck |
| 2013/0339446 A1 | 12/2013 | Balassanian et al. |
| 2013/0342674 A1 | 12/2013 | Dixon |

(56) References Cited

U.S. PATENT DOCUMENTS

| | | |
|---|---|---|
| 2013/0346725 A1 | 12/2013 | Lomet et al. |
| 2014/0010265 A1 | 1/2014 | Peng |
| 2014/0022265 A1 | 1/2014 | Canan |
| 2014/0041827 A1 | 2/2014 | Giaimo |
| 2014/0059139 A1 | 2/2014 | Filev et al. |
| 2014/0063367 A1 | 3/2014 | Yang et al. |
| 2014/0078130 A1 | 3/2014 | Uchino et al. |
| 2014/0089833 A1 | 3/2014 | Hwang et al. |
| 2014/0094973 A1 | 4/2014 | Giaimo et al. |
| 2014/0098671 A1 | 4/2014 | Raleigh et al. |
| 2014/0104665 A1 | 4/2014 | Popovich et al. |
| 2014/0104685 A1 | 4/2014 | Bohn |
| 2014/0111865 A1 | 4/2014 | Kobayashi |
| 2014/0116982 A1 | 5/2014 | Schellenberg et al. |
| 2014/0140653 A1 | 5/2014 | Brown et al. |
| 2014/0140654 A1 | 5/2014 | Brown et al. |
| 2014/0143247 A1 | 5/2014 | Rathnavelu et al. |
| 2014/0143351 A1 | 5/2014 | Deng |
| 2014/0143439 A1 | 5/2014 | Ramamurthy |
| 2014/0176528 A1 | 6/2014 | Robbins |
| 2014/0184699 A1 | 7/2014 | Ito et al. |
| 2014/0189557 A1 | 7/2014 | O'Connell et al. |
| 2014/0204455 A1 | 7/2014 | Popovich |
| 2014/0240842 A1 | 8/2014 | Nguyen et al. |
| 2014/0300966 A1 | 10/2014 | Travers et al. |
| 2014/0314374 A1 | 10/2014 | Fattal et al. |
| 2014/0320399 A1 | 10/2014 | Kim et al. |
| 2015/0046500 A1 | 2/2015 | Bush et al. |
| 2015/0086163 A1* | 3/2015 | Valera .............. G02B 6/0035 385/37 |
| 2015/0168731 A1 | 6/2015 | Robbins |
| 2016/0033697 A1 | 2/2016 | Sainiemi et al. |
| 2016/0033784 A1 | 2/2016 | Levola et al. |
| 2016/0035539 A1 | 2/2016 | Sainiemi et al. |
| 2016/0110403 A1 | 4/2016 | Lomet et al. |
| 2016/0231257 A1 | 8/2016 | Kostamo et al. |
| 2016/0231477 A1 | 8/2016 | Saarikko et al. |
| 2016/0231566 A1 | 8/2016 | Levola et al. |
| 2016/0231567 A1 | 8/2016 | Saarikko |
| 2016/0231568 A1 | 8/2016 | Saarikko et al. |
| 2016/0231569 A1 | 8/2016 | Levola |
| 2016/0231570 A1 | 8/2016 | Levola et al. |
| 2016/0234485 A1 | 8/2016 | Robbins et al. |
| 2016/0283618 A1 | 9/2016 | Levola et al. |
| 2017/0235219 A1 | 8/2017 | Kostamo |

FOREIGN PATENT DOCUMENTS

| | | | |
|---|---|---|---|
| CN | 101105512 | | 1/2008 |
| CN | 102004315 | | 4/2011 |
| EP | 0977022 | | 2/2000 |
| EP | 1494109 | | 1/2005 |
| EP | 1847924 | | 10/2007 |
| EP | 2065750 | | 6/2009 |
| EP | 2083310 | | 7/2009 |
| EP | 2112547 | | 10/2009 |
| EP | 2144177 | | 1/2010 |
| EP | 2216678 | | 1/2010 |
| EP | 2196843 | | 6/2010 |
| EP | 2241926 | | 10/2010 |
| EP | 2662761 | | 11/2013 |
| EP | 2700987 | | 2/2014 |
| EP | 2752691 | | 7/2014 |
| EP | 2887121 | | 6/2015 |
| EP | 3018524 | | 5/2016 |
| FR | 2942811 | | 9/2010 |
| GB | 2500631 | | 10/2013 |
| JP | 55-057807 | * | 4/1980 |
| JP | S57109618 | | 7/1982 |
| JP | 59-009920 | * | 1/1984 |
| JP | 59-062888 | * | 4/1984 |
| JP | 60-188911 | * | 9/1985 |
| JP | 62-052506 | * | 3/1987 |
| JP | 62-278508 | * | 12/1987 |
| JP | 03-180801 | * | 8/1991 |
| JP | H0422358 | | 1/1992 |
| JP | 06-310806 | * | 11/1994 |
| JP | 7311303 | | 11/1995 |
| JP | 2000347037 | | 12/2000 |
| JP | 2001078234 | | 3/2001 |
| JP | 2008017135 | | 1/2008 |
| KR | 20070001771 | | 1/2007 |
| KR | 20090076539 | | 7/2009 |
| KR | 20090084316 | | 8/2009 |
| KR | 20110070087 | | 6/2011 |
| KR | 20120023458 | | 3/2012 |
| TW | 201407202 | | 2/2014 |
| WO | WO-9418595 | | 8/1994 |
| WO | WO 9952002 | | 10/1999 |
| WO | WO-0133282 | | 5/2001 |
| WO | WO-0177915 | | 10/2001 |
| WO | WO-0195027 | | 12/2001 |
| WO | WO-03090611 | | 11/2003 |
| WO | WO-2006054056 | | 5/2006 |
| WO | WO 2006064334 | | 6/2006 |
| WO | WO 2007052265 | | 5/2007 |
| WO | WO-2007057500 | | 5/2007 |
| WO | WO-2008021504 | | 2/2008 |
| WO | WO 2008081070 | | 7/2008 |
| WO | WO 2009029826 | | 3/2009 |
| WO | WO-2009077601 | | 6/2009 |
| WO | WO 2009127849 | | 10/2009 |
| WO | WO 2010092409 | | 8/2010 |
| WO | WO-2010125337 | | 11/2010 |
| WO | WO-2011003381 | | 1/2011 |
| WO | 2011051660 | | 5/2011 |
| WO | WO-2011051660 | | 5/2011 |
| WO | WO-2011090455 | | 7/2011 |
| WO | WO-2011110728 | | 9/2011 |
| WO | WO-2011131978 | | 10/2011 |
| WO | WO-2012172295 | | 12/2012 |
| WO | WO-2012177811 | | 12/2012 |
| WO | WO 2013033274 | | 3/2013 |
| WO | WO-2013058769 | | 4/2013 |
| WO | WO 2013164665 | | 11/2013 |
| WO | WO-2014051920 | | 4/2014 |
| WO | WO-2014085502 | | 6/2014 |
| WO | WO-2014088343 | | 6/2014 |
| WO | WO 2014111163 | | 7/2014 |
| WO | WO-2014130383 | | 8/2014 |
| WO | 2015/091669 | * | 6/2015 |
| WO | WO-2016014368 | | 1/2016 |
| WO | WO-2016064575 | | 4/2016 |

OTHER PUBLICATIONS

"Non-Final Office Action", U.S. Appl. No. 14/447,419, dated Feb. 2, 2016, 8 pages.

"Non-Final Office Action", U.S. Appl. No. 14/617,574, dated Feb. 26, 2016, 22 pages.

"Non-Final Office Action", U.S. Appl. No. 14/617,710, dated Mar. 2, 2016, 16 pages.

"Notice Of Allowance", U.S. Appl. No. 14/617,697, dated Feb. 29, 2016, 7 pages.

"Notice Of Allowance", U.S. Appl. No. 14/617,723, dated Feb. 9, 2016, 10 pages.

"Supplemental Notice of Allowance", U.S. Appl. No. 14/447,464, dated Jan. 12, 2016, 2 pages.

"Corrected Notice of Allowance", U.S. Appl. No. 14/617,723, dated Apr. 20, 2016, 7 pages.

"Final Office Action", U.S. Appl. No. 13/774,875, dated Apr. 22, 2016, 10 pages.

"Final Office Action", U.S. Appl. No. 14/447,419, dated May 17, 2016, 10 pages.

"International Search Report and Written Opinion", Application No. PCT/US2016/015496, dated Apr. 11, 2016, 11 pages.

"International Search Report and Written Opinion", Application No. PCT/US2016/015873, dated May 23, 2016, 11 pages.

"International Search Report and Written Opinion", Application No. PCT/US2016/016028, dated May 25, 2016, 11 pages.

(56) References Cited

OTHER PUBLICATIONS

"International Search Report and Written Opinion", Application No. PCT/US2016/016241, dated Apr. 20, 2016, 12 pages.
"International Search Report and Written Opinion", Application No. PCT/US2016/015869, dated May 12, 2016, 12 pages.
"International Search Report and Written Opinion", Application No. PCT/US2016/016029, dated May 12, 2016, 12 pages.
"International Search Report and Written Opinion", Application No. PCT/US2016/016027, dated May 17, 2016, 13 pages.
"International Search Report and Written Opinion", Application No. PCT/US2016/015871, dated Jun. 13, 2016, 13 pages.
"International Search Report and Written Opinion", Application No. PCT/US2016/019006, dated May 12, 2016, 14 pages.
"International Search Report and Written Opinion", Application No. PCT/US2016/016242, dated May 27, 2016, 14 pages.
"International Search Report and Written Opinion", Application No. PCT/US2016/015497, dated May 19, 2016, 17 pages.
"Non-Final Office Action", U.S. Appl. No. 14/335,927, dated Jun. 3, 2016, 8 pages.
"Non-Final Office Action", U.S. Appl. No. 14/617,606, dated May 23, 2016, 12 pages.
"Notice of Allowance", U.S. Appl. No. 14/617,723, dated May 24, 2016, 7 pages.
"Notice of Allowance", U.S. Appl. No. 14/617,735, dated Apr. 5, 2016, 12 pages.
"Notice of Allowance", U.S. Appl. No. 14/617,746, dated Apr. 11, 2016, 7 pages.
Kim,"Determination of small angular displacement by moire fringes of matched radial-parallel gratings", Applied Optics, vol. 36, No. 13, May 1997, 8 pages.
Levola,"Diffractive optics for virtual reality displays", Journal of the Society for Information Display—SID, Jan. 1, 2006, 9 pages.
Theocaris,"Radial Gratings as Moire Gauges", Journal of Physics E. Scientific Instruments, Jun. 1, 1968, 6 pages.
"International Search Report and Written Opinion", Application No. PCT/US2015/042371, dated Oct. 2, 2015, 10 pages.
"International Search Report and Written Opinion", Application No. PCT/US2015/042187, dated Oct. 20, 2015, 10 pages.
"International Search Report and Written Opinion", Application No. PCT/US2015/042226, dated Oct. 27, 2015, 10 Pages.
"International Search Report and Written Opinion", Application No. PCT/US2015/042205, dated Oct. 30, 2015, 10 pages.
"International Search Report and Written Opinion", Application No. PCT/US2015/042218, dated Nov. 6, 2015, 10 pages.
"International Search Report and Written Opinion", Application No. PCT/US2015/042259, dated Oct. 12, 2015, 11 pages.
"International Search Report and Written Opinion", Application No. PCT/US2015/041930, dated Oct. 20, 2015, 12 Pages.
"International Search Report and Written Opinion", Application No. PCT/US2015/041900, dated Oct. 21, 2015, 12 pages.
"International Search Report and Written Opinion", Application No. PCT/US2015/041909, dated Oct. 20, 2015, 13 pages.
"International Search Report and Written Opinion", Application No. PCT/US2015/041046, dated Nov. 9, 2015, 15 pages.
"Notice of Allowance", U.S. Appl. No. 14/447,464, dated Nov. 9, 2015, 10 pages.
"Restriction Requirement", U.S. Appl. No. 14/617,697, dated Nov. 30, 2015, 6 pages.
Ando,"Development of Three-Dimensional Microstages Using Inclined Deep-Reactive Ion Etching", Journal of Microelectromechanical Systems, Jun. 1, 2007, 10 pages.
Antonopoulos,"Efficient Updates for Web-Scale Indexes over the Cloud", IEEE 28th International Conference on Data Engineering Workshops, Apr. 2012, 8 pages.
Garcia,"COMET: Content Mediator Architecture for Content-Aware Networks", In IEEE Future Network & Mobile Summit, 2011, 8 pages.
Gila,"First Results From A Multi-Ion Beam Lithography And Processing System At The University Of Florida", AIP Conference Proceedings, Jun. 1, 2011, 6 pages.
Levandoski,"Ranking and New Database Architectures", In Proceedings of the 7th International Workshop on Ranking in Databases, Aug. 2013, 4 pages.
"Adobe Audition / Customizing Workspaces", Retrieved From: <http://help.adobe.com/en_US/audition/cs/using/WS9FA7B8D7-5991-4e05-B13C-4C85DAF1F051.html> Jul. 5, 2014, May 18, 2011, 6 Pages.
"Always Connected", Available at: http://www.samsung.com/global/microsite/galaxycamera/nx/, Jun. 24, 2013, 5 pages.
"Controlling Your Desktop's Power Management", Retrieved From: <http://www.vorkon.de/SU1210.001/drittanbieter/Dokumentation/openSUSE_11.2/manual/sec.gnomeuser.start.power_mgmt.html> Jul. 7, 2014, 6 Pages.
"Display Control", Retrieved From: <http://www.portrait.com/technology/display-control.html> Jul. 4, 2014, Jun. 24, 2013, 5 Pages.
"Manage Multiple Windows", Retrieved From: <http://windows.microsoft.com/en-hk/windows/manage-multiple-windows#1TC=windows-7> Jul. 8, 2014, 4 Pages.
"Merge Operator", Retrieved on: Jun. 3, 2014, Available at: https://github.com/facebook/rocksdb/wiki/Merge-Operator, 10 pages.
"Non-Final Office Action", U.S. Appl. No. 13/774,875, dated Sep. 16, 2015, 8 pages.
"Organize Your Desktop Workspace for More Comfort with Window Space", Retrieved From: <http://www.ntwind.com/software/windowspace.html> Jul. 4, 2014, Sep. 19, 2008, 5 Pages.
"SizeUp The Missing Window Manager", Retrieved From: <https://www.irradiatedsoftware.com/sizeup/> Jul. 4, 2014, Jan. 17, 2013, 4 Pages.
"Using Flickr to Organize a Collection of Images", Available at: http://www.jiscdigitalmedia.ac.uk/guide/using-flickr-to-organise-a-collection-of-images, Apr. 2, 2013, 17 pages.
"Window Magnet", Retrieved From: <http://magnet.crowdcafe.com/> Jul. 4, 2014, Jun. 23, 2011, 2 Pages.
"Windows 7: Display Reminder When Click on Shutdown?", Retrieved From: <http://www.sevenforums.com/customization/118688-display-reminder-when-click-shutdown.html> Jul. 8, 2014, Oct. 18, 2010, 5 Pages.
"Working with Windows", Retrieved From: <http://windows.microsoft.com/en-us/windows/working-with-windows#1TC=windows-7> Jul. 4, 2014, 10 Pages.
Ashraf,"Winsplit Revolution: Tile, Resize, and Position Windows for Efficient Use of Your Screen", Retrieved From: <http://dottech.org/11240/winsplit-revolution-tile-resize-and-position-windows-for-efficient-use-of-your-screen/> Jul. 8, 2014, Dec. 18, 2011, 4 Pages.
Callaghan,"Types of writes", Available at: http://smalldatum.blogspot.in/2014/04/types-of-writes.html, Apr. 17, 2014, 3 pages.
Cohen,"Automatic Strategies in the Siemens RTL Tiled Window Manager", In Proceedings: The 2nd IEEE Conference on Computer Workstations, Mar. 7, 1988, pp. 111-119.
Eckel,"Personalize Alerts with the Help of OS X Mavericks Notifications", Retrieved From: <http://www.techrepublic.com/article/customize-os-x-mavericks-notifications-to-personalize-alerts/> Jul. 8, 2014, Mar. 10, 2014, 7 Pages.
Elnaka,"Real-Time Traffic Classification for Unified Communication Networks", In Proceedings of International Conference on Selected Topics in Mobile and Wireless Networking, Aug. 19, 2013, 6 pages.
Hepburn,"Color: The Location Based Social Photo App", Available at: http://www.digitalbuzzblog.com/color-the-location-based-social-photo-iphone-app/, Mar. 27, 2011, 12 pages.
Johnson,"Samsung Galaxy Tab Pro 10.1 Review", Retrieved From: <http://hothardware.com/Reviews/Samsung-Galaxy-Tab-Pro-101-Review/?page=3#!baG2DY > Jul. 20, 2014, Mar. 21, 2014, 10 Pages.
Kandogan,"Elastic Windows: Improved Spatial Layout and Rapid Multiple Window Operations", In Proceedings of the Workshop on Advanced Visual Interfaces, May 27, 1996, 10 Pages.
Levandoski,"Latch-Free, Log-Structured Storage for Multiple Access Methods", U.S. Appl. No. 13/924,567, filed Jun. 22, 2013, 51 pages.

(56) References Cited

OTHER PUBLICATIONS

Levandoski,"The Bw-Tree: A B-tree for New Hardware Platforms", In IEEE 29th International Conference on Data Engineering, Apr. 8, 2013, 12 pages.
Li,"QRON: QoS-Aware Routing in Overlay Networks", In Proceedings of IEEE Journal on Selected Areas in Communications, vol. 22, No. 1, Jan. 2004, 12 pages.
Mack,"Moto X: The First Two Weeks", Retrieved From: <http://www.gizmag.com/two-weeks-motorola-google-moto-x-review/28722/> Jul. 8, 2014, Aug. 16, 2013, 8 pages.
O'Reilly,"How to Use the Microsoft Surface Touch Screen and Keyboard", Retrieved From: <http://www.cnet.com/how-to/how-to-use-the-microsoft-surface-touch-screen-and-keyboard/> Jul. 5, 2014, Nov. 6, 2012, 5 Pages.
Paul,"Three Windows Multitasking Features That Help Maximize Your Screen Space", Retrieved From: <http://www.pcworld.com/article/2094124/three-windows-multitasking-features-that-help-maximize-your-screen-space.html> Jul. 4, 2014, Feb. 4, 2014, 4 Pages.
Prohaska,"Fast Updates with TokuDB", Available at: http://www.tokutek.com/2013/02/fast-updates-with-tokudb/, Feb. 12, 2013, 2 pages.
Thurrott,"Nokia Lumia "Black": Glance 2.0", Retrieved From:<http://winsupersite.com/windows-phone/nokia-lumia-black-glance-20> Jul. 8, 2014, Jan. 11, 2014, 3 Pages.
Vranjes,"Application Window Divider Control for Window Layout Management", U.S. Appl. No. 13/863,369, filed Apr. 15, 2013, 21 pages.
Wiebe,"Using screen space efficiently with Gridmove", Available at: http://lowerthought.wordpress.com/2010/05/15/using-screen-space-efficiently-with-gridmove/, May 15, 2010, 2 pages.
"Restriction Requirement", U.S. Appl. No. 14/447,419, dated Aug. 4, 2015, 6 pages.
Chang-Yen, et al., "A Monolithic PDMS Waveguide System Fabricated Using Soft-Lithography Techniques", In Journal of Lightwave Technology, vol. 23, No. 6, Jun. 2005, 6 pages.
Teng, et al., "Fabrication of nanoscale zero-mode waveguides using microlithography for single molecule sensing", In Proceedings of Nanotechnology, vol. 23, No. 45, Jul. 7, 2012, 7 pages.
Tien, et al., "Microcontact Printing of SAMs", In Proceedings of Thin Films, vol. 24, May 28, 2014, 24 pages.
"Advisory Action", U.S. Appl. No. 13/428,879, dated Sep. 19, 2014, 3 pages.
"Augmented Reality and Physical Games", U.S. Appl. No. 13/440,165, dated Apr. 5, 2012, 49 pages.
"BragGrate Mirror", Retrieved from <http://web.archive.org/web/20090814104232/http://www.optigrate.com/BragGrate_Mirror.html> on Jul. 8, 2014, Aug. 14, 2009, 2 pages.
"Corrected Final Office Action", U.S. Appl. No. 13/432,311, dated Dec. 24, 2014, 25 pages.
"Corrected Notice of Allowance", U.S. Appl. No. 13/355,836, dated Sep. 11, 2014, 2 pages.
"Corrected Notice of Allowance", U.S. Appl. No. 13/355,836, dated Dec. 15, 2014, 2 pages.
"DigiLens", SBG Labs, retrieved from <http://www.digilens.com/products.html> on Jun. 19, 2012, 1 page.
"Final Office Action", US. Appl. No. 13/336,873, dated Jan. 5, 2015, 21 pages.
"Final Office Action", U.S. Appl. No. 13/336,895, dated May 27, 2014, 11 pages.
"Final Office Action", U.S. Appl. No. 13/355,836, dated Mar. 10, 2014, 18 pages.
"Final Office Action", U.S. Appl. No. 13/355,914, dated Feb. 23, 2015, 21 pages.
"Final Office Action", U.S. Appl. No. 13/355,914, dated Jun. 19, 2014, 11 pages.
"Final Office Action", U.S. Appl. No. 13/397,495, dated May 29, 2014, 10 pages.
"Final Office Action", U.S. Appl. No. 13/397,516, dated Jan. 29, 2015, 13 pages.
"Final Office Action", U.S. Appl. No. 13/397,539, dated Jun. 29, 2015, 11 pages.
"Final Office Action", U.S. Appl. No. 13/428,879, dated Jul. 14, 2014, 12 pages.
"Final Office Action", U.S. Appl. No. 13/432,311, dated Dec. 15, 2014, 24 pages.
"Final Office Action", U.S. Appl. No. 13/432,372, dated Jan. 29, 2015, 33 pages.
"Final Office Action", U.S. Appl. No. 13/440,165, dated Jun. 6, 2014, 12 pages.
"Final Office Action", U.S. Appl. No. 13/440,165, dated Jul. 21, 2015, 11 pages.
"Final Office Action", U.S. Appl. No. 13/477,646, dated Feb. 23, 2015, 36 pages.
"Final Office Action", U.S. Appl. No. 13/477,646, dated May 5, 2014, 26 pages.
"Final Office Action", U.S. Appl. No. 13/525,649, dated Oct. 9, 2014, 8 pages.
"Final Office Action", U.S. Appl. No. 13/774,875, dated Jun. 4, 2015, 10 pages.
"Final Office Action", U.S. Appl. No. 14/134,993, dated Jul. 16, 2015, 19 pages.
"Final Office Action", U.S. Appl. No. 14/134,993, dated Aug. 20, 2014, 15 pages.
"Foreign Notice of Allowance", CN Application No. 201320034345.X, dated Aug. 14, 2013, 2 Pages.
"Foreign Office Action", CN Application No. 201210563730.3, dated Jan. 7, 2015, 16 pages.
"Foreign Office Action", CN Application No. 201210567932.5, dated Aug. 14, 2014, 12 pages.
"Foreign Office Action", EP Application No. 13769961.7, dated Mar. 11, 2015, 8 pages.
"Foreign Office Action", EP Application No. 13769961.7, dated Jun. 30, 2015, 6 pages.
"HDTV Helmet Mounted Display", Available at <http://defense-update.com/products/h/HDTV-HMD.htm>, Jan. 26, 2005, 1 page.
"International Search Report and Written Opinion", Application No. PCT/US2012/069331, dated Mar. 29, 2013, 10 pages.
"International Search Report and Written Opinion", Application No. PCT/US2014/016658, dated Apr. 23, 2014, 10 pages.
"International Search Report and Written Opinion", Application No. PCT/US2013/053676, dated Oct. 16, 2013, 10 pages.
"International Search Report and Written Opinion", Application No. PCT/US2013/030632, dated Jun. 26, 2013, 10 pages.
"International Search Report and Written Opinion", Application No. PCT/US2013/028477, dated Jun. 21, 2013, 11 pages.
"International Search Report and Written Opinion", Application No. PCT/US2013/031111, dated Jun. 26, 2013, 11 pages.
"International Search Report and Written Opinion", Application No. PCT/US2013/076832, dated Mar. 17, 2014, 12 pages.
"International Search Report and Written Opinion", Application No. PCT/US2013/061225, dated Jun. 4, 2014, 12 pages.
"International Search Report and Written Opinion", Application No. PCT/US2012/071563, dated Apr. 25, 2013, 13 pages.
"International Search Report and Written Opinion", Application No. PCT/US2013/021784, dated Apr. 30, 2013, 9 pages.
"International Search Report and Written Opinion", Application No. PCT/US2012/069330, dated Mar. 28, 2013, 9 pages.
"International Search Report and Written Opinion", Application No. PCT/US2013/021783, dated May 15, 2013, 9 pages.
"International Search Report and Written Opinion", Application No. PCT/US2013/026200, dated Jun. 3, 2013, 9 pages.
"Light Guide Techniques using LED Lamps", Application Brief I-003, retrieved from <http://www.ciri.org.nz/downloads/Lightpipe%20design.pdf> on Jan. 12, 2012, Oct. 14, 2008, 22 pages.
"New Technology from MIT may Enable Cheap, Color, Holographic Video Displays", Retrieved from <http://www.gizmag.com/holograph-3d-color-video-display-inexpensive-mit/28029/> on Feb. 25, 2015, Jun. 24, 2013, 8 pages.
"Non-Final Office Action", U.S. Appl. No. 13/397,495, dated Nov. 13, 2013, 8 pages.
"Non-Final Office Action", U.S. Appl. No. 13/440,165, dated Feb. 6, 2014, 12 pages.

(56) References Cited

OTHER PUBLICATIONS

"Non-Final Office Action", U.S. Appl. No. 13/336,873, dated Apr. 9, 2015, 18 pages.
"Non-Final Office Action", U.S. Appl. No. 13/336,873, dated Jul. 25, 2014, 16 pages.
"Non-Final Office Action", U.S. Appl. No. 13/336,895, dated Oct. 24, 2013, 9 pages.
"Non-Final Office Action", U.S. Appl. No. 13/343,675, dated Jul. 16, 2013, 9 pages.
"Non-Final Office Action", U.S. Appl. No. 13/355,836, dated Nov. 4, 2013, 15 pages.
"Non-Final Office Action", U.S. Appl. No. 13/355,914, dated Feb. 14, 2014, 10 pages.
"Non-Final Office Action", U.S. Appl. No. 13/355,914, dated Oct. 28, 2014, 18 pages.
"Non-Final Office Action", U.S. Appl. No. 13/397,495, dated Apr. 3, 2015, 11 pages.
"Non-Final Office Action", U.S. Appl. No. 13/397,516, dated Jun. 12, 2014, 11 pages.
"Non-Final Office Action", U.S. Appl. No. 13/397,516, dated Nov. 25, 2013, 10 pages.
"Non-Final Office Action", U.S. Appl. No. 13/397,539, dated Mar. 16, 2015, 9 pages.
"Non-Final Office Action", U.S. Appl. No. 13/397,617, dated May 5, 2015, 6 pages.
"Non-Final Office Action", U.S. Appl. No. 13/397,617, dated Oct. 9, 2014, 6 pages.
"Non-Final Office Action", U.S. Appl. No. 13/428,879, dated Feb. 24, 2015, 10 pages.
"Non-Final Office Action", U.S. Appl. No. 13/428,879, dated Mar. 17, 2014, 10 pages.
"Non-Final Office Action", U.S. Appl. No. 13/428,879, dated Jun. 26, 2015, 13 pages.
"Non-Final Office Action", U.S. Appl. No. 13/432,311, dated Jun. 2, 2015, 25 pages.
"Non-Final Office Action", U.S. Appl. No. 13/432,311, dated Jul. 8, 2014, 33 pages.
"Non-Final Office Action", U.S. Appl. No. 13/432,372, dated May 9, 2014, 26 pages.
"Non-Final Office Action", U.S. Appl. No. 13/432,372, dated Oct. 24, 2014, 27 pages.
"Non-Final Office Action", U.S. Appl. No. 13/440,165, dated Feb. 13, 2015, 10 pages.
"Non-Final Office Action", U.S. Appl. No. 13/440,165, dated Oct. 16, 2014, 11 pages.
"Non-Final Office Action", U.S. Appl. No. 13/477,646, dated Jun. 18, 2015, 43 pages.
"Non-Final Office Action", U.S. Appl. No. 13/477,646, dated Oct. 6, 2014, 34 pages.
"Non-Final Office Action", U.S. Appl. No. 13/477,646, dated Nov. 22, 2013, 20 pages.
"Non-Final Office Action", U.S. Appl. No. 13/525,649, dated Jan. 29, 2014, 7 pages.
"Non-Final Office Action", U.S. Appl. No. 13/525,649, dated Feb. 5, 2015, 7 pages.
"Non-Final Office Action", U.S. Appl. No. 13/525,649, dated Jun. 5, 2014, 7 pages.
"Non-Final Office Action", U.S. Appl. No. 13/570,073, dated Jan. 23, 2015, 7 pages.
"Non-Final Office Action", U.S. Appl. No. 13/631,308, dated Feb. 23, 2015, 9 pages.
"Non-Final Office Action", U.S. Appl. No. 13/722,917, dated May 21, 2015, 12 pages.
"Non-Final Office Action", U.S. Appl. No. 13/774,875, dated Nov. 24, 2014, 8 pages.
"Non-Final Office Action", U.S. Appl. No. 14/134,993, dated Jan. 22, 2015, 17 pages.
"Non-Final Office Action", U.S. Appl. No. 14/134,993, dated Apr. 17, 2014, 34 pages.
"Notice of Allowance", U.S. Appl. No. 13/336,895, dated Aug. 11, 2014, 6 pages.
"Notice of Allowance", U.S. Appl. No. 13/343,675, dated Sep. 16, 2013, 8 pages.
"Notice of Allowance", U.S. Appl. No. 13/355,836, dated Jun. 13, 2014, 11 pages.
"Notice of Allowance", U.S. Appl. No. 13/355,836, dated Oct. 8, 2014, 11 pages.
"Notice of Allowance", U.S. Appl. No. 13/356,545, dated Mar. 28, 2014, 6 pages.
"Notice of Allowance", U.S. Appl. No. 13/488,145, dated Nov. 19, 2014, 8 pages.
"Restriction Requirement", U.S. Appl. No. 13/355,836, dated Sep. 27, 2013, 6 pages.
"Restriction Requirement", U.S. Appl. No. 13/397,539, dated Dec. 1, 2014, 6 pages.
"Restriction Requirement", U.S. Appl. No. 13/488,145, dated Sep. 8, 2014, 14 pages.
"Restriction Requirement", U.S. Appl. No. 13/570,073, dated Nov. 18, 2014, 7 pages.
"Supplemental Notice of Allowance", U.S. Appl. No. 13/356,545, dated Jul. 22, 2014, 2 pages.
"Supplementary European Search Report", EP Application No. 13769961.7, dated Mar. 3, 2015, 3 pages.
"Two-Faced: Transparent Phone with Dual Touch Screens", Retrieved from <http://gajitz.com/two-faced-transparent-phone-with-dual-touch-screens/>, Jun. 7, 2012, 3 pages.
"Variable Groove Depth (VGD) Master Gratings", Retrieved From: <http://www.horiba.com/scientific/products/diffraction-gratings/catalog/variable-groove-depth-vgd/> May 28, 2014, 2 pages.
"Written Opinion", Application No. PCT/US2013/061225, dated Oct. 10, 2014, 6 Pages.
Allen,"ELiXIR—Solid-State Luminaire with Enhanced Light Extraction by Internal Reflection", Journal of Display Technology, vol. 3, No. 2, Available at <http://www.nanolab.uc.edu/Publications/PDFfiles/355.pdf>, Jun. 2007, pp. 155-159.
Aron,"'Sprinting' chips could push phones to the speed limit", New Scientist, Feb. 20, 2012, Issue #2852, Feb. 20, 2012, 2 pages.
Baluja,"Non-Intrusive Gaze Tracking Using Artificial Neural Networks", Technical Report CMU-CS-94-102, Available at <http://citeseerx.ist.psu.edu/viewdoc/download?doi=10.1.1.33.4027&rep=rep1&type=pdf>, Jan. 5, 1994, 14 pages.
Barger,"COTS Cooling", Publication of the National Electronics Manufacturing Center of Excellence, Retrieved from: <http://www.empf.org/empfasis/2009/Oct09/cots.html > on Jul. 9, 2012, Oct. 2009, 4 pages.
Baudisch,"Back-of-Device Interaction Allows Creating Very Small Touch Devices", In Proceedings of 27th International Conference on Human Factors in Computing Systems, Retrieved from <http://citeseerx.ist.psu.edu/viewdoc/download?doi=10.1.1.160.3337&rep=rep1&type=pdf>, Apr. 2005, 10 pages.
Baxtor,"TwinTech GeForce GTS 250 XT OC 1GB Graphics Card", retrieved from <http://www.tweaktown.com/reviews/2733/twintech_geforce_gts_250_xt_oc_1gb_graphics_card/index3.html> on Dec. 30, 2011, Apr. 24, 2009, 4 pages.
Charles,"Design of Optically Path Length Matched, Three-Dimensional Photonic Circuits Comprising Uniquely Routed Waveguides", In Proceedings of Applied Optics, vol. 51, Issue 27, Sep. 20, 2012, 11 pages.
Chen,"A Study of Fiber-to-Fiber Losses in Waveguide Grating Routers", In Journal of Lightwave Technology, vol. 15, No. 10, Oct. 1997, 5 pages.
Chen,"Strategies for 3D Video with Wide Fields-of-View", IEEE Proceeding Optoelectronics, vol. 148, Issue 2, Available at <http://ieeexplore.ieee.org/stamp/stamp.jsp?tp=&arnumber=926823>, Apr. 2001, pp. 85-90.
Cheng,"Waveguide Displays Based on Polymer-dispersed Liquid Crystals", SPIE Newsroom, Available at <http://spie.org/documents/Newsroom/Imported/003805/003805_10.pdf>, Aug. 12, 2011, 2 pages.
Chirgwin,"Researchers propose 'overclock' scheme for mobiles—Processing at a sprint to overcome tech limitations", The Register, Feb. 21, 2012, Feb. 21, 2012, 2 pages.

(56) References Cited

OTHER PUBLICATIONS

Coldewey,"Researchers Propose "Computational Sprinting" To Speed Up Chips By 1000%—But Only For A Second", TechCrunch, Feb. 28, 2012, Feb. 29, 2012, 2 pages.

Cottier,"Label-free Highly Sensitive Detection of (small) Molecules by Wavelength Interrogation of Integrated Optical Chips", n Proceedings of Sensors and Actuators B: Chemical, vol. 91, Issue 1-3, Jun. 1, 2003, pp. 241-251.

DeAgazio,"Selecting Display Backlighting for Portable, Handheld Devices", Hearst Electronics Products, retrieved from <http://www2.electronicproducts.com/Selecting_display_backlighting_for_portable_handheld_devices-article-farcglobal-feb2008-html.aspx> on Jan. 12, 2012, Jan. 2, 2008, 4 pages.

Dumon,"Compact Arrayed Waveguide Grating Devices in Silicon-on-Insulator", In Proceedings of the IEEE/LEOS Symposium Benelux Chapter, May 27, 2014, 4 pages.

Eadicicco,"First Transparent Tablet Lets You Touch From Both Sides", Retrieved from <http://blog.laptopmag.com/first-transparent-tablet>, Dec. 26, 2013, 4 pages.

Glendenning,"Polymer Micro-Optics via Micro Injection Moulding", Available at: https://web.archive.org/web/20120310003606/http://www.microsystems.uk.com/english/polymer_optics_injection_moulding.html, Jan. 10, 2011, 6 pages.

Grabarnik,"Concave Diffraction Gratings Fabricated With Planar Lithography", In Proceedings of SPIE, vol. 6992, May 3, 2008, 8 pages.

Greenemeier,"Could "Computational Sprinting" Speed Up Smart Phones without Burning Them Out?", Scientific American, Feb. 29, 2012, Feb. 29, 2012, 2 pages.

Greiner,"Bandpass engineering of lithographically scribed channel-waveguide Bragg gratings", In Proceedings of Optics Letters, vol. 29, No. 8, Apr. 15, 2004, pp. 806-808.

Han,"Accurate diffraction efficiency control for multiplexed volume holographic gratings", Retrieved at: opticalengineering.spiedigitallibrary.org/data/Journals/.../2799_1, 2002, 4 pages.

Hua,"Engineering of Head-mounted Projective Displays", In Proceedings of Applied Optics, vol. 39, No. 22, Aug. 1, 2000, 11 pages.

Ismail,"Improved Arrayed-Waveguide-Grating Layout Avoiding Systematic Phase Errors", In Proceedings of Optics Express, vol. 19, No. 9, Apr. 25, 2011, pp. 8781-8794.

Jacques,"Polarized Light Imaging of Tissue", Available at <http://www.lumamed.com/documents/5_polarized%20light%20imaging.pdf>, 2004, 17 pages.

Jarvenpaa,"Compact near-to-eye display with integrated gaze tracker", Second International Conference on Computer Engineering and Applications, Mar. 19, 2010, 9 pages.

Jaworski,"A Novel Design of Heat Sink with PCM for Electronics Cooling", 10th International Conference on Thermal Energy Storage, Stockton, May 31-Jun. 2, 2006, retrieved from <https://intraweb.stockton.edu/eyos/energy_studies/content/docs/FINAL_PRESENTATIONS/4b-6%20.pdf> on Jan. 5, 2012, May 31, 2006, 8 pages.

Karp,"Planar Micro-optic Solar Concentration using Multiple Imaging Lenses into a Common Slab Waveguide", In Proceedings of SPIE vol. 7407, Available at <http://psilab.ucsd.edu/research/slab_concentration/files/SPIE_Slab_Published.pdf>, Jan. 2009, 11 pages.

Kress,"Exit Pupil for Wearable See-through displays", Downloaded From: http://proceedings.spiedigitallibrary.org/ on Jan. 31, 2015 Terms of Use: http://spiedl.org/terms, 2012, 8 pages.

Krishnan,"A Novel Hybrid Heat Sink Using Phase Change Materials for Transient Thermal Management of Electronics", IEEE transactions on components and packaging technologies, vol. 28, No. 2, retrieved from <http://ieeexplore.ieee.org/stamp/stamp.jsp?tp=&arnumber=1432936> on Jan. 5, 2012, Jun. 2005, pp. 281-289.

L,"All-Nanoparticle Concave Diffraction Grating Fabricated by Self-Assembly onto Magnetically-Recorded Templates", In Proceedings of Optical Express, vol. 21, Issue 1, Jan. 2013, 1 page.

Lanman,"Near-eye Light Field Displays", In Journal of ACM Transactions on Graphics, vol. 32, No. 6, Nov. 2013, 10 pages.

Large,"Parallel Optics in Waveguide Displays: a Flat Panel Autostereoscopic", Display Technology, Journal of, Retrieved from <http://download.microsoft.com/download/D/2/E/D2E425F8-CF3C-4C71-A4A2-70F9D4081007/ParallelOpticsinWaveguideDisplaysMS090925.Final.pdf>, Jun. 21, 2010, pp. 1-7.

Lerner,"Penn Helps Rethink Smartphone Design With 'Computational Sprinting'", Penn News Release, Feb. 28, 2012, 2 pages.

Li,"Design Optimization of Reflective Polarizers for LCD Backlight Recycling", Journal of Display Technology, vol. 5, No. 8, Available at <http://ieeexplore.ieee.org/stamp/stamp.jsp?tp=&arnumber=5196840 >, Aug. 2009, pp. 335-340.

Li,"Switchable Electro-optic Diffractive Lens with High Efficiency for Ophthalmic Applications", PNAS Apr. 18, 2006 vol. 103 No. 16 6100-6104, Retrieved from: <http://www.pnas.org/content/103/16/6100.long> Feb. 22, 2012, Feb. 2, 2006, 4 pages.

Lindau,"Controlling the Groove Depth Of Holographic Gratings", In Proceedings of Optical System Design, Analysis, and Production, vol. 0399, Oct. 26, 1983, 2 pages.

Man,"IT Equipment Noise Emission Standards: Overview of New Development in the Next Edition of ISO/ECMA Standards", In Proceedings of 37th International Congress and Exposition on Noise Control Engineering, Available at <http://www.ecma-international.org/activities/Acoustics/Inter-noise%202008%20paper%20on%20%20ECMA-74%20updates.pdf >, Oct. 26, 2008, 8 pages.

Massenot,"Multiplexed holographic transmission gratings recorded in holographic polymer-dispersed liquid crystals: static and dynamic studies", Retrieved at: http://oatao.univ-toulouse.fr/2874/, 2005, 8 pages.

McMillan,"Your Future iPhone May Be Stuffed With Wax", Aug. 23, 2013, 3 pages.

Mei,"An all fiber interferometric gradient hydrophone with optical path length compensation", In Proceedings of Summaries of Papers Presented at the Conference on Lasers and Electro-Optics, May 28, 1999, 2 pages.

Melcher,"LCoS for High Performance Displays", In Proceedings of LEOS 2003, Available at <http://ieeexplore.ieee.org/stamp/stamp.jsp?tp=&arnumber=1253048>, Oct. 27, 2003, pp. 812-813.

Minier,"Diffraction Characteristics of Superimposed Holographic gratings in Planar Optical waveguides", IEEE Photonics Technology Letters, vol. 4, No. 10, Oct. 1992, 4 pages.

Moore,"Computational sprinting pushes smartphones till they're tired", Michigan News Release, Feb. 28, 2012, 2 pages.

Morga,"History of SAW Devices", In Proceedings of the IEEE International Frequency Control Symposium, May 27, 1998, 22 pages.

Nguyen,"Advanced Cooling System Using Miniature Heat Pipes in Mobile PC", IEEE Transactions on Components and Packaging Technology, vol. 23, No. 1, Available at <http://ieeexplore.ieee.org/stamp/stamp.jsp?tp=&arnumber=833046&userType=inst>, Mar. 2000, pp. 86-90.

Owano,"Study explores computing bursts for smartphones", PhysOrg.com, Feb. 21, 2012, Feb. 21, 2012, 2 pages.

Papaefthymiou,"Computational Sprinting on a Hardware/Software Testbed", In the Proceedings of the 18th Eighteenth International Conference on Architectural Support for Programming Languages and Operating Systems (ASPLOS), Mar. 2013., Mar. 2013, 12 pages.

Patrizio,"Researchers Working on Ways to Put 16-Core Processors in Smartphones", Brighthand, Mar. 18th, 2012, Mar. 18, 2012, 2 pages.

Pu,"Exposure schedule for multiplexing holograms in photopolymer films", Retrieved at: lo.epfl.ch/webdav/site/lo/shared/1996/OE_35_2824_Oct1996.pdf, Oct. 1996, 6 pages.

Raghavan,"Computational Sprinting", In the Proceedings of the 18th Symposium on High Performance Computer Architecture (HPCS), Feb. 2012, Feb. 2012, 12 pages.

Raghavan,"Designing for Responsiveness With Computational Sprinting", IEEE Micro's "Top Picks of 2012" Issue, May 2013, 8 pages.

(56) References Cited

OTHER PUBLICATIONS

Scott,"RearType: Text Entry Using Keys on the Back of a Device", In Proceedings of 12th Conference on Human-Computer Interaction with Mobile Devices and Services, Retrieved from <https://research.microsoft.com/pubs/135609/reartype%20mobilehci.pdf>, Sep. 7, 2010, 9 pages.
Singh"Laser-Based Head-Tracked 3D Display Research", Journal of Display Technology, vol. 6, No. 10, Available at <http://ieeexplore.ieee.org/stamp/stamp.jsp?tp=&arnumber=5462999>, Oct. 2010, pp. 531-543.
Smalley,"Anisotropic Leaky-Mode Modulator for Holographic Video Displays", In Proceedings of Nature, vol. 498, Jun. 20, 2013, 6 pages.
Stupar,"Optimization of Phase Change Material Heat Sinks for Low Duty Cycle High Peak Load Power Supplies", IEEE transactions on components, packaging and manufacturing technology, retrieved from <http://ieeexplore.ieee.org/stamp/stamp.jsp?tp=&arnumber=6081913> on Jan. 5, 2012, Nov. 15, 2011, 14 pages.
Tari,"CFD Analyses of a Notebook Computer Thermal Management System and a Proposed Passive Cooling Alternative", IEEE Transactions on Components and Packaging Technologies, vol. 33, No. 2, retrieved from <http://ieeexplore.ieee.org/stamp/stamp.jsp?tp=&arnumber=5466211> on Dec. 30, 2011, Jun. 2010, pp. 443-452.
Travis,"Collimated Light from a Waveguide for a Display Backlight", Optics Express—Retrieved from <http://download.microsoft.com/download/D/2/E/D2E425F8-CF3C-4C71-A4A2-70F9D4081007/OpticsExpressbacklightpaper.pdf>, Oct. 15, 2009, pp. 19714-19719.
Travis,"The Design of Backlights for View-Sequential 3D", Microsoft Corporation, Available at <http://download.microsoft.com/download/D/2/E/D2E425F8-CF3C-4C71-A4A2-70F9D4081007/Backlightforviewsequentialautostereo.docx>, Jul. 3, 2010, 4 pages.
Van"A Survey of Augmented Reality Technologies, Applications and Limitations", The International Journal of Virtual Reality, 2010, 9(2), Available at <http://www.ijvr.org/issues/issue2-2010/paper1%20.pdf>, Jun. 2010, pp. 1-19.
Walker,"Thermalright Ultra-120 Extreme CPU Cooler", retrieved from <http://www.pro-clockers.com/cooling/66-thermalright-ultra-120-extreme-cpu-cooler.html> on Dec. 30, 2011, Jul. 2, 2009, 7 pages.
Westerinen,"Light Guide Display and Field of View", U.S. Appl. No. 13/428,879, filed Mar. 23, 2012, 46 pages.
Wigdor,"LucidTouch: A See-Through Mobile Device", In Proceedings of 20th Annual ACM symposium on User Interface Software and Technology, Retrieved from <http://dl.acm.org/citation.cfm?id=1294259>, Oct. 7, 2007, 10 pages.
Xie,"Fabrication of Varied-Line-Spacing Grating by Elastic Medium", In Proceedings SPIE 5636, Holography, Diffractive Optics, and Applications II, Nov. 2004, 4 pages.
Yan,"Multiplexing holograms in the photopolymer with equal diffraction efficiency", 2005, 9 pages.
Zharkova,"Study of the Dynamics of Transmission Gratings Growth on Holographic Polymer-Dispersed Liquid Crystals", International Conference on Methods of Aerophysical Research, ICMAR 2008, 2008, 4 pages.
"Corrected Notice of Allowance", U.S. Appl. No. 14/617,574, dated Sep. 12, 2016, 10 pages.
"Corrected Notice of Allowance", U.S. Appl. No. 14/617,574, dated Oct. 21, 2016, 2 pages.
"Corrected Notice of Allowance", U.S. Appl. No. 14/617,735, dated Jun. 20, 2016, 2 pages.
"Corrected Notice of Allowance", U.S. Appl. No. 14/617,735, dated Jul. 21, 2016, 2 pages.
"Final Office Action", U.S. Appl. No. 14/,447,419, dated Aug. 29, 2016, 11 pages.
"Final Office Action", U.S. Appl. No. 14/617,710, dated Aug. 2, 2016, 19 pages.
"Foreign Office Action", CN Application No. 201380017348.5, dated Jan. 14, 2016, 12 pages.
"International Preliminary Report on Patentability", Application No. PCT/US2015/041930, dated Oct. 26, 2016, 9 pages.
"International Search Report and Written Opinion", Application No. PCT/US2015/054350, dated Feb. 5, 2016, 9 pages.
"Non-Final Office Action", U.S. Appl. No. 13/432,311, dated Aug. 17, 2016, 18 pages.
"Non-Final Office Action", U.S. Appl. No. 14/617,606, dated Sep. 9, 2016, 12 pages.
"Non-Final Office Action", U.S. Appl. No. 14/617,666, dated Jul. 26, 2016, 21 pages.
"Notice of Allowance", U.S. Appl. No. 14/617,574, dated Jul. 20, 2016, 13 pages.
"Notice of Allowance", U.S. Appl. No. 14/617,697, dated Jul. 22, 2016, 5 pages.
"Notice of Allowance", U.S. Appl. No. 14/617,710, dated Oct. 7, 2016, 9 pages.
"Second Written Opinion", Application No. PCT/US2015/041900, dated Jun. 30, 2016, 6 pages.
"Second Written Opinion", Application No. PCT/US2015/041909, dated Jun. 21, 2016, 6 pages.
"Second Written Opinion", Application No. PCT/US2015/041930, dated Jun. 21, 2016, 5 pages.
Mar.,"A Read-Only Distributed Has Table", IN Journal of Grip Computing, vol. 9, Issue 4, Apr. 27, 2011, pp. 501-529.
"Corrected Notice of Allowance", U.S. Appl. No. 14/617,710, dated Dec. 13, 2016, 2 pages.
"Final Office Action", U.S. Appl. No. 14/617,606, dated Dec. 27, 2016, 13 pages.
"Final Office Action", U.S. Appl. No. 14/617,666, dated Dec. 12, 2016, 29 pages.
"Non-Final Office Action", U.S. Appl. No. 14/617,769, dated Jan. 12, 2017, 10 pages.
"Second Written Opinion", Application No. PCT/US2016/015869, dated Jan. 20, 2017, 5 pages.
"Examiner's Answer to Appeal Brief", U.S. Appl. No. 14/447,419, dated Feb. 27, 2017, 8 pages.
"Final Office Action", U.S. Appl. No. 13/229,554, dated Feb. 27, 2015, 29 pages.
"Final Office Action", U.S. Appl. No. 13/229,554, dated Jun. 16, 2016, 35 pages.
"International Preliminary Report on Patentability", Application No. PCT/US2015/041900, dated Oct. 11, 2016, 6 pages.
"International Preliminary Report on Patentability", Application No. PCT/US2015/042187, dated Oct. 31, 2016, 7 pages.
"Non-Final Office Action", U.S. Appl. No. 13/229,554, dated Feb. 3, 2016, 33 pages.
"Non-Final Office Action", U.S. Appl. No. 14/617,666, dated Mar. 22, 2017, 23 pages.
"Non-Final Office Action", U.S. Appl. No. 14/746,298, dated Aug. 28, 2015, 6 pages.
"Restriction Requirement", U.S. Appl. No. 14/447,446, dated Feb. 9, 2017, 7 pages.
"Second Written Opinion", Application No. PCT/US2016/015496, dated Feb. 9, 2017, 7 pages.
"Second Written Opinion", Application No. PCT/US2016/015871, dated Feb. 6, 2017, 8 pages.
"Second Written Opinion", Application No. PCT/US2016/015873, dated Feb. 6, 2017, 6 pages.
"Second Written Opinion", Application No. PCT/US2016/016028, dated Feb. 3, 2017, 5 pages.
"Second Written Opinion", Application No. PCT/US2016/016241, dated Feb. 9, 2017, 7 pages.
Schrauwen,"Focused-Ion-Beam Fabrication of Slanted Grating Couplers in Silicon-on-Insulator Waveguides", IEEE Photonics Technology Letters, vol. 19, Issue 11, Jun. 1, 2007, 3 pages.
"Ex Parte Quayle Action", U.S. Appl. No. 14/617,769, Jun. 2, 2017, 7 pages.
"International Preliminary Report on Patentability", Application No. PCT/US2016/015871, dated May 15, 2017, 10 pages.
"International Preliminary Report on Patentability", Application No. PCT/US2016/019006, dated Jun. 6, 2017, 11 pages.

(56) References Cited

OTHER PUBLICATIONS

"International Preliminary Report on Patentability", Application No. PCT/US2016/016027, dated May 3, 2017, 8 pages.
"International Preliminary Report on Patentability", Application No. PCT/US2016/015873, dated May 15, 2017, 8 pages.
"International Preliminary Report on Patentability", Application No. PCT/US2016/015496, dated May 4, 2017, 9 pages.
"International Preliminary Report on Patentability", Application No. PCT/US2016/016241, dated May 4, 2017, 9 pages.
"Non-Final Office Action", U.S. Appl. No. 14/447,446, dated Jun. 9, 2017, 15 pages.
"Non-Final Office Action", U.S. Appl. No. 14/617,606, dated Mar. 27, 2017, 14 pages.
"Non-Final Office Action", U.S. Appl. No. 14/670,242, dated Jun. 8, 2017, 26 pages.
"Second Written Opinion", Application No. PCT/US2016/016027, dated Jan. 24, 2017, 5 pages.
"Second Written Opinion", Application No. PCT/US2016/019006, dated Feb. 20, 2017, 9 pages.
Widnall,"Lecture L3—Vectors, Matrices and Coordinate Transformations", 16.07 Dynamics, 2009, 16 pages.
"Second Written Opinion", Application No. PCT/US2016/016029, dated Jan. 20, 2017, 6 pages.
"International Preliminary Report on Patentability", Application No. PCT/US2016/016029, dated Apr. 13, 2017, 9 pages.
"Notice of Allowance", U.S. Appl. No. 14/448,913, Aug. 9, 2017, 10 pages.
"Final Office Action", U.S. Appl. No. No. 14/617,606, Sep. 5, 2017, 15 pages.

* cited by examiner

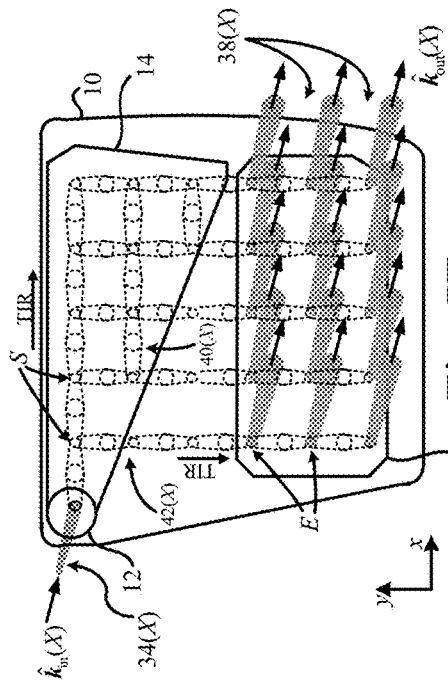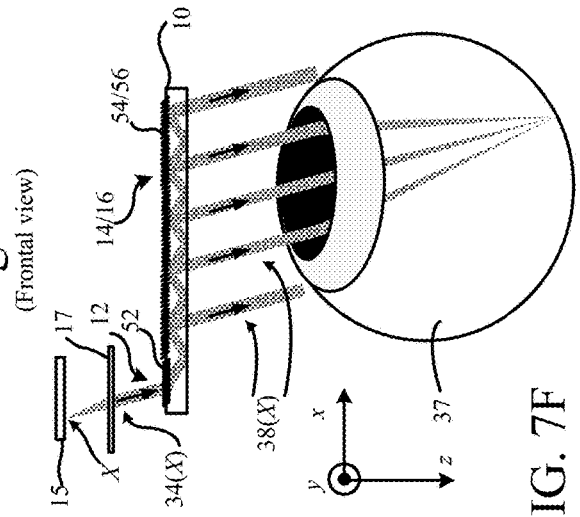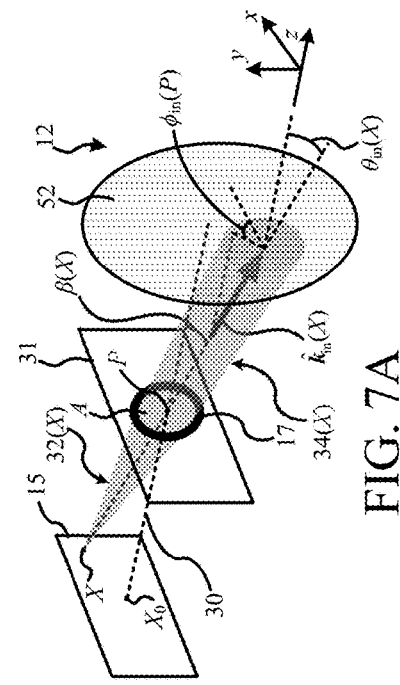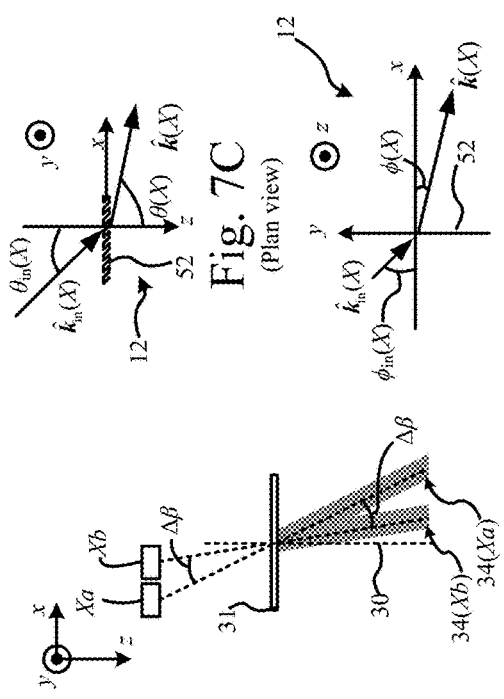

(Plan view)

(Frontal view)

(Frontal view)

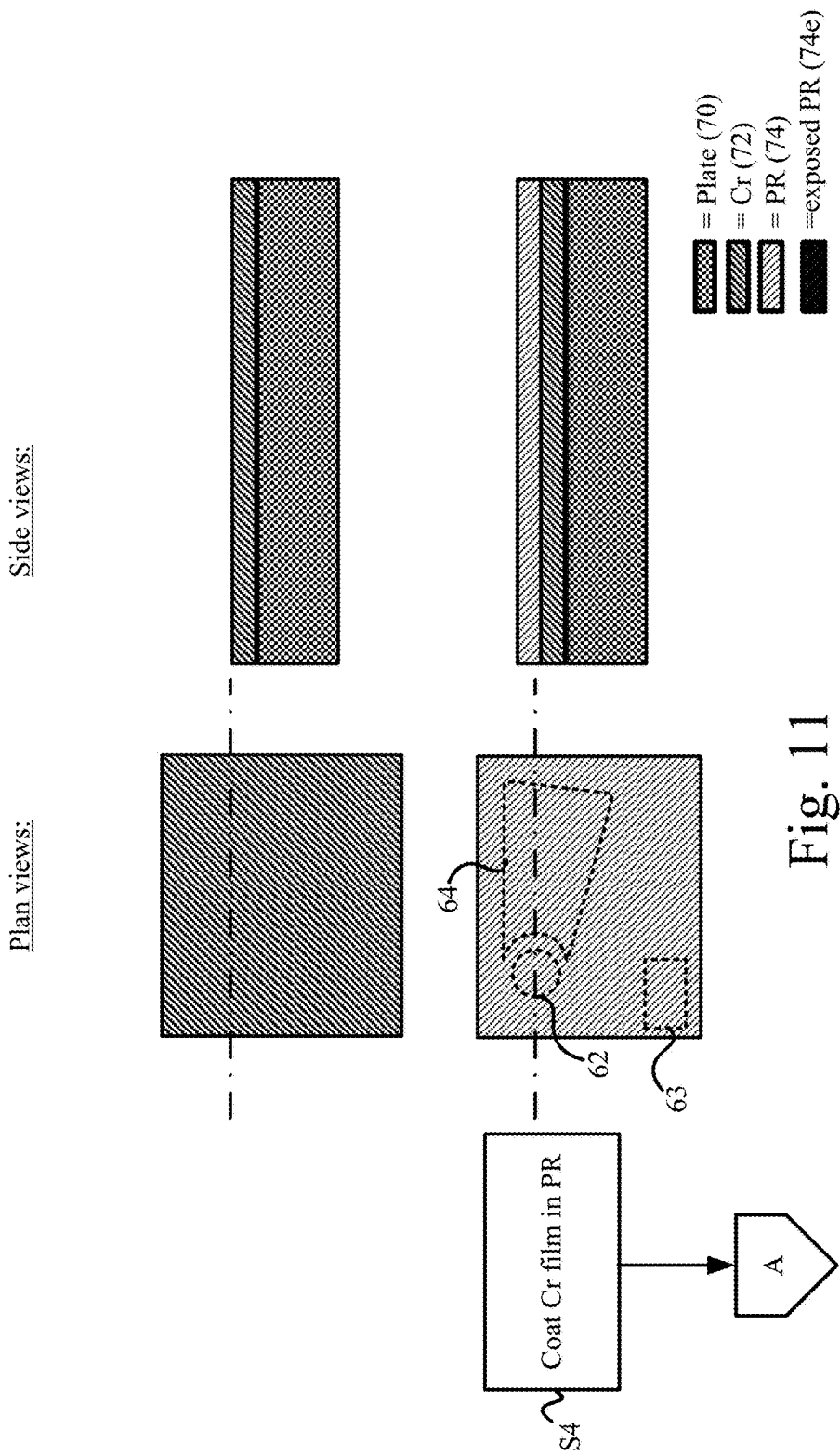

DISPLAY SYSTEM

BACKGROUND

Display systems can used to make a desired image visible to a user (viewer). Wearable display systems can be embodied in a wearable headset which is arranged to display an image within a short distance from a human eye. Such wearable headsets are sometimes referred to as head mounted displays, and are provided with a frame which has a central portion fitting over a user's (wearer's) nose bridge and left and right support extensions which fit over a user's ears. Optical components are arranged in the frame so as to display an image within a few centimeters of the user's eyes. The image can be a computer generated image on a display, such as a micro display. The optical components are arranged to transport light of the desired image which is generated on the display to the user's eye to make the image visible to the user. The display on which the image is generated can form part of a light engine, such that the image itself generates collimated lights beams which can be guided by the optical component to provide an image visible to the user.

Different kinds of optical components have been used to convey the image from the display to the human eye. These can include lenses, mirrors, optical waveguides, holograms and diffraction gratings, for example. In some display systems, the optical components are fabricated using optics that allows the user to see the image but not to see through this optics at the "real world". Other types of display systems provide a view through this optics so that the generated image which is displayed to the user is overlaid onto a real world view. This is sometimes referred to as augmented reality.

Waveguide-based display systems typically transport light from a light engine to the eye via a TIR (Total Internal Reflection) mechanism in a waveguide (light guide). Such systems can incorporate diffraction gratings, which cause effective beam expansion so as to output expanded versions of the beams provided by the light engine. This means the image is visible over a wider area when looking at the waveguide's output than when looking at the light engine directly: provided the eye is within an area such that it can receive some light from substantially all of the expanded beams, the whole image will be visible to the user. Such an area is referred to as an eye box.

To maintain image quality, the structure of the waveguide can be configured in various ways to mitigate distortion of the transported light.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter. Nor is the claimed subject matter limited to implementations that solve any or all of the disadvantages noted in the background section.

According to one aspect a microfabrication process for making an optical component comprises a patterning stage in which one or more portions of a substrate's surface are patterned by performing at least the following steps. At least a region of the substrate's surface is coated in negative photoresist, the region encompassing said portions. The negative photoresist becomes undevelopable when exposed to light. Light which forms a grating structure is projected over each of the portions. Light of substantially uniform intensity is projected over the entirety of the region but for the portions, thereby leaving the negative photoresist outside of the portions undevelopable. The negative photoresist is developed so as to embody the grating structure in the photoresist covering the portions. The substrate's surface is patterned to impose the grating structure on the substrate's surface from the developed photoresist; the undevelopable photoresist inhibits patterning of the surface region outside of the portions. The optical component comprises the patterned substrate.

BRIEF DESCRIPTION OF FIGURES

FIG. 7A shows a perspective view of a part of a display system;
FIG. 7B shows a plan view of individual pixels of a display;
FIGS. 7C and 7D show plan and frontal views of a beam interacting with an optical component;
FIG. 7E shows a frontal view of an optical component performing beam expansion;
FIG. 7F shows a plan (xy) view of an optical component performing beam expansion.

DETAILED DESCRIPTION

Figure 1:
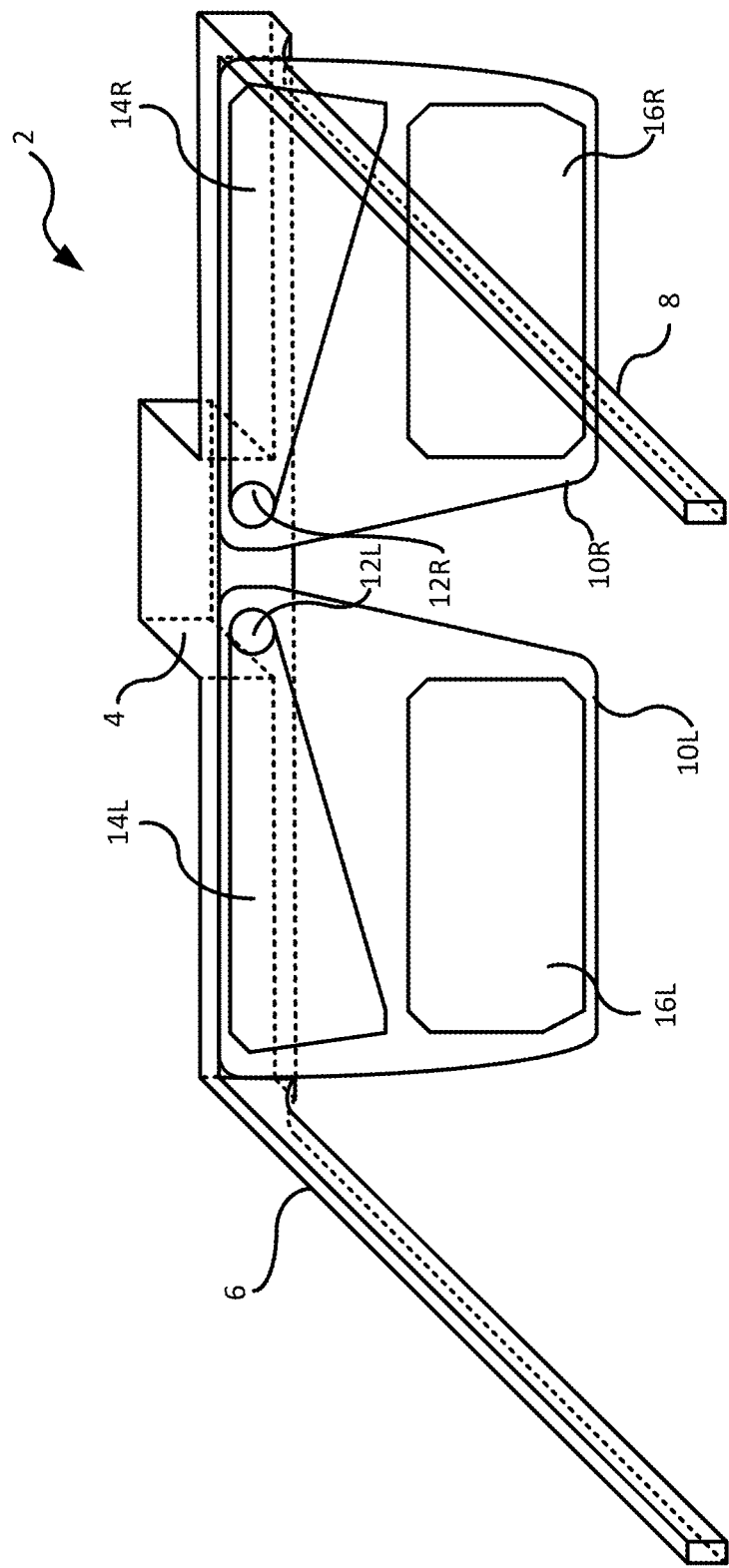
FIG. 1 shows a wearable display system.

FIG. 1 is a perspective view of a head mounted display. The head mounted display comprises a headpiece, which comprises a frame 2 having a central portion 4 intended to fit over the nose bridge of a wearer, and a left and right supporting extension 6,8 which are intended to fit over a user's ears. Although the supporting extensions are shown to be substantially straight, they could terminate with curved parts to more comfortably fit over the ears in the manner of conventional spectacles.

Figure 2A:
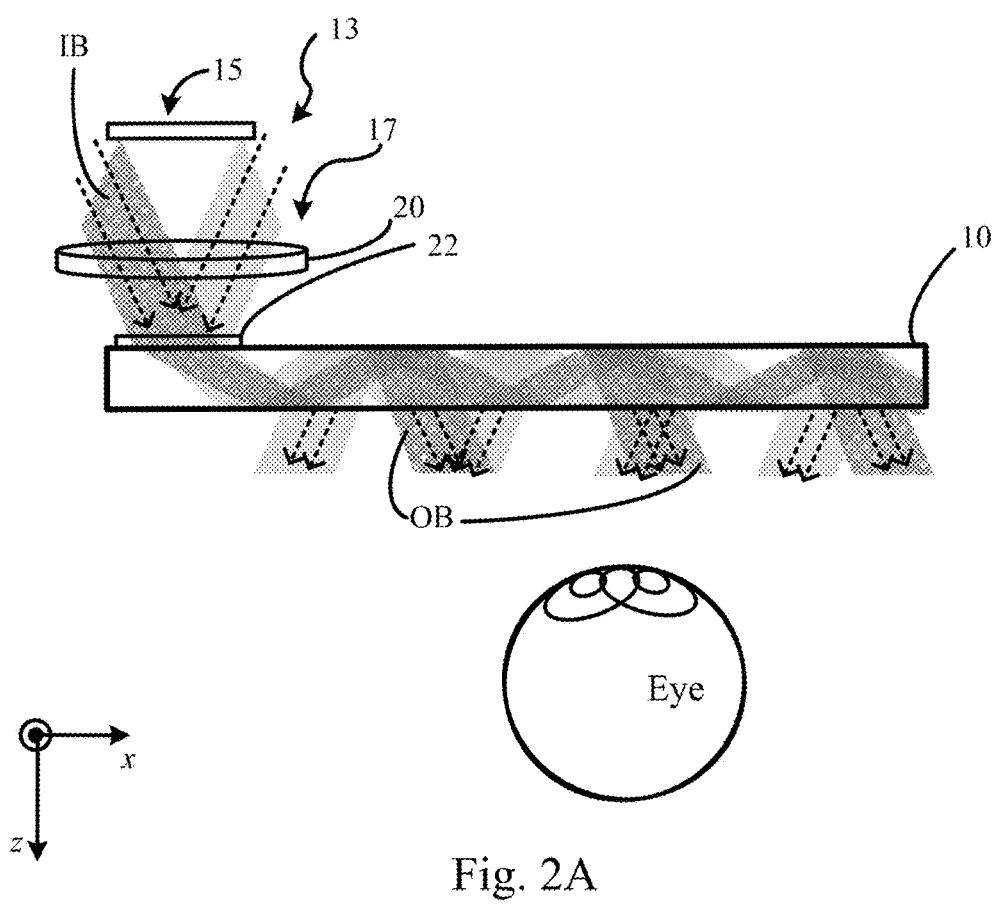
FIG. 2A shows a plan view of part of the display system.

The frame 2 supports left and right optical components, labelled 10L and 10R, which are waveguides. For ease of reference herein an optical component 10 (optical waveguide 10) will be considered to be either a left or right component, because the components are essentially identical apart from being mirror images of each other. Therefore, all description pertaining to the left-hand component also pertains to the right-hand component. The optical components will be described in more detail later with reference to FIG. 3. The central portion 4 houses a light engine which is not shown in FIG. 1 but which is shown in FIG. 2.

FIG. 2 shows a plan view of a section of the top part of the frame of FIG. 1. Thus, FIG. 2 shows the light engine 13 which comprises a micro display 15 and imaging optics 17 in the form of a collimating lens 20. The light engine also includes a processor which is capable of generating an image for the micro display. The micro display can be any type of image source, such as liquid crystal on silicon (LCOS) displays, transmissive liquid crystal displays (LCD), matrix arrays of LED's (whether organic or inorganic) and any other suitable display. The display is driven by circuitry which is not visible in FIG. 2 which activates individual pixels of the display to generate an image. The substantially collimated light, from each pixel, falls on an exit pupil 22 of the light engine 13. At exit pupil 22, collimated light beams are coupled into each optical component, 10L, 10R into a respective in-coupling zone 12L, 12R provided on each component. These in-coupling zones are clearly shown in FIG. 1, but are not readily visible in FIG. 2. In-coupled light is then guided, through a mechanism that involves diffraction and TIR, laterally of the optical component in a respective intermediate (fold) zone 14L, 14R, and also downward into a respective exit zone 16L, 16R where it exits the component 10 towards the users' eye. The zones 14L, 14R, 16L and 16R are shown in FIG. 1. These mechanisms are described in detail below. FIG. 2 shows a user's eye (right or left) receiving the diffracted light from an exit zone (16L or 16R). The output beam OB to a user's eye is parallel with the incident beam IB. See, for example, the beam marked IB in FIG. 2 and two of the parallel output beams marked OB in FIG. 2. The optical component 10 is located between the light engine 13 and the eye i.e. the display system configuration is of so-called transmissive type.

Other headpieces are also within the scope of the subject matter. For instance, the display optics can equally be attached to the users head using a head band, helmet or other fit system. The purpose of the fit system is to support the display and provide stability to the display and other head borne systems such as tracking systems and cameras. The fit system will also be designed to meet user population in anthropometric range and head morphology and provide comfortable support of the display system.

Beams from the same display 15 may be coupled into both components 10L, 10R so that an image is perceived by both eyes from a single display, or separate displays may be used to generate different images for each eye e.g. to provide a stereoscopic image. In alternative headsets, light engine(s) may be mounted at one or both of left and right portions of the frame—with the arrangement of the incoupling, fold and exit zones 12, 14, 16 flipped accordingly.

The optical component 10 is substantially transparent such that a user can not only view the image from the light engine 13, but also can view a real world view through the optical component 10.

The optical component 10 has a refractive index n which is such that total internal reflection takes place guiding the beam from the incoupling zone along the intermediate expansion zone 14, and down towards the exit zone 16.

Figure 3A:
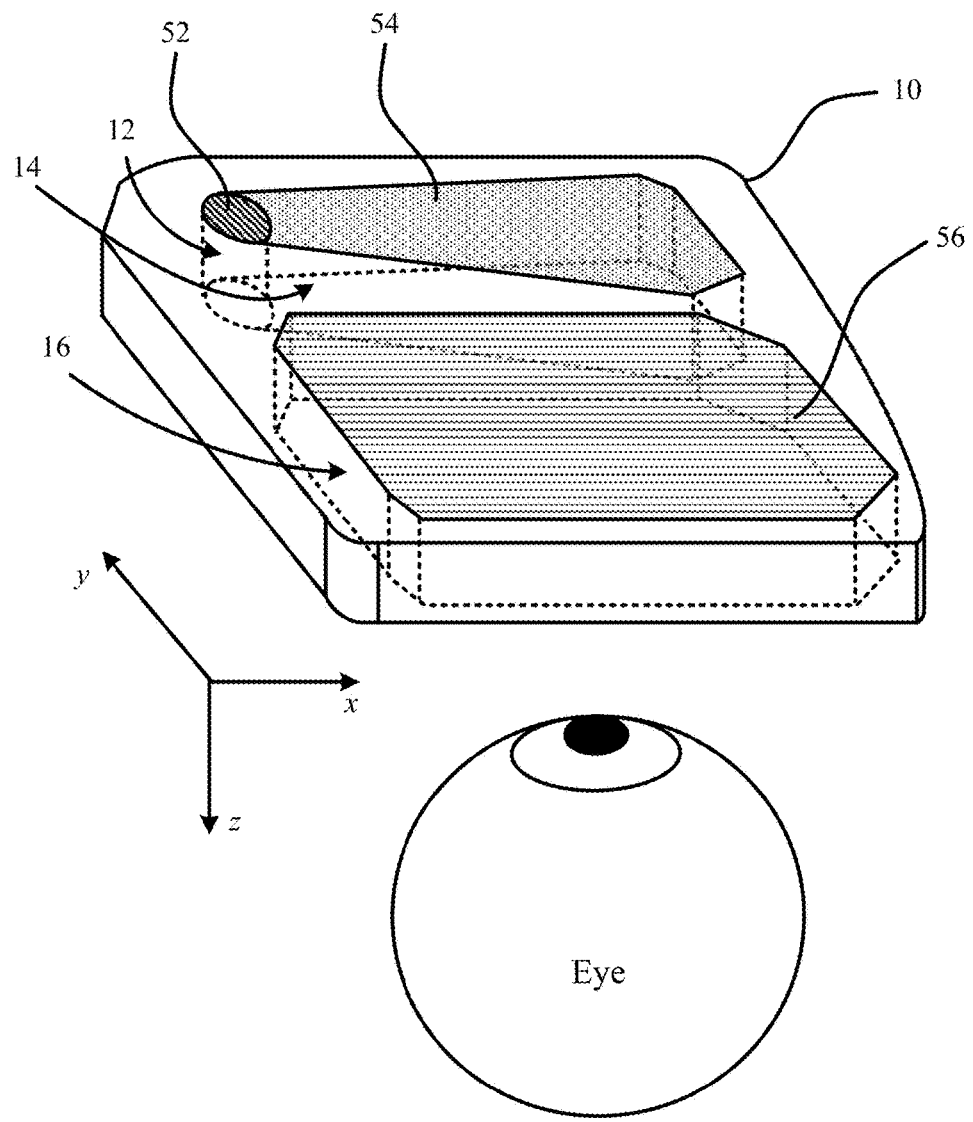
FIGS. 3A and 3B shows perspective and frontal view of an optical component.
Figure 3B:
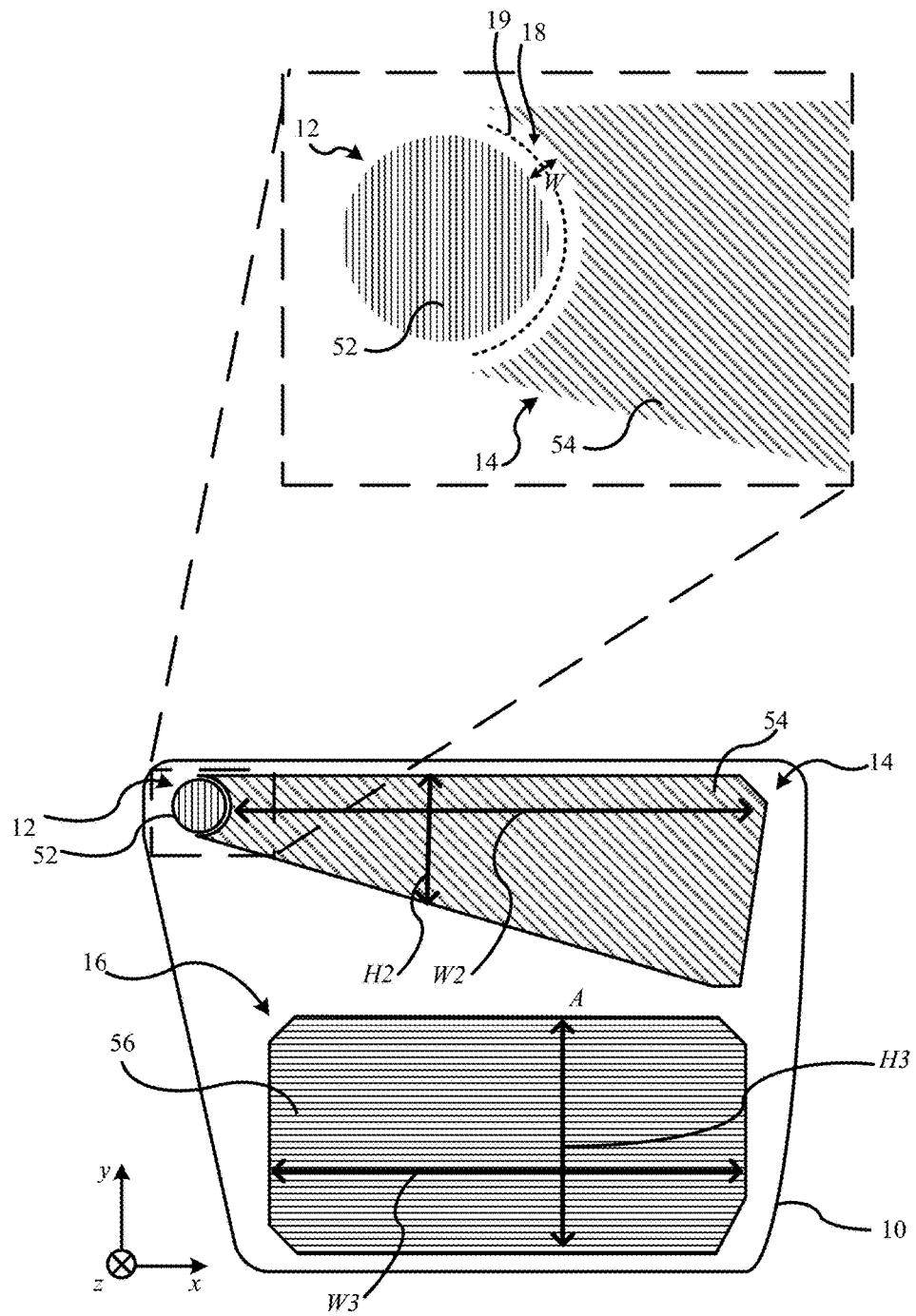

FIGS. 3A and 3B show an optical component in more detail.

FIG. 3A shows a perspective view of an optical component 10. The optical component is flat in that the front and rear portions of its surface are substantially flat (front and rear defined from the viewpoint of the wearer, as indicated by the location of the eye in FIG. 3A). The front and rear portions of the surface are parallel to one another. The optical component 10 lies substantially in a plane (xy-plane), with the z axis (referred to as the "normal") directed towards the viewer from the optical component 10. The incoupling, fold and exit zones 12, 14 and 16 are shown, each defined by respective surface modulations 52, 46 and 56 on the surface of the optical component, which are on the rear of the waveguide from a viewpoint of the wearer. Each of the surface modulations 52, 46, 56 forms a respective surface relief grating (SRG), the nature of which will be described shortly. Instead of the SRGs, holograms could be used which provide the same optical function as the SRGs.

As shown in the plan view of FIG. 3B, the fold zone has a horizontal extent W2 (referred to herein as the "width" of the expansion zone) in the lateral (x) direction and a vertical extent H2 (referred to herein as the "height" of the expansion zone) in the y direction which increases from the inner edge of the optical component to its outer edge in the lateral direction along its width W2. The exit zone has a horizontal extent W3 (width of the exit zone) and vertical extent H3 (height of the exit zone) which define the size of the eye box, which size is independent of the imaging optics in the light engine. The incoupling and fold SRGs 52, 54 have a relative orientation angle A, as do the fold and exit SRGs 54, 56 (note the various dotted lines superimposed on the SRGs 52, 54, 56 denote directions perpendicular to the grating lines of those SRGs).

Principles of the diffraction mechanisms which underlie operation of the head mounted display described herein will now be described with reference to FIGS. 4A and 4B.

The optical components described herein interact with light by way of reflection, refractions and diffraction. Diffraction occurs when a propagating wave interacts with a structure, such as an obstacle or slit. Diffraction can be described as the interference of waves and is most pronounced when that structure is comparable in size to the wavelength of the wave. Optical diffraction of visible light is due to the wave nature of light and can be described as the interference of light waves. Visible light has wavelengths between approximately 390 and 700 manometers (nm) and diffraction of visible light is most pronounced when propagating light encounters structures of a similar scale e.g. of order 100 or 1000 nm in scale.

One example of a diffractive structure is a periodic (substantially repeating) diffractive structure. Herein, a "diffraction grating" means any (part of) an optical component which has a periodic diffractive structure. Periodic structures can cause diffraction of light, which is typically most pronounced when the periodic structure has a spatial period of similar size to the wavelength of the light. Types of periodic structures include, for instance, surface modulations on the surface of an optical component, refractive index modulations, holograms etc. When propagating light encounters the periodic structure, diffraction causes the light to be split into multiple beams in different directions. These directions depend on the wavelength of the light thus diffractions gratings cause dispersion of polychromatic (e.g. white) light, whereby the polychromatic light is split into different coloured beams travelling in different directions.

When the periodic structure is on the surface of an optical component, it is referred to a surface grating. When the periodic structure is due to modulation of the surface itself, it is referred to as a surface relief grating (SRG). An example of a SRG is uniform straight grooves in a surface of an optical component that are separated by uniform straight groove spacing regions. Groove spacing regions are referred to herein as "lines", "grating lines" and "filling regions". The nature of the diffraction by a SRG depends both on the wavelength of light incident on the grating and various optical characteristics of the SRG, such as line spacing, groove depth and groove slant angle. An SRG can be fabricated by way of a suitable microfabrication process, which may involve etching of and/or deposition on a substrate to fabricate a desired periodic microstructure on the substrate to form an optical component, which may then be used as a production master such as a mould for manufacturing further optical components.

An SRG is an example of a Diffractive Optical Element (DOE). When a DOE is present on a surface (e.g. when the DOE is an SRG), the portion of that surface spanned by that DOE is referred to as a DOE area.

Figure 4A:
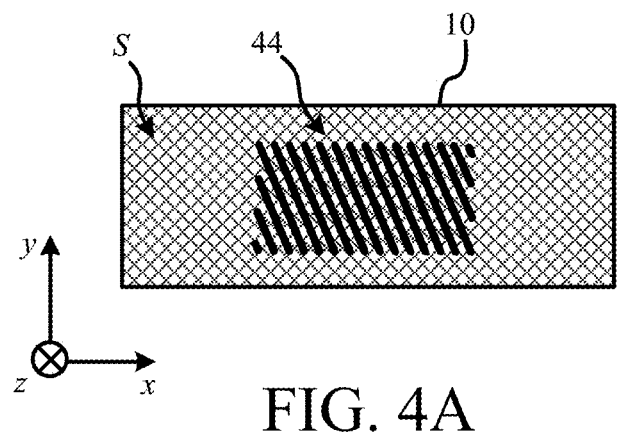
FIG. 4A shows a schematic plan view of an optical component having a surface relief grating formed on its surface.
Figure 4B:
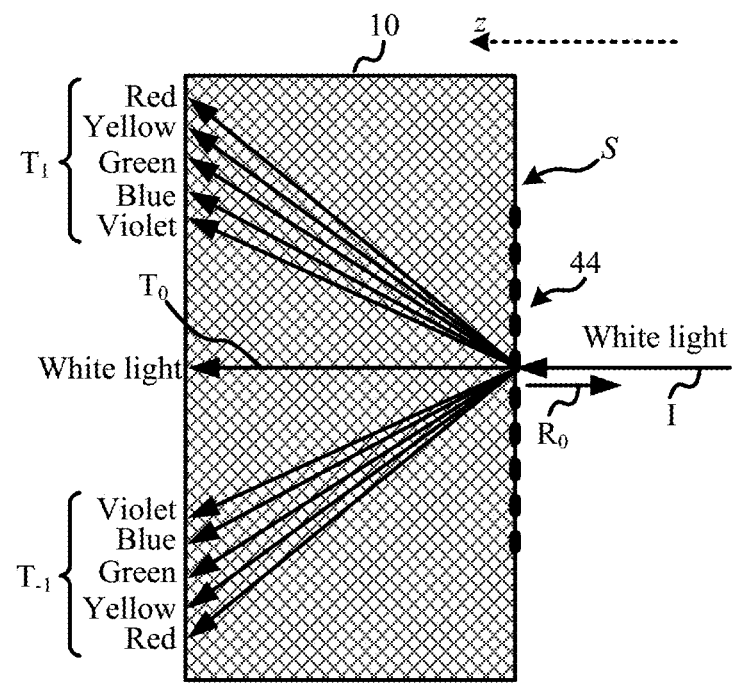
FIG. 4B shows a schematic illustration of the optical component of FIG. 4A, shown interacting with incident light and viewed from the side.

FIGS. 4A and 4B show from the top and the side respectively part of a substantially transparent optical component 10 having an outer surface S. At least a portion of the surface S exhibits surface modulations that constitute a SRG 44 (e.g. 52, 54, 56), which is a microstructure. Such a portion is referred to as a "grating area". The modulations comprise grating lines which are substantially parallel and elongate (substantially longer than they are wide), and also substantially straight in this example (though they need not be straight in general).

FIG. 4B shows the optical component 10, and in particular the SRG 44, interacting with an incoming illuminating light beam I that is inwardly incident on the SRG 44. The light I is white light in this example, and thus has multiple colour components. The light I interacts with the SRG 44 which splits the light into several beams directed inwardly into the optical component 10. Some of the light I may also be reflected back from the surface S as a reflected beam R0. A zero-order mode inward beam T0 and any reflection R0 are created in accordance with the normal principles of diffraction as well as other non-zero-order (±n-order) modes (which can be explained as wave interference). FIG. 4B shows first-order inward beams T1, T−1; it will be appreciated that higher-order beams may or may not also be created depending on the configuration of the optical component 10. Because the nature of the diffraction is dependent on wavelength, for higher-order modes, different colour components (i.e. wavelength components) of the incident light I are, when present, split into beams of different colours at different angles of propagation relative to one another as illustrated in FIG. 4B.

Figure 5A:
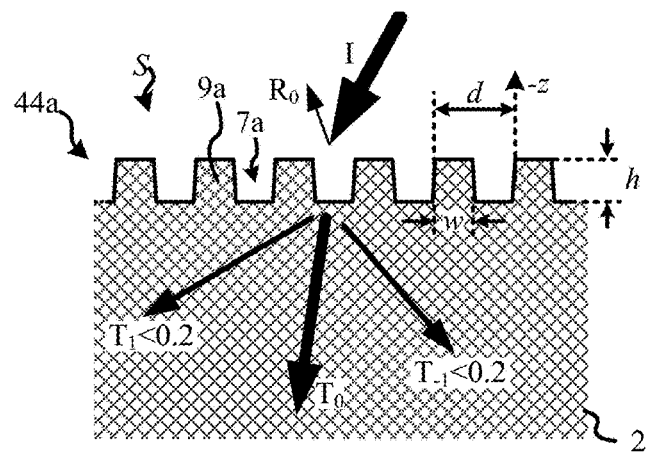
FIG. 5A shows a schematic illustration of a straight binary surface relief grating, shown interacting with incident light and viewed from the side.
Figure 5B:
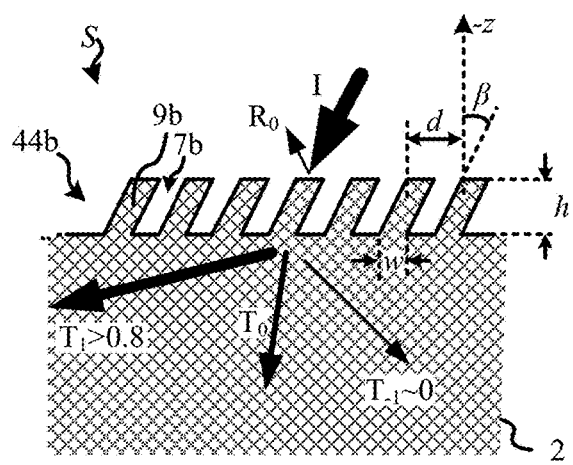
FIG. 5B shows a schematic illustration of a slanted binary surface relief grating, shown interacting with incident light and viewed from the side.
Figure 5C:
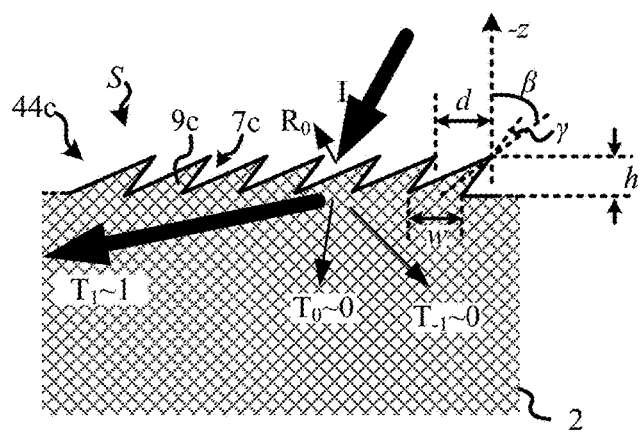
FIG. 5C shows a schematic illustration of an overhanging triangular surface relief grating, shown interacting with incident light and viewed from the side.

FIGS. 5A-5C are close-up schematic cross sectional views of different exemplary SRGs 44a-44c (collectively referenced as 44 herein) that may be formed by modulation of the surface S of the optical component 10 (which is viewed from the side in these figures). Light beams are denoted as arrows whose thicknesses denote approximate relative intensity (with higher intensity beams shown as thicker arrows).

FIG. 5A shows an example of a straight binary SRG 44a. The straight binary SRG 44a is formed of a series of grooves 7a in the surface S separated by protruding groove spacing regions 9a which are also referred to herein as "filling regions", "grating lines" or simply "lines". The SRG 44a has a spatial period of d (referred to as the "grating period"), which is the distance over which the modulations' shape repeats and which is thus the distance between adjacent lines/grooves. The grooves 7a have a depth h and have substantially straight walls and substantially flat bases. The filling regions have a height h and a width that is substantially uniform over the height h of the filling regions, labelled "w" in FIG. 2A (with w being some fraction f of the period: w=f*d).

For a straight binary SRG, the walls are substantially perpendicular to the surface S. For this reason, the SRG 44a causes symmetric diffraction of incident light I that is entering perpendicularly to the surface, in that each +n-order mode beam (e.g. T1) created by the SRG 4a has substantially the same intensity as the corresponding −n-order mode beam (e.g. T−1), typically less than about one fifth (0.2) of the intensity of the incident beam I.

FIG. 5B shows an example of a slanted binary SRG 44b. The slanted binary SRG 44b is also formed of grooves, labelled 7b, in the surface S having substantially straight walls and substantially flat bases separated by lines 9b of width w. However, in contrast to the straight SRG 44a, the walls are slanted by an amount relative to the normal, denoted by the angle β in FIG. 25B. The grooves 7b have a depth h as measured along the normal. Due to the asymmetry introduced by the non-zero slant, ±n-order mode inward beams travelling away from the slant direction have greater intensity that their ∓n-order mode counterparts (e.g. in the example of FIG. 2B, the T1 beam is directed away from the direction of slant and has usually greater intensity than the T−1 beam, though this depends on e.g. the grating period d); by increasing the slant by a sufficient amount, those ∓n counterparts can be substantially eliminated (i.e. to have substantially zero intensity). The intensity of the T0 beam is typically also very much reduced by a slanted binary SRG such that, in the example of FIG. 5B, the first-order beam T1 typically has an intensity of at most about four fifths (0.8) the intensity of the incident beam I.

The binary SRGs 44a and 44b can be viewed as spatial waveforms embedded in the surface S that have a substantially square wave shape (with period d). In the case of the SRG 44b, the shape is a skewed square wave shape skewed by β.

FIG. 5C shows an example of an overhanging triangular SRG 44c which is a special case of an overhanging trapezoidal SRG. The triangular SRG 44c is formed of grooves 7c in the surface S that are triangular in shape (and which thus have discernible tips) and which have a depth h as measured along the normal. Filling regions 9c take the form of triangular, tooth-like protrusions (teeth), having medians that make an angle β with the normal (β being the slant angle of the SRG 44c). The teeth have tips that are separated by d (which is the grating period of the SRG 44c), a width that is w at the base of the teeth and which narrows to substantially zero at the tips of the teeth. For the SRG of FIG. 44c, w≈d, but generally can be w<d. The SRG is overhanging in that the tips of the teeth extend over the tips of the grooves. It is possible to construct overhanging triangular SRGs that substantially eliminate both the transmission-mode T0 beam and the ∓n-mode beams, leaving only ±n-order mode beams (e.g. only T1). The grooves have walls which are at an angle γ to the median (wall angle).

The SRG 44c can be viewed as a spatial waveform embedded in S that has a substantially triangular wave shape, which is skewed by β.

Other SRGs are also possible, for example other types of trapezoidal SRGs (which may not narrow in width all the way to zero), sinusoidal SRGs etc. Such other SRGs also exhibit depth h, linewidth w, slant angle β and wall angles γ which can be defined in a similar manner to FIG. 5A-C.

In the present display system, d is typically between about 250 and 500 nm, and h between about 30 and 400 nm. The slant angle β is typically between about 0 and 45 degrees (such that slant direction is typically elevated above the surface S by an amount between about 45 and 90 degrees).

An SRG has a diffraction efficiency defined in terms of the intensity of desired diffracted beam(s) (e.g. T1) relative to the intensity of the illuminating beam I, and can be expressed as a ratio η of those intensities. As will be apparent from the above, slanted binary SRGs can achieve higher efficiency (e.g. 4b—up to η≈0.8 if T1 is the desired beam) than non-slanted SRGs (e.g. 44a—only up to about η≈0.2 if T1 is the desired beam). With overhanging triangular SRGs, it is possible to achieve near-optimal efficiencies of η≈1.

Returning to FIGS. 3A and 3B, it can be seen that the incoupling, fold and exit zones 12, 14, 16 are diffraction gratings whose periodic structure arises due to the modulations 52, 54, 56 of the optical component's surface that form the incoupling, fold and exit SRGs respectively, and which cover the incoupling, fold and exit zones 12, 14, 16 respectively.

Figure 6:
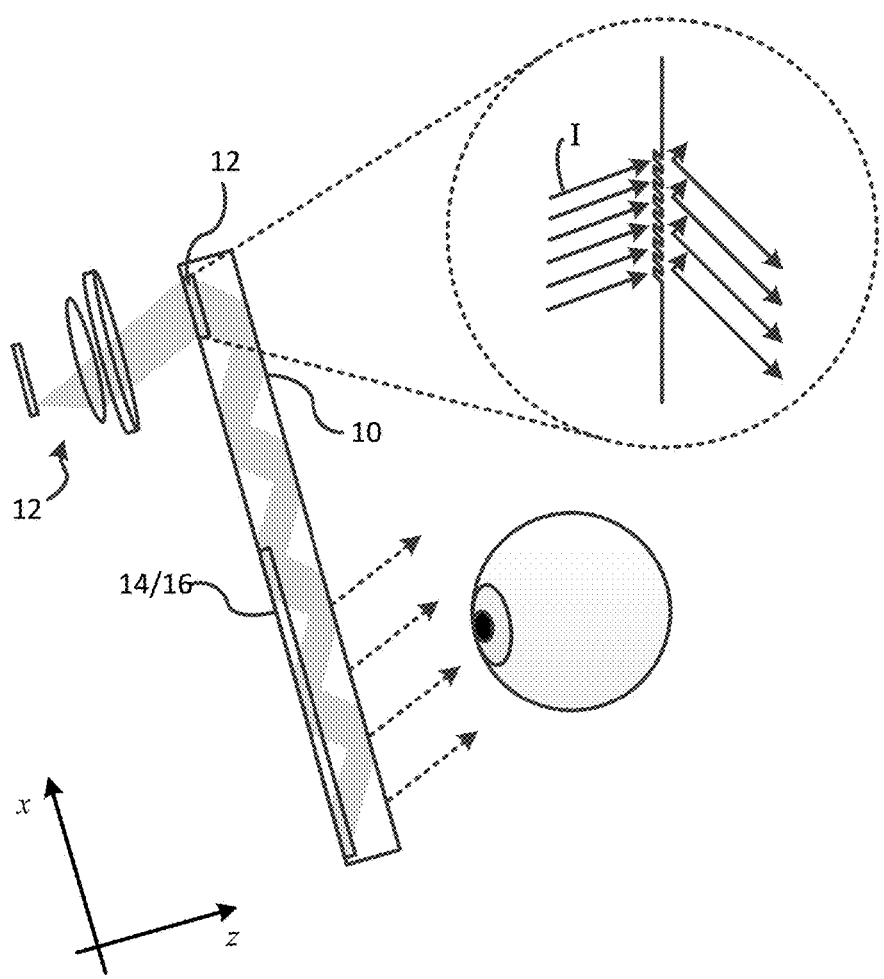
FIG. 6 shows a close up view of part of an incoupling zone of an optical component.

FIG. 6 shows the incoupling SRG 52 with greater clarity, including an expanded version showing how the light beam interacts with it. FIG. 6 shows a plan view of the optical component 10. The light engine 13 provides beams of collimated light, one of which is shown (corresponding to a display pixel). That beam falls on the incoupling SRG 52 and thus causes total internal reflection of the beam in the component 10. The intermediate grating 14 directs versions of the beams down to the exit grating 16, which causes diffraction of the image onto the user's eye. The operation of the grating 12 is shown in more detail in the expanded portion which shows rays of the incoming light beam coming in from the left and denoted I and those rays being diffracted so as to undergo TIR in the optical component 10. The grating in FIG. 6 is of the type shown in FIG. 5B but could also be of the type shown in FIG. 5C or some other slanted grating shape.

Optical principles underlying certain embodiments will now be described with reference to FIGS. 7A-9B.

FIG. 7a shows a perspective view of the display 15, imaging optics 17 and incoupling SRG 52. Different geometric points on the region of the display 15 on which an image is displayed are referred to herein as image points, which may be active (currently emitting light) or inactive (not currently emitting light). In practice, individual pixels can be approximated as image points.

The imaging optics 17 can typically be approximated as a principal plane (thin lens approximation) or, in some cases, more accurately as a pair of principal planes (thick lens approximation) the location(s) of which are determined by the nature and arrangement of its constituent lenses. In these approximations, any refraction caused by the imaging optics 17 is approximated as occurring at the principal plane(s). To avoid unnecessary complication, principles of various embodiments will be described in relation to a thin lens approximation of the imaging optics 17, and thus in relation to a single principal plane labelled 31 in FIG. 7a, but it will be apparent that more complex imaging optics that do not fit this approximation still can be utilized to achieve the desired effects.

The imaging optics 17 has an optical axis 30 and a front focal point, and is positioned relative to the optical component 10 so that the optical axis 30 intersects the incoupling SRG 52 at or near the geometric centre of the incoupling SRG 52 with the front focal point lying substantially at an image point $X_0$ on the display (that is, lying in the same plane as the front of the display). Another arbitrary image point X on the display is shown, and principles underlying various embodiments will now be described in relation to X without loss of generality. In the following, the terminology "for each X" or similar is used as a convenient shorthand to mean "for each image point (including X)" or similar, as will be apparent in context.

When active, image points—including the image point labelled X and $X_0$—act as individual illumination point sources from which light propagates in a substantially isotropic manner through the half-space forward of the display 15. Image points in areas of the image perceived as lighter emit light of higher intensity relative to areas of the image perceived as darker. Image points in areas perceived as black emit no or only very low intensity light (inactive image points). The intensity of the light emitted by a particular image point may change as the image changes, for instance when a video is displayed on the display 15.

Each active image point provides substantially uniform illumination of a collimating area A of the imaging optics 17, which is substantially circular and has a diameter D that depends on factors such as the diameters of the constituent lenses (D may be of order 1-10 mm, but this is just an example). This is illustrated for the image point X in FIG. 7a, which shows how any propagating light within a cone 32(X) from X is incident on the collimating area A. The imaging optics collimates any light 32(X) incident on the collimating area A to form a collimated beam 34(X) of diameter D (input beam), which is directed towards the incoupling grating 52 of the optical component 10. The beam 34(X) is thus incident on the incoupling grating 52. A shielding component (not shown) may be arranged to prevent any un-collimated light from outside of the cone 32(X) that is emitted from X from reaching the optical component 10.

The beam 34(X) corresponding to the image point X is directed in an inward propagation direction towards the incoupling SRG 52, which can be described by a propagation vector $\hat{k}_{in}(X)$ (herein, bold typeface is used to denote 3-dimensional vectors, with hats on such vectors indicating denoting a unit vector). The inward propagation direction depends on the location of X in the image and, moreover, is unique to X. That unique propagation direction can be parameterized in terms of an azimuthal angle $\phi_{in}(X)$ (which is the angle between the x-axis and the projection of $\hat{k}_{in}(X)$ in the xy-plane) and a polar angle $\theta_{in}(X)$ (which is the angle between the z-axis and $\hat{k}_{in}(P)$ as measured in the plane in which both the z-axis and $\hat{k}_{in}(X)$ lie—note this is not the xz-plane in general). The notation $\phi_{in}(X)$, $\theta_{in}(X)$ is adopted to denote the aforementioned dependence on X; as indicated $\phi_{in}(X)$, $\theta_{in}(X)$ are unique to that X. Note that, herein, both such unit vectors and such polar/azimuthal angle pairs parameterizing such vectors are sometimes referred herein to as "directions" (as the latter represent complete parameterizations thereof), and that sometimes azimuthal angles are referred to in isolation as xy-directions for the same reason. Note further that "inward" is used herein to refer to propagation that is towards the waveguide (having a positive z-component when propagation is towards the rear of the waveguide as perceived by the viewer and a negative z-component when propagation is towards the front of the waveguide).

The imaging optics has a principle point P, which is the point at which the optical axis 30 intersects the principal plane 31 and which typically lies at or near the centre of the collimation area A. The inward direction $\hat{k}_{in}(X)$ and the optical axis 30 have an angular separation $\beta(X)$ equal to the angle subtended by X and $X_0$ from P. $\beta(X)=\theta_{in}(X)$ if the optical axis is parallel to the z-axis (which is not necessarily the case).

As will be apparent, the above applies for each active image point and the imaging optics is thus arranged to substantially collimate the image which is currently on the display 15 into multiple input beams, each corresponding to and propagating in a unique direction determined by the location of a respective active image point (active pixel in practice). That is, the imaging optics 17 effectively converts each active point source X into a collimated beam in a unique inward direction $\hat{k}_{in}(X)$. As will be apparent, this can be equivalently stated as the various input beams for all the active image points forming a virtual image at infinity that corresponds to the real image that is currently on the display 17. A virtual image of this nature is sometimes referred to herein as a virtual version of the image (or similar).

The input beam corresponding to the image point $X_0$ (not shown) would propagate parallel to the optical axis 30, towards or near the geometric centre of the incoupling SRG 52.

As mentioned, in practice, individual pixels of the display 15 can be approximated as single image points. This is illustrated in FIG. 7B which is a schematic plan view showing the principal plane 31 and two adjacent pixels Xa, Xb of the display 15, whose centres subtend an angle $\Delta\beta$ from the principal point P. Light emitted the pixels Xa, Xb when active is effectively converted into collimated beams 34(Xa), 34(Xb) having an angular separation equal to $\Delta\beta$. As will be apparent, the scale of the pixels Xa, Xb has been greatly enlarged for the purposes of illustration.

The beams are highly collimated, having an angular range no greater than the angle subtended by an individual pixel from P ($\sim\Delta\beta$) e.g. typically having an angular range no more than about ½ milliradian. As will become apparent in view of the following, this increases the image quality of the final image as perceived by the wearer.

FIGS. 7C and 7D show schematic plan (xz) and frontal (yz) views of part of the optical component respectively. As indicated in these figures, the incoupling grating 52 causes diffraction of the beam 34(X) thereby causing a first (±1) order mode beam to propagate within the optical component 10 in a new direction $\hat{k}(X)$ that is generally towards the fold SRG 54 (i.e. that has a positive x-component). The new direction $\hat{k}(X)$ can be parameterized by azimuthal and polar angles $\phi(X)$—where $|\phi(X)|\leq|\phi_{in}(X)|$ and $\theta(X)$—where $|\theta(X)|>|\theta_{in}(X)|$—which are also determined by the location of and unique to the image point X. The grating 52 is configured so that the first order mode is the only significant diffraction mode, with the intensity of this new beam thus substantially matching that of the input beam. As mentioned above, a slanted grating can be used to achieve this desired effect (the beam as directed away from the incoupling SRG 52 would correspond, for instance, to beam T1 as shown in FIG. 4B or 4C). In this manner, the beam 34(X) is coupled into the incoupling zone 12 of the optical component 10 in the new direction $\hat{k}(X)$.

The optical component has a refractive index n and is configured such that the polar angle $\theta(X)$ satisfies total internal reflection criteria given by:

$$\sin \theta(X) > 1/n \text{ for each } X. \qquad (1):$$

As will be apparent, each beam input from the imaging optics 17 thus propagates through the optical component 10 by way of total internal reflection (TIR) in a generally horizontal (+x) direction (offset from the x-axis by $\phi(X)<\phi_{in}(X)$). In this manner, the beam 34(X) is coupled from the incoupling zone 12 into the fold zone 14, in which it propagates along the width of the fold zone 14.

FIG. 7E shows 10 a frontal (xy) view of the whole of the optical component 10, from a viewpoint similar to that of the wearer. As explained in more detail below, a combination of diffractive beam splitting and total internal reflection within the optical component 10 results in multiple versions of each input beam 34(X) being outwardly diffracted from the exit SRG along both the width and the height of the exit zone 16 as output beams 38(X) in respective outward directions (that is, away from the optical component 10) that substantially match the respective inward direction $\hat{k}_{in}(X)$ of the corresponding input beam 34(X).

In FIG. 7E, beams external to the optical component 10 are represented using shading and dotted lines are used to represent beams within the optical component 10. Perspective is used to indicate propagation in the z-direction, with widening (resp. narrowing) of the beams in FIG. 7E representing propagation in the positive (resp. negative) z direction; that is towards (resp. away from) the wearer. Thus, diverging dotted lines represent beams within the optical component 10 propagating towards the front wall of the optical component 10; the widest parts represent those beams striking the front wall of the optical component 10, from which they are totally internally reflected back towards the rear wall (on which the various SRGs are formed), which is represented by the dotted lines converging from the widest points to the narrowest points at which they are incident on the rear wall. Regions where the various beams are incident on the fold and exit SRGs are labelled S and E and termed splitting and exit regions respectively for reasons that will become apparent.

As illustrated, the input beam 34(X) is coupled into the waveguide by way of the aforementioned diffraction by the incoupling SRG 52, and propagates along the width of the incoupling zone 12 by way of TIR in the direction $\phi(X)$, $\pm\theta(X)$ (the sign but not the magnitude of the polar angle changing whenever the beam is reflected). As will be apparent, this results in the beam 34(X) eventually striking the fold SRG at the left-most splitting region S.

When the beam 34(X) is incident at a splitting region S, that incident beam 34(X) is effectively split in two by way of diffraction to create a new version of that beam 42(X) (specifically a −1 reflection mode beam) which directed in a specific and generally downwards (−y) direction $\phi'(X)$, $\pm\theta'(X)$ towards the exit zone 16 due to the fold SRG 54 having a particular configuration which will be described in due course, in addition to a zero order reflection mode beam (specular reflection beam), which continues to propagate along the width of the beam in the same direction $\phi(X)$, $\pm\theta(X)$ just as the beam 34(X) would in the absence of the fold SRG (albeit at a reduced intensity). Thus, the beam 34(X) effectively continues propagates along substantially the whole width of the fold zone 14, striking the fold SRG at various splitting regions S, with another new version of the beam (in the same specific downward direction ϕ'(X), ±θ'(X)) created at each splitting region S. As shown in FIG. 7E, this results in multiple versions of the beam 34(X) being coupled into the exit zone 16, which are horizontally separated so as to collectively span substantially the width of the exit zone 16.

As also shown in FIG. 7E, a new version 42(X) of the beam as created at a splitting region S may itself strike the fold SRG during its downward propagation. This will result in a zero order mode being created which continues to propagate generally downwards in the direction ϕ'(X), ±θ'(X) and which can be viewed as continued propagation of that beam, but may also result in a non-zero order mode beam 40(X) (further new version) being created by way of diffraction. However, any such beam 40(X) created by way of such double diffraction at the same SRG will propagate in substantially the same direction ϕ(X), ±θ(X) along the width of the fold zone 14 as the original beam 34(X) as coupled into the optical component 10 (see below). Thus, notwithstanding the possibility of multiple diffractions by the fold SRG, propagation of the various versions of the beam 34(X) (corresponding to image point X) within the optical component 10 is effectively limited to two xy-directions: the generally horizontal direction (ϕ(X), ±θ(X)), and the specific and generally downward direction (ϕ'(X), ±θ'(X)) that will be discussed shortly.

Propagation within the fold zone 14 is thus highly regular, with all beam versions corresponding to a particular image point X substantially constrained to a lattice like structure in the manner illustrated.

The exit zone 16 is located below the fold zone 14 and thus the downward-propagating versions of the beam 42(X) are coupled into the exit zone 16, in which they are guided onto the various exit regions E of the output SRG. The exit SRG 56 is configured so as, when a version of the beam strikes the output SRG, that beam is diffracted to create a first order mode beam directed outwardly from the exit SRG 56 in an outward direction that substantially matches the unique inward direction in which the original beam 34(X) corresponding to image point X was inputted. Because there are multiple versions of the beam propagating downwards that are substantially span the width of the exit zone 16, multiple output beams are generated across the width of the exit zone 16 (as shown in FIG. 7E) to provide effective horizontal beam expansion.

Moreover, the exit SRG 56 is configured so that, in addition to the outwardly diffracted beams 38(X) being created at the various exit regions E from an incident beam, a zero order diffraction mode beam continuous to propagate downwards in the same specific direction as that incident beam. This, in turn, strikes the exit SRG at a lower exit zone 16s in the manner illustrated in FIG. 7E, resulting in both continuing zero-order and outward first order beams. Thus, multiple output beams 38(X) are also generated across substantially the height of the exit zone 16 to provide effective vertical beam expansion.

The output beams 38(X) are directed outwardly in outward directions that substantially match the unique input direction in which the original beam 34(X) is inputted. In this context, substantially matching means that the outward direction is related to the input direction in a manner that enables the wearer's eye to focus any combination of the output beams 38(X) to a single point on the retina, thus reconstructing the image point X (see below).

For a flat optical component (that is, whose front and rear surfaces lie substantially parallel to the xy-plane in their entirety), the output beams are substantially parallel to one another (to at least within the angle Δβ subtended by two adjacent display pixels) and propagate outwardly in an output propagation direction $\hat{k}_{out}(X)$ that is parallel to the unique inward direction $\hat{k}_{in}(X)$ in which the corresponding input beam 34(X) was directed to the incoupling SRG 52. That is, directing the beam 34(X) corresponding to the image point X to the incoupling SRG 52 in the inward direction $\hat{k}_{in}(X)$ causes corresponding output beams 38(X) to be diffracted outwardly and in parallel from the exit zone 16, each in an outward propagation direction $\hat{k}_{out}(X)=\hat{k}_{in}(X)$ due to the configuration of the various SRGs (see below).

As will now be described with reference to FIG. 7F, this enables a viewer's eye to reconstruct the image when looking at the exit zone 16. FIG. 7F shows a plan (xz) view of the optical component 10. The input beam 34(X) is in coupled to the optical component 10 resulting in multiple parallel output beams 38(X) being created at the various exit regions E in the manner discussed above. This can be equivalently expressed at the various output beams corresponding to all the image points forming the same virtual image (at infinity) as the corresponding input beams.

Because the beams 38(X) corresponding to the image point X are all substantially parallel, any light of one or more of the beam(s) 38(X) which is received by the eye 37 is focussed as if the eye 37 were perceiving an image at infinity (i.e. a distant image). The eye 37 thus focuses such received light onto a single retina point, just as if the light were being received from the imaging optics 17 directly, thus reconstructing the image point X (e.g. pixel) ion the retina. As will be apparent, the same is true of each active image point (e.g. pixel) so that the eye 37 reconstructs the whole image that is currently on the display 15.

However, in contrast to receiving the image directly from the optics 17—from which only a respective single beam 34(X) of diameter D is emitted for each X—the output beams 39(X) are emitted over a significantly wider area i.e. substantially that of the exit zone 16, which is substantially larger than the area of the inputted beam ($\sim D^2$). It does not matter which (parts) of the beam(s) 38(X) the eye receives as all are focused to the same retina point—e.g., were the eye 37 to be moved horizontally (±x) in FIG. 7F, it is apparent that the image will still be perceived. Thus, no adaptation of the display system is required for, say, viewers with different pupillary distances beyond making the exit zone 16 wide enough to anticipate a reasonable range of pupillary distances: whilst viewers whose eyes are closer together will generally receive light from the side of the exit zone 16 nearer the incoupling zone 12 as compared with viewers whose eyes are further apart, both will nonetheless perceive the same image. Moreover, as the eye 27 rotates, different parts of the image are brought towards the centre of the viewer's field of vision (as the angle of the beams relative to the optical axis of the eye changes) with the image still remaining visible, thereby allowing the viewer to focus their attention on different parts of the image as desired.

The same relative angular separation Δβ exhibited the input beams corresponding any two adjacent pixels Xa, Xb is also exhibited by the corresponding sets of output beams 38(Xa), 38(Xb)—thus adjacent pixels are focused to adjacent retina points by the eye 37. All the various versions of the beam remain highly collimated as they propagate through the optical component 10, preventing significant overlap of pixel images as focused on the retina, thereby preserving image sharpness.

It should be noted that FIGS. 7A-7G are not to scale and that in particular beams diameters are, for the sake of clarity, generally reduced relative to components such as the display 15 than would typically be expected in practice.

The configuration of the incoupling SRG 52 will now be described with reference to FIGS. 8A and 8B, which show schematic plan and frontal views of part of the fold grating 52. Note, in FIGS. 8A and 8B, beams are represented by arrows (that is, their area is not represented) for the sake of clarity.

Figure 8A:
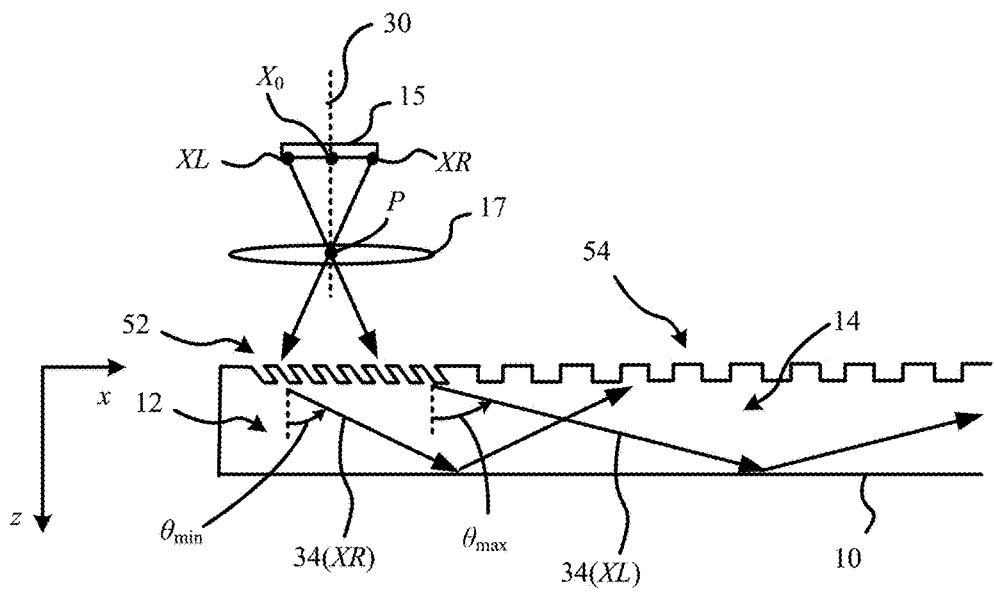
FIGS. 8A and 8B are plan and frontal views of a part of an optical component.

FIG. 8A shows two image points XL, XR located at the far left and far right of the display 15 respectively, from which light is collimated by the optics 17 to generate respective input beams 34(XL), 34(XR) in inward directions $(\theta_{in}(XL), \phi_{in}(XL)), (\phi_{in}(XR), \phi_{in}(XR))$. These beams are coupled into the optical component 10 by the incoupling SRG 52 as shown—the incoupled beams shown created at the incoupling SRG 52 are first order (+1) mode beams created by way of diffraction of the beams incident on the SRG 52. The beams 34(XL), 34(XR) as coupled into the waveguide propagate in directions defined by the polar angles $\theta(XL), \theta(XR)$.

Figure 8B:
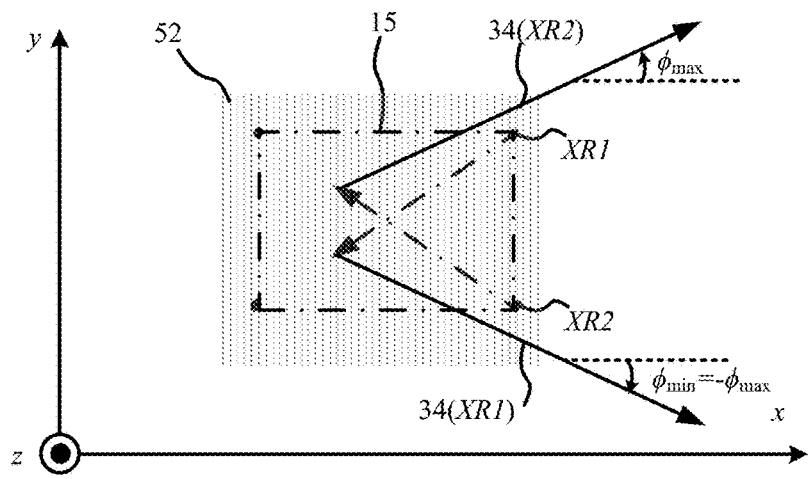

FIG. 8B shows two image points XR1 and XR2 at the far top-right and far bottom-right of the display 15. Note in this figure dashed-dotted lines denote aspects which are behind the optical component 10 (−z). Corresponding beams 34(XL), 34(XR) in directions within the optical component 10 with polar angles $\phi(XL), \phi(XR)$.

Such angles $\theta(X), \phi(X)$ are given by the (transmissive) grating equations:

$$n \sin \theta(X) \sin \phi(X) = \sin \theta_{in}(X) \sin \phi_{in}(X) \qquad (2)$$

$$n \sin \theta(X) \cos \phi(X) = \sin \theta_{in}(X) \cos \phi_{in}(X) + \frac{\lambda}{d_1} \qquad (3)$$

with the SRG 52 having a grating period $d_1$, the beam light having a wavelength $\lambda$, and n the refractive index of the optical component.

It is straightforward to show from (2), (3) that $\theta(XL) = \theta_{max}$ and $\theta(XR) = \theta_{min}$ i.e. that any beam as coupled into the component 10 propagates with an initial polar angle in the range $[\theta(XR), \theta(XL)]$; and that $\phi(XR2) = \phi_{max}$ and $\phi(XR1) = \phi_{min}$ ($\approx -\phi_{max}$ in this example) i.e. that any beam as coupled into the component initially propagates with an azimuthal angle in the range $[\phi(XR1), \phi(XR2)]$ ($\approx [-\phi)(XR2), \phi(XR2)]$).

The configuration of the fold SRG 54 will now be described with references to FIGS. 9A-9B. Note, in FIGS. 9A and 9B, beams are again represented by arrows, without any representation of their areas, for the sake of clarity. In these figures, dotted lines denote orientations perpendicular to the fold SRG grating lines, dashed lines orientations perpendicular to the incoupling SRG grating lines, and dash-dotted lines orientations perpendicular to the exit SRG grating lines.

Figure 9A:
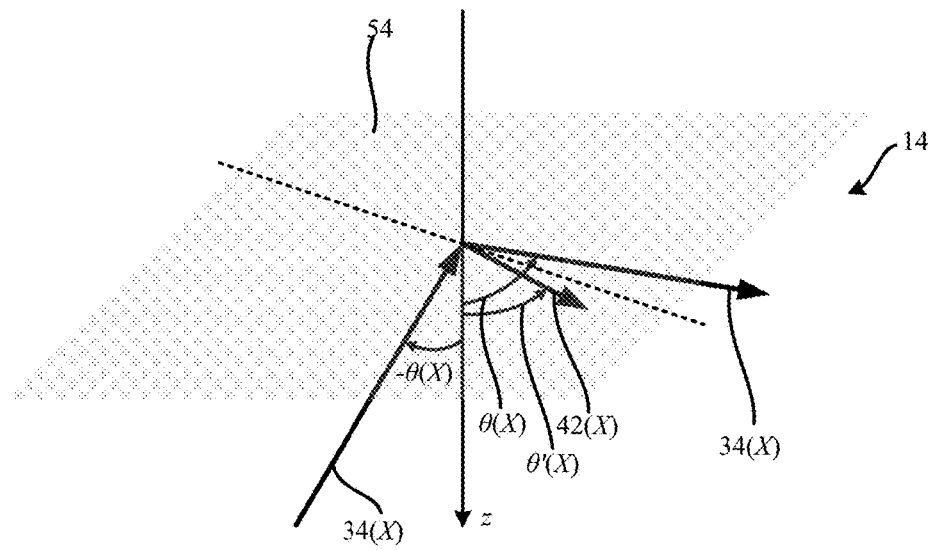
FIG. 9A shows a perspective view of beam reflection within a fold zone of a waveguide.

FIG. 9A shows a perspective view of the beam 34(X) as coupled into the fold zone 14 of the optical component 10, having been reflected from the front wall of the optical component 10 and thus travelling in the direction ($\phi(X)$, $-\theta(X)$) towards the fold SRG 54. A dotted line (which lies perpendicular to the fold SRG grating lines) is shown to represent the orientation of the fold SRG.

The fold SRG 54 and incoupling SRG 52 have a relative orientation angle A (which is the angle between their respective grating lines). The beam thus makes an angle $A+\phi(X)$ (see FIG. 9B) with the fold SRG grating lines as measured in the xy-plane. The beam 34 is incident on the fold SRG 54, which diffracts the beam 34 into different components. A zero order reflection mode (specular reflection) beam is created which continues to propagate in the direction ($\phi(X)$, $+\theta(X)$) just as the beam 34(X) would due to reflection in the absence of the fold SRG 54 (albeit at a reduced intensity). This specular reflection beam can be viewed as effectively a continuation of the beam 34(X) and for this reason is also labelled 34(X). A first order (−1) reflection mode beam 42(X) is also created which can be effectively considered a new version of the beam.

As indicated, the new version of the beam 42(X) propagates in a specific direction ($\phi'(X)$, $\theta'(X)$) which is given by the known (reflective) grating equations:

$$n \sin \theta'(X) \sin(A + \phi'(X)) = n \sin \theta(X) \sin(A + \phi(X)) \qquad (4)$$

$$n \sin \theta'(X) \cos(A + \phi'(X)) = n \sin \theta(X) \cos(A + \phi(X)) - \frac{\lambda}{d_2} \qquad (5)$$

where the fold SRG has a grating period $d_2$, the beam light has a wavelength $\lambda$ and n is the refractive index of the optical component 10.

Figure 9B:
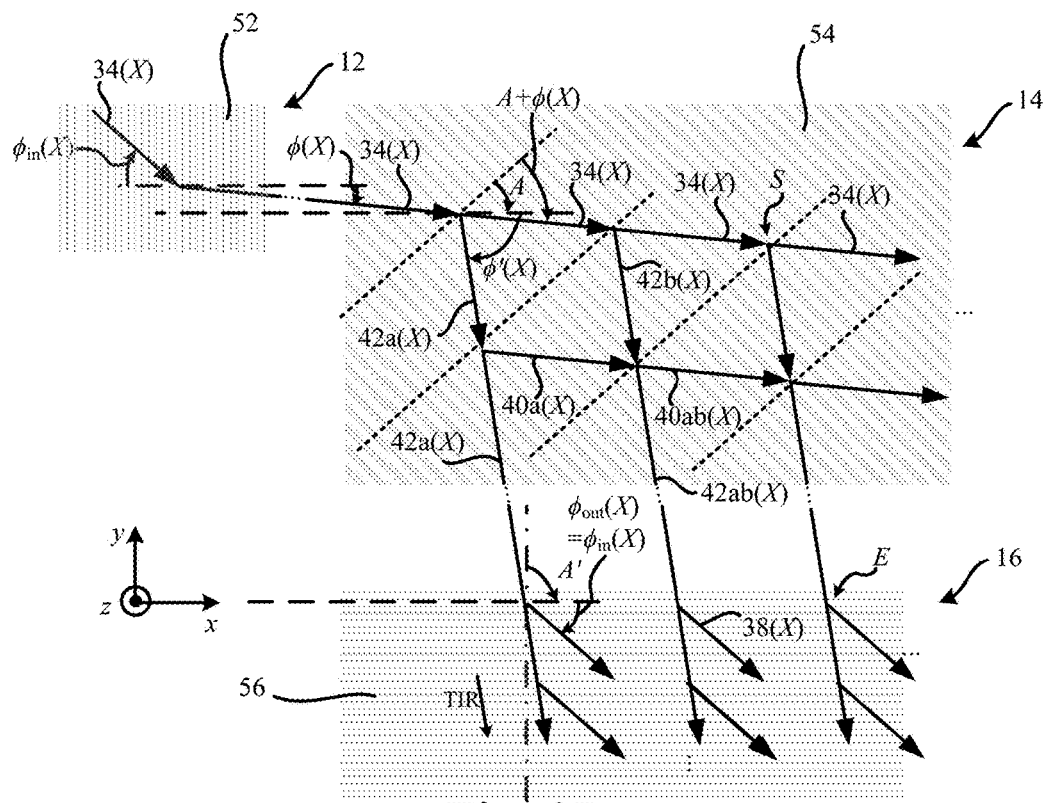
FIG. 9B illustrates a beam expansion mechanism.

As shown in FIG. 9B, which shows a schematic frontal view of the optical component 10, the beam 34(X) is coupled into the incoupling zone 12 with azimuthal angle $\phi(X)$ and thus makes an xy-angle $\phi(X)+A$ the fold SRG 54.

A first new version 42a(X) (−1 mode) of the beam 34(X) is created when it is first diffracted by the fold SRG 54 and a second new version 42b(X) (−1 mode) when it is next diffracted by the fold SRG 54 (and so on), which both propagate in xy-direction $\phi'(X)$. In this manner, the beam 34(X) is effectively split into multiple versions, which are horizontally separated (across the width of the fold zone 14). These are directed down towards the exit zone 16 and thus coupled into the exit zone 16 (across substantially the width of the exit zone 16 due to the horizontal separation). As can be see, the multiple versions are thus incident on the various exit regions (labelled E) of the exit SRG 56, which lie along the width of the exit zone 16.

These new, downward (−y)-propagating versions may themselves meet the fold SRG once again, as illustrated. However, it can be shown from (4), (5) that any first order reflection mode beam (e.g. 40a(X), +1 mode) created by diffraction at an SRG of an incident beam (e.g. 42a(X), −1 mode) which is itself a first order reflection mode beam created by an earlier diffraction of an original beam (e.g. 34(X)) at the same SRG will revert to the direction of the original beam (e.g. $\phi(X)$, $\pm\theta(X)$, which is the direction of propagation of 40a(X)). Thus, propagation within the fold zone 14 is restricted to a diamond-like lattice, as can be seen from the geometry of FIG. 9B. The beam labelled 42ab(X) is a superposition of a specular reflection beam created when 42b(X) meets the fold SRG 54 and a −1 mode beam created when 40a(X) meets the fold SRG at substantially the same location; the beam labelled 42ab(X) is a superposition of a specular reflection beam created when 40a(X) meets the fold SRG 54 and a +1 mode beam created when 42b(X) meets the fold SRG at substantially the same location (and so on).

The exit SRG and incoupling SRG 52, 56 are oriented with a relative orientation angle A' (which is the angle between their respective grating lines). At each of the exit regions, the version meeting that region is diffracted so that, in addition to a zero order reflection mode beam propagating downwards in the direction $\phi'(X)$, $\pm\theta'(X)$, a first order (+1)

transmission mode beam 38(X) which propagates away from the optical component 10 in an outward direction $\phi_{out}(X)$, $\theta_{out}(X)$ given by:

$$\sin \theta_{out}(X) \sin(A' + \phi_{out}(X)) = n \sin \theta'(X) \sin(A' + \phi'(X)) \quad (6)$$

$$\sin \theta_{out}(X) \cos(A' + \phi_{out}(X)) = n \sin \theta'(X) \cos(A' + \phi'(X)) + \frac{\lambda}{d_3} \quad (7)$$

The output direction $\theta_{out}(X)$, $\phi_{out}(X)$ is that of the output beams outside of the waveguide (propagating in air). For a flat waveguide, equations (6), (7) hold both when the exit grating is on the front of the waveguide—in which case the output beams are first order transmission mode beams (as can be seen, equations (6), (7) correspond to the known transmission grating equations)—but also when the exit grating is on the rear of the waveguide (as in FIG. 7F)—in which case the output beams correspond to first order reflection mode beams which, upon initial reflection from the rear exit grating propagate in a direction $\theta'_{out}(X)$, $\phi'_{out}(X)$ within the optical component 10 given by:

$$n \sin \theta'_{out}(X) \sin(A' + \phi'_{out}(X)) = n \sin \theta'(X) \sin(A' + \phi'(X)) \quad (6')$$

$$n \sin \theta'_{out}(X) \cos(A' + \phi'_{out}(X)) = n \sin \theta'(X) \cos(A' + \phi'(X)) + \frac{\lambda}{d_3}; \quad (7')$$

these beams are then refracted at the front surface of the optical component, and thus exit the optical component in a direction $\theta_{in}(X)$, $\phi_{in}(X)$ given by Snell's law:

$$\sin \theta_{out}(X) = n \sin \theta'_{out}(X) \quad (8)$$

$$\phi'_{out}(X) = \phi_{out}(X) \quad (9)$$

As will be apparent, the conditions of equations (6), (7) follow straight forwardly from (6'), (7'), (8) and (9). Note that such refraction at the front surface, whilst not readily visible in FIG. 7F, will nonetheless occur in the arrangement of FIG. 7F.

It can be shown from the equations (2-7) that, when $$d = d_1 = d_3 \quad (10)$$

(that is, when the periods of the incoupling and exit SRGs 52, 56 substantially match);

$$d_2 = d/(2 \cos A); \quad (11)$$

and $$A' = 2A; \quad (12)$$

then $(\theta_{out}(X), \phi_{out}(X)) = (\theta_{in}(X), \phi_{in}(X))$.

Moreover, when the condition $$\sqrt{(1 + 8 \cos^2 A)} > \frac{nd}{\lambda} \quad (13)$$

is met, no modes besides the above-mentioned first order and zero order reflection modes are created by diffraction at the fold SRG 54. That is, no additional undesired beams are created in the fold zone when this criteria is met. The condition (13) is met for a large range of A, from about 0 to 70 degrees.

In other words, when these criteria are met, the exit SRG 56 effectively acts as an inverse to the incoupling SRG 52, reversing the effect of the incoupling SRG diffraction for each version of the beam with which it interacts, thereby outputting what is effectively a two-dimensionally expanded version of that beam 34(X) having an area substantially that of the exit SRG 56 (>>$D^2$ and which, as noted, is independent of the imaging optics 17) in the same direction as the original beam was inputted to the component 10 so that the outwardly diffracted beams form substantially the same virtual image as the inwardly inputted beams but which is perceivable over a much larger area.

In the example of FIG. 9B, A≈45° i.e. so that the fold and exit SRGs 54, 56 are oriented at substantially 45 and 90 degrees to the incoupling SRG 52 respectively, with the grating period of the fold region $d_2 = d/\sqrt{2}$. However, this is only an example and, in fact, the overall efficiency of the display system is typically increased when A≥50°.

Figure 7G:
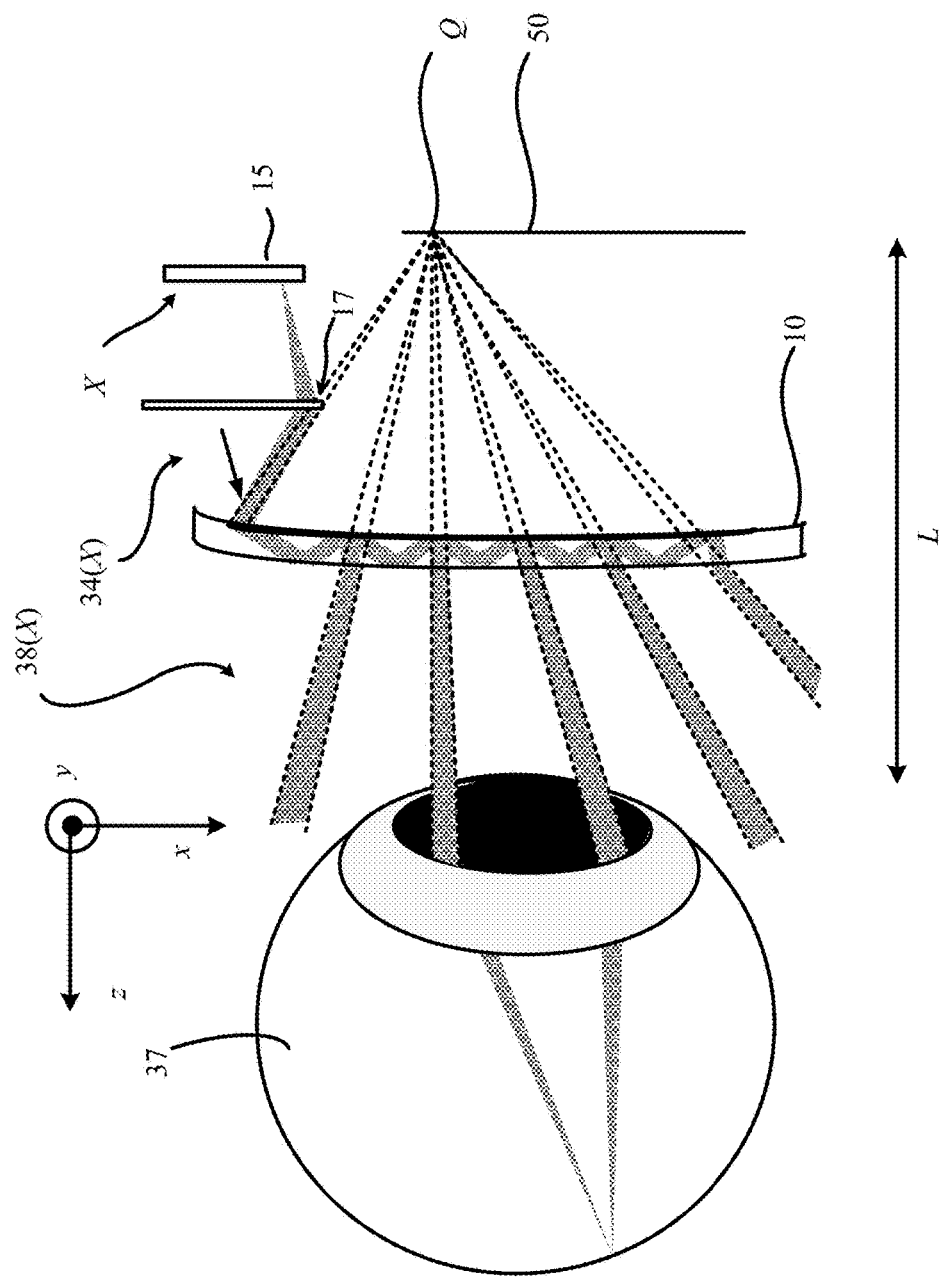
FIG. 7G is a plan view of a curved optical component.

The above considers flat optical components, but a suitably curved optical component (that is, having a radius of curvature extending substantially along the z direction) can be configured to function as an effective lens such that the output beams 30(X) are and are no longer as highly collimated and are not parallel, but have specific relative direction and angular separations such that each traces back to a common point of convergence—this is illustrated in FIG. 7G, in which the common point of convergence is labelled Q. Moreover, when every image point is considered, the various points of convergence for all the different active image points lie in substantially the same plane, labelled 50, located a distance L from the eye 37 so that the eye 37 can focus accordingly to perceive the whole image as if it were the distance L away. This can be equivalently stated as the various output beams forming substantially the same virtual version of the current display image as the corresponding input beams, but at the distance L from the eye 37 rather than at infinity. Curved optical components may be particularly suitable for short-sighted eyes unable to properly focus distant images.

Note, in general the "width" of the fold and exit zones does not have to be their horizontal extent—in general, the width of a fold or exit zone 14, 16 is that zone's extent in the general direction in which light is coupled into the fold zone 14 from the incoupling zone 12 (which is horizontal in the above examples, but more generally is a direction substantially perpendicular to the grating lines of the incoupling zone 12).

Note that the above arrangement of the light engine 13 is just an example. For example, an alternative light engine based on so-called scanning can provide a single beam, the orientation of which is fast modulated whilst simultaneously modulating its intensity and/or colour. As will be apparent, a virtual image can be simulated in this manner that is equivalent to a virtual image that would be created by collimating light of a (real) image on a display with collimating optics.

Making an optical component which includes SRGs typically involves the use of microfabrication techniques.

Microfabrication refers to the fabrication of desired structures of micrometer scales and smaller. Microfabrication may involve etching of and/or deposition on a substrate, to create the desired microstructure on the substrate.

Wet etching involves using a liquid etchant to selectively dislodge parts of a substrate e.g. parts of a film deposited on a surface of a plate and/or parts of the surface of the plate itself. The etchant reacts chemically with the substrate e.g. plate/film to remove parts of the substrate e.g. plate/film that are exposed to the etchant. The selective etching may be achieved by depositing a suitable protective layer on the substrate/film that exposes only parts of the substrate e.g. plate/film to the chemical effects of etchant and protects the remaining parts from the chemical effects of the etchant. The protective layer may be formed of a photoresist or other protective mask layer.

Dry etching involves selectively exposing a substrate e.g. plate/film (e.g. using a similar photoresist mask) to a bombardment of energetic particles to dislodge parts of the substrate e.g. plate/film that are exposed to the particles (sometimes referred to as "sputtering"). An example is ion beam etching in which parts are exposed to a beam of ions. Those exposed parts may be dislodged as a result of the ions chemically reacting with those parts to dislodge them (sometimes referred to as "chemical sputtering") and/or physically dislodging those parts due to their kinetic energy (sometimes referred to as "physical sputtering").

In contrast to etching, deposition—such as ion-beam deposition or immersion-based deposition—involves applying material to rather than removing material from a substrate e.g. plate/film. As used herein, the term "patterning a substrate's surface" or similar encompasses all such etching of/deposition on a plate or film, and such etching of/deposition on a plate or film is said to impose structure on the substrate's surface.

Conventional techniques for making an optical component involve, for instance, first coating a to-be patterned region of a master plate's surface (desired surface region) in a chromium layer or other protective mask layer (e.g. another metallic layer). The master plate and film constitute a substrate. The mask layer is covered in a positive photoresist. Positive photoresist means photoresist which becomes developable when exposed to light i.e. photoresist which has a composition such that those parts which have been exposed to light (and only those parts) are soluble in a developing fluid used to develop the photoresist following exposure. Light which forms a desired grating pattern (grating structure)—created, for instance, using two-beam laser interference to generate light which forms a grating structure in the form of an interference pattern—is then projected onto the photoresist so that only the photoresist at the locations of the light bands is exposed. The photoresist is then developed to remove the exposed parts, leaving selective parts of the mask layer visible (i.e. revealing only selective parts) and the remaining parts covered by the unexposed photoresist at the locations of the dark fringes. The uncovered parts of the mask layer are then be removed using conventional etching techniques e.g. an initial wet etching or ion beam etching process which removes the uncovered parts of the mask but not the parts covered by the photoresist, and which does not substantially affect the plate itself. Etching of the plate itself—such as further wet etching or further ion beam etching—is then performed, to transfer the pattern from the etched mask layer to the substrate itself.

Figure 12A:
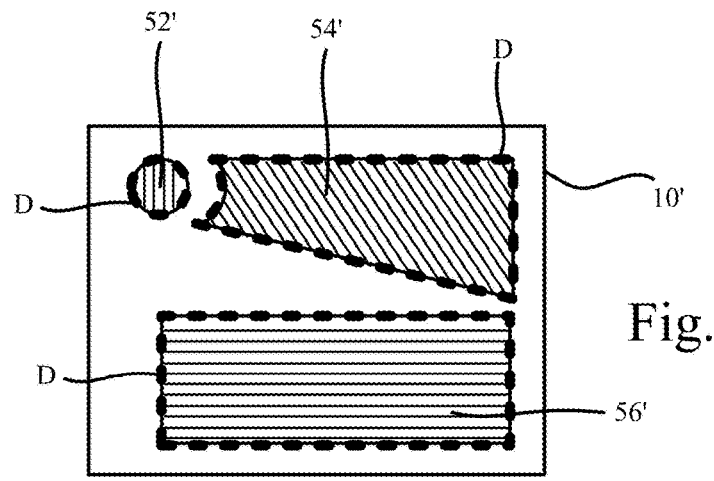
FIG. 12A shows an exemplary optical component having certain characteristics which may impact on image quality

FIG. 12A shows another optical component 10' which is similar in some respects to the optical component 10 of FIGS. 3A and 3B, but with some important differences that will now be discussed. As illustrated, the other optical component 10' has SRGs 52' (incoupling), 54' (fold), 56' (exit) similar to those of the optical component 10, with large gaps (>>100 μm) between them, including between the incoupling and fold SRGs 52', 54'. Because of this large spacing, in manufacturing the other optical component 10', the laser interference exposure could be done, using a positive photoresist technique along the lines of that outlined above, simply by applying shadow masks of different shapes in front of a master plate (substrate) during laser interference exposure.

Figure 12B:
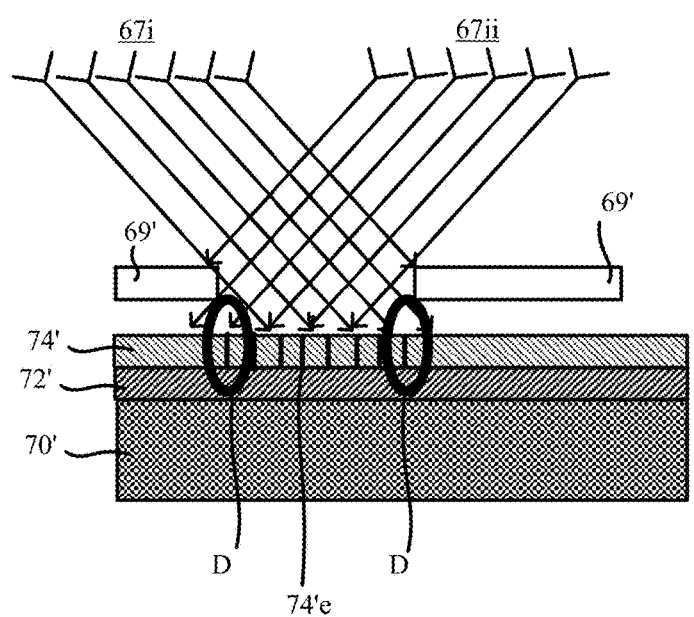
FIG. 12B shows an exposure set-up which could be used in making the optical component of FIG. 12A.

This is illustrated in FIG. 12B, which shows a master plate 70' from the side during a two-beam laser interference exposure process. The plate 70' is coated in a chromium layer 72', which is itself coated in photoresist 74', which is positive photoresist. The plate 70' and film 72' constitute a substrate. An interference pattern is created by the interference of two laser beams 67$i$, 67$ii$. A shadow mask 69' is used to prevent the pattern from falling outside of a desired portion (e.g. that spanned by incoupling SRG 52') of the substrate's surface so that the only photoresist which is exposed is the parts covering the desired portion on which light bands of the interference pattern fall (exposed photoresist is shown in black and labelled 74'$e$ in FIG. 12B). This can then be repeated for any other portions to be patterned (e.g. for those spanned by 54' and 56'). The positive photoresist can then be developed to remove the exposed parts 74'$e$, and the substrate patterned in the manner outlined above.

The shadow mask, however, causes distortion near the edges of the DOE areas. The distortion is due to light scattering, non-perfect contact of shadow mask and the finite thickness of the shadow mask (which effectively blurs the pattern near its edge). Herein, non-uniformity of a grating structure exhibited near its edges (of the type caused by such shadowing during fabrication, or similar) is referred to as "edge distortion". Edge distortion is indicated by the label D in FIG. 12B.

When the photoresist is developed, the edge distortion becomes embodied in the developed photoresist along with the grating structure, and as a result is transferred to the surface of the plate 70' when it comes to etching. As a result, the final optical component 10' (which either comprises or is manufactured from the patterned plate) also exhibits corresponding edge distortion as indicated by the dotted lines labelled D around the edges of the various DOE areas in FIG. 12A.

Moreover, as well as creating edge distortion, it is difficult to position the shadow mask 69' accurately when exposing the substrate in this manner, and therefore it would be difficult to reduce the size of the gaps between the SRGs 52', 54' without risking overlap between the SRGs 52', 54'.

Returning to FIG. 3B, in contrast to the other optical component 10' of FIG. 12A, the incoupling and fold zones 12, 14 of the optical component 10 are substantially contiguous in that they are separated by at most a narrow border zone 18 which has a width W as measured along (that is, perpendicular to) a common border 19 that divides the border zone 18. That is, the incoupling and fold zones are separated by a small distance W in width along a common border 18. Moreover, the incoupling, fold and exit SRGs 52, 54, 56 of the optical component 10 are free from edge distortion of the kind described above. It has been observed that this configuration produces superior image quality to that of the other optical component 10'.

Figure 10:
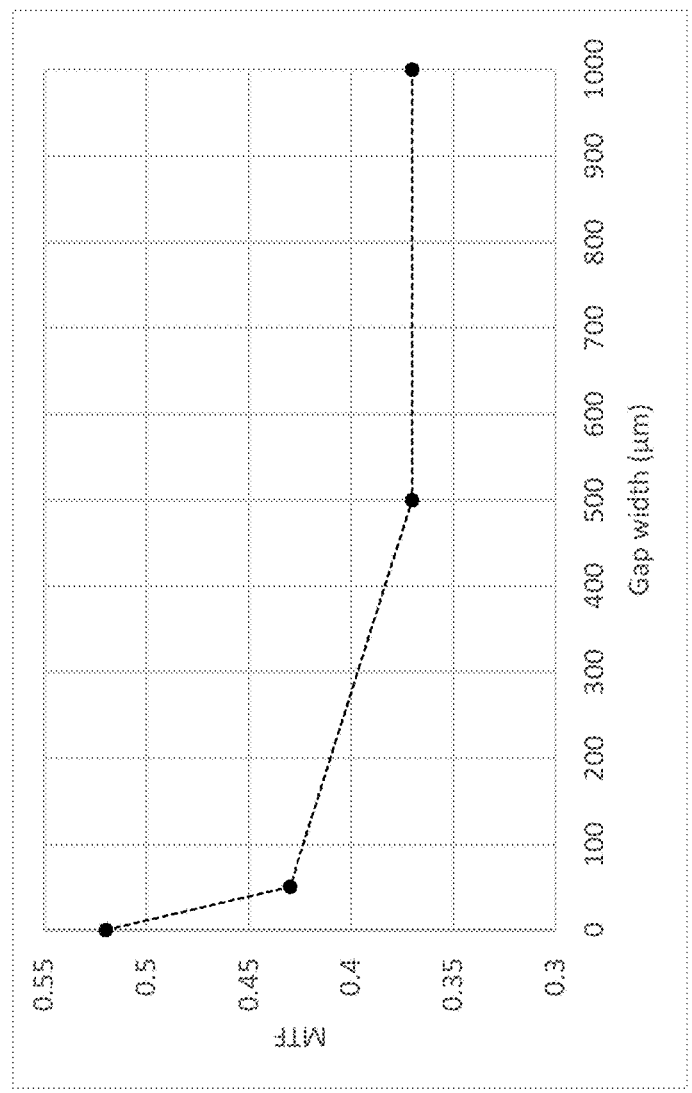
FIG. 10 shows a graph of MTF as function of gap width for an exemplary waveguide.

In particular, it has been observed that, when the separation W of the incoupling and fold regions 12, 14 along the common border 19 (the gap) is reduced to W≤$W_{max}$ along the length of the common border 19 (that is, provided the incoupling and fold zones are separated by no more than $W_{max}$ in width along the length of the common border 19)—where $W_{max}$≈100 μm (micrometers)—an improvement in image quality can be obtained. In practice, the size of gap at which the improvement is observed may have some dependence on the thickness of the waveguide. For example, for a waveguide having a thickness (extent in the z direction, as it is shown in the figures) of approximately 0.6 mm or less, a dramatic improvement in image quality is observed when $W_{max}$ is approximately 50 µm or less. This particular case is illustrated in FIG. 10, which shows curve of MTF (modular transfer function) drop as function of gap width in one case included for FIG. 10. The increase in MTF as the gap is reduced from 50 µm is immediately evident in FIG. 10. As is well known to persons skilled in the art, the modular transfer function (MTF) is a measure of the ability of an optical system to transfer various levels of detail from object to image. An MTF of 1.0 (or 100%) represents perfect contrast preservation, whereas values less than this mean that more and more contrast is being lost—until an MTF of 0 (or 0%), where line pairs (a line pair is a sequence of one black line and one white line) can no longer be distinguished at all. For a thicker waveguide—e.g. of thickness approximately 1 mm, an improvement is still expected for a gap size of up to 100 µm.

The common border 19 of FIG. 3B is arcuate (substantially semi-circular in this example), with the incoupling and fold regions 12, 14 having edges which are arcuate (in this case, substantially semi-circular) along the common border 19. The edge of incoupling region 12 is substantially circular overall.

The disclosure recognizes that conventional microfabrication techniques are ill suited to making the optical component 10 of FIG. 3B. In particular, existing techniques are ill-suited to making optical components exhibiting the requisite incoupling-fold zone separation $W=W_{max}$ and which are free of edge distortion whilst still accurately maintaining the desired angular orientation relationship between the various SRGs 52, 54, and 56 described above with reference to FIG. 9B.

A microfabrication process for making an optical component will now be described with reference to FIG. 11. As will become apparent in view of the following, the process of FIG. 11 can be used to make optical components of the type shown in FIG. 3B with the requisite small spacing between incoupling and fold zones, which are free from edge distortion, and which moreover exhibit the desired angular orientation to a high level of accuracy.

That is, this disclosure provides a novel interference lithographic method, which enables grating to be manufactured on the surface of an optical component that are spaced apart from one another by 100 micrometers or less. This is not achievable typically achievable with traditional interference lithographic methods.

Figure 11:
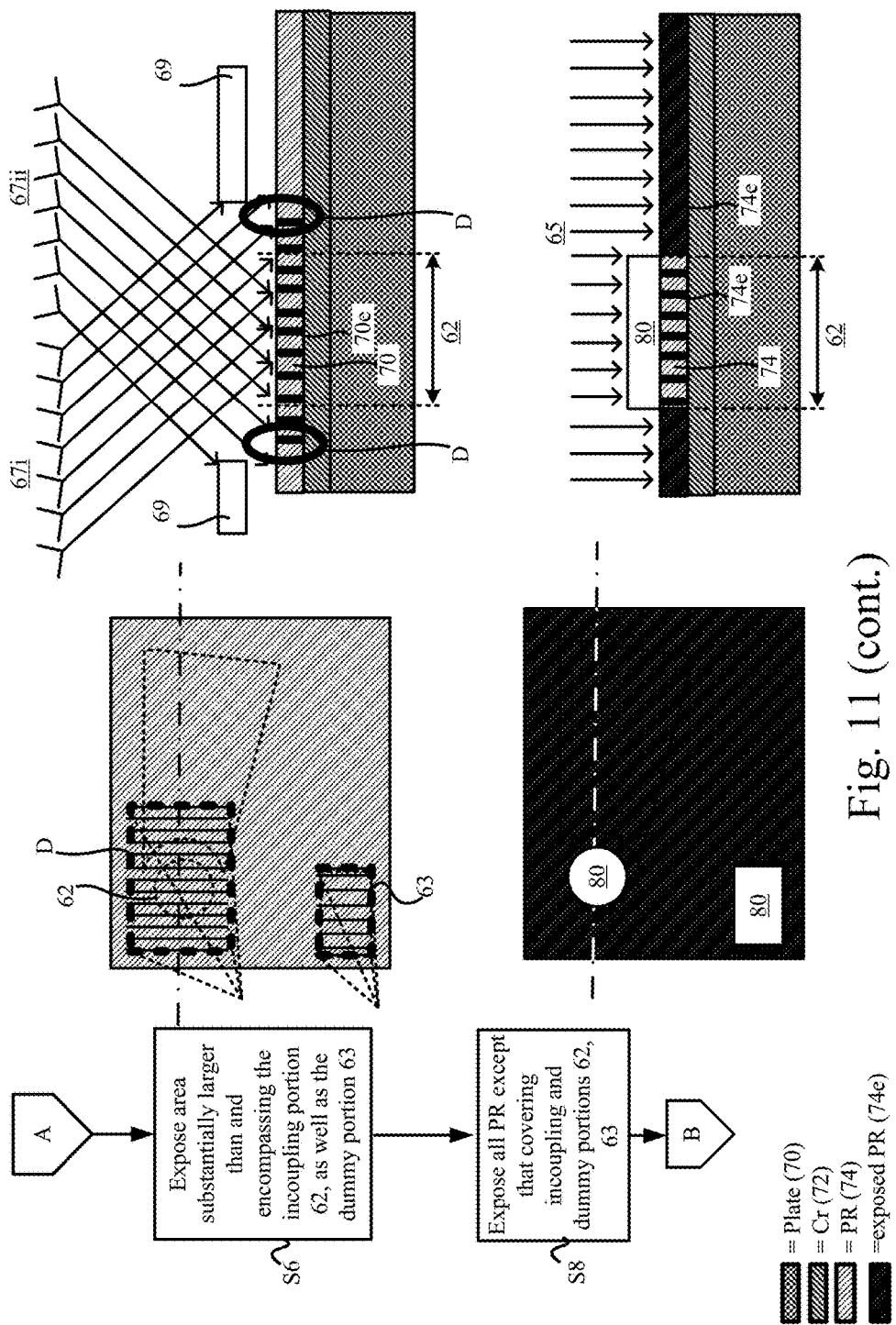
FIG. 11 shows a flow chart for a microfabrication process for manufacturing optical components or masters.
Figure 11:
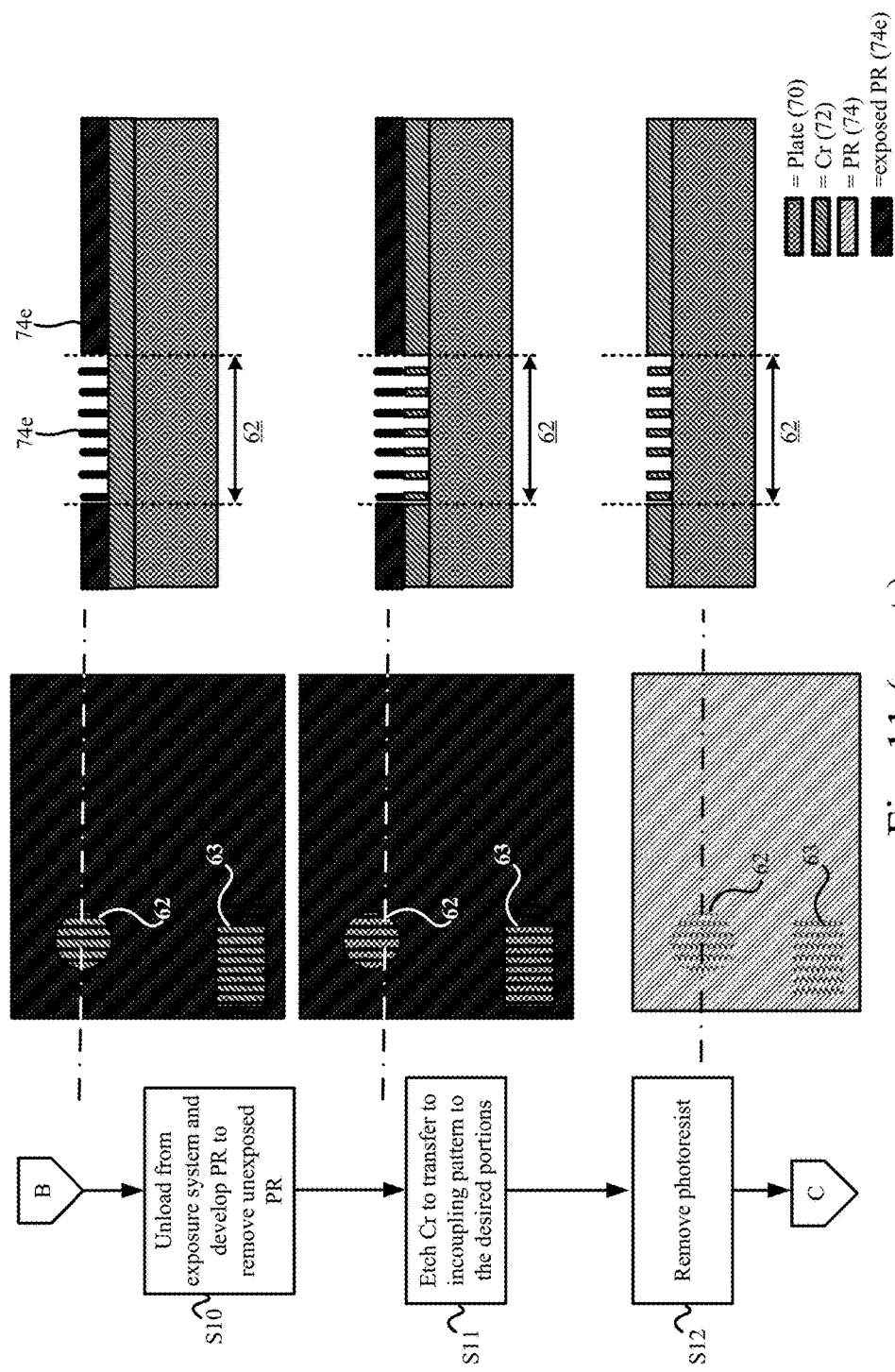
Figure 11:
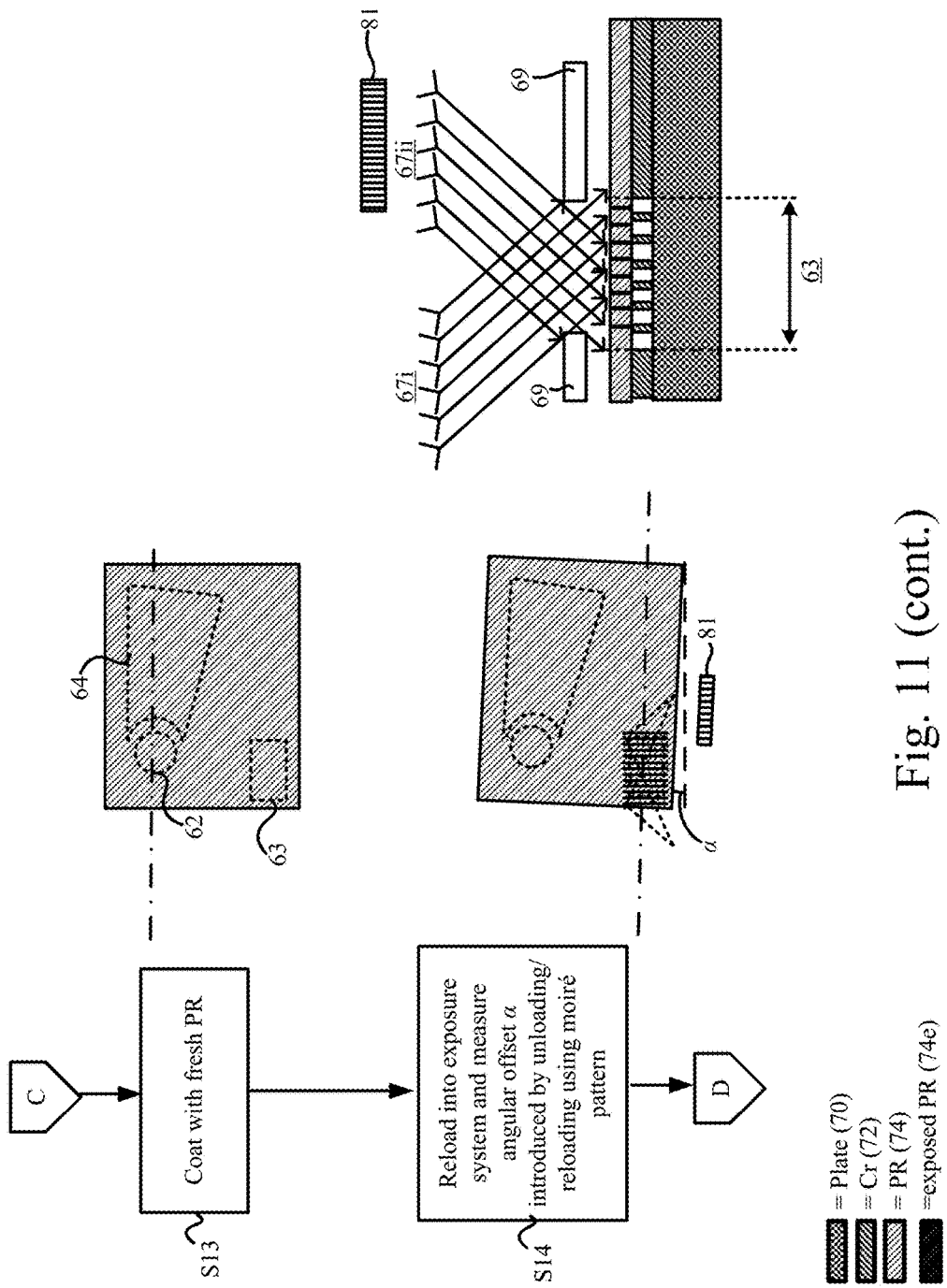
Figure 11:
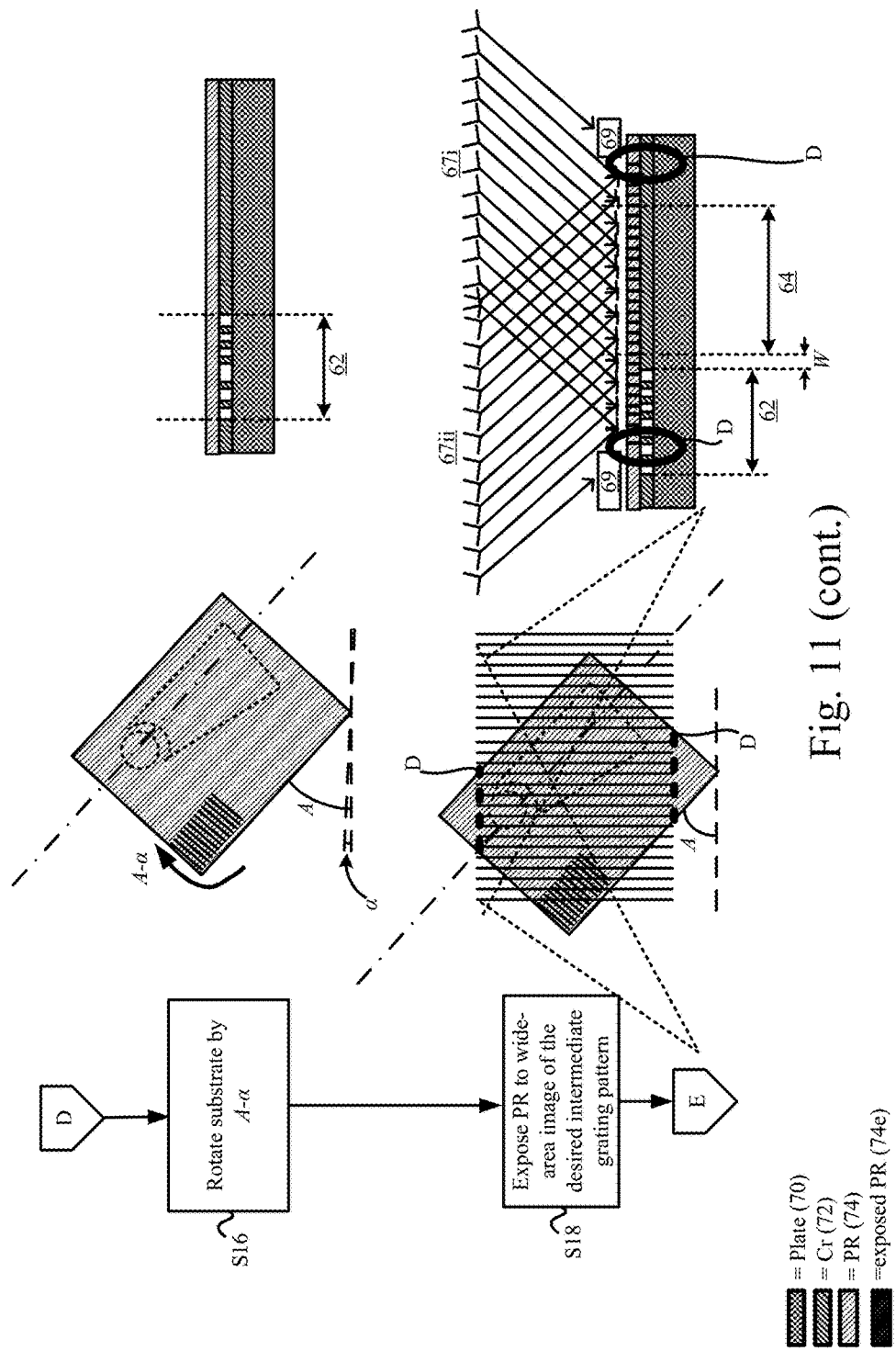
Figure 11:
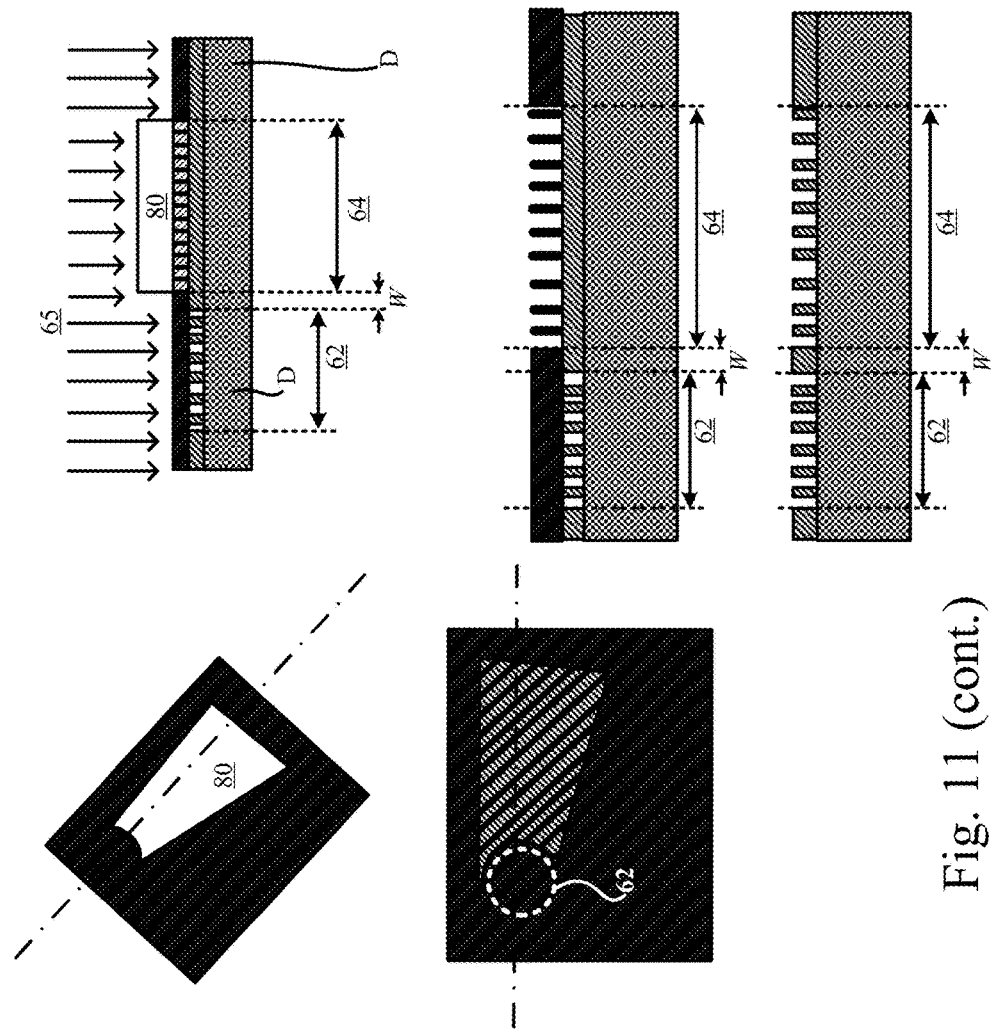

FIG. 11 shows on the left-hand side a flow chart for the process and on the right-hand side, for each step of the process, plan and/or side views of an exemplary master plate 70 as appropriate to illustrate the manner in which the plate 70 is manipulated at that step. Each side view is a cross-section taken along the dash-dotted line shown in the corresponding plan view.

An upper part of the plate's surface is coated with a chromium film 72. The plate 70 and film 72 constitute a substrate, a desired surface region of which (specifically, the surface region defined by the chromium layer 72 in this example), in performing the process, is selectively etched to create incoupling and fold SRGs 52, 54. The incoupling SRG 52 is fabricated on a first portion 62 of the desired surface region (incoupling portion), and the fold SRG 54 on a second distinct (i.e. non-overlapping) and substantially contiguous portion 64 of the desired surface region (fold portion) having the reduced separation $W \le W_{max}$ along the (intended) common border 19. For the optical component 10 shown in FIGS. 3A and 3B, the desired region corresponds to the rear of the component's surface from the perspective of the wearer.

The final etched substrate constitutes an optical component which may be incorporated in a display system (e.g. the display system 2 of FIG. 1), or which may be for use as a production master for manufacturing further optical components e.g. a mould for moulding such components from polymer (or indeed which may be used for making such moulds), in which case the SRGs 52, 54 as fabricated on the substrate's surface are transferred to (the rear of) those components by the manufacturing e.g. moulding process.

At step S4 of FIG. 11, the chromium layer 72 is coated in a negative photoresist film 74—that is, photoresist which becomes undevelopable when exposed to light i.e. photoresist which has a composition such that those parts which have been exposed to light (and only those parts) become substantially insoluble in a developing fluid used to develop the photoresist once exposed so that the exposed parts (and only the parts) remain post-development. This includes coating the incoupling portion 62 which is ultimately intended to be patterned with the incoupling SRG 52, as well as the fold portion 64 ultimately intended to be patterned with the fold SRG 54.

At step S6, an area substantially larger than and encompassing the incoupling portion 62 is exposed (shown in this example as a rectangle containing the desired circular area 62) to light which forms the desired incoupling grating structure (i.e. that of SRG 52). By directing two laser beams 67i, 67ii to coincide in an interference arrangement, an interference pattern which forms the desired incoupling grating structure, having a grating period d when incident on the photoresist 74, is created. The interference pattern comprises alternating light and dark bands, whereby only the parts of the photoresist on which the light bands fall are exposed (exposed photoresist is shown in black and labelled 70e in FIG. 11); however, in contrast to positive photoresist, it is these exposed parts 70e which become undevelopable whereas the non-exposed parts in the locations of the dark bands remain developable.

A shadow mask 69 is used to restrict the interference pattern to the larger area. The larger area is large enough not only to encompass the incoupling surface portion 62 but also such that all the edge distortion D created by the shadow mask lies outside of the incoupling portion 62 (in general, it is sufficient for the wider area to be such there is substantially no edge distortion in the vicinity of the intended common border 19, even if there is some edge distortion present elsewhere around the edge of the incoupling portion 62).

A dummy grating portion 63 is also exposed to the same (or a similar) interference pattern at the same time for reasons that will be discussed in due course.

The exposed portions 62, 63 can be practically of any shape or size but the excess exposure resulting from possible other exposures must not reach any "active part" of the desired exposure portions (i.e. in the illustration aside S6, other exposures must not overlap the circular incoupling portion 62).

As an alternative to using masks, the interference pattern could be projected over the whole of the desired surface region so that no shadowing effects are present on the desired surface region at all.

During the exposure step S6, the plate 70 is supported by a mechanical clamping or other fixing method in an laser interference exposure setup (exposure system) not shown in FIG. 11 to hold it steady relative to the exposure system (in particular, relative to the beams 67i, 67ii) whilst the exposure takes place. After step S6, the master plate 70 is unloaded from the laser interference exposure setup.

At step S8, the unloaded plate 70 is exposed to light 65 of substantially uniform intensity, but with photo mask 80 in place to expose photoresist and thus avoid photoresist development from areas outside the incoupling and dummy grating areas 62, 63. That is, photo mask 80 on the incoupling portion 62 and the dummy region 63 are used to prevent exposure of the portions 62, 63 to the uniform light 65. Thus, uniform light 65 is projected over the entirety of the desired surface region but for the incoupling and dummy portions (as these are covered by the photo mask 80) so that all of the photoresist other than that covering the incoupling and dummy portions 62, 63 becomes undevelopable throughout. It is thus the photo mask which define the portions 62, 63 (i.e. the portions 62, 63 have the same size and shape as the corresponding photomask 80 used to protect those portions), and not the shadow masks used in S6. A mask aligner is used to position the photo mask 80 accurately on correct position on the substrate. The mask aligner has components (e.g. ultraviolet-lamp, optics etc.) for generating uniform light for exposure and the mechanics for positioning the photomask 80 to the correct position.

As will be apparent, the only photoresist to retain any record of the grating structure(s) as projected at S6 is that which covers the incoupling and dummy portions—outside of those portions, all record of the grating structure(s) is intentionally destroyed. The entirely exposed photoresist outside of the incoupling and dummy portions 62, 63 includes all the parts of the photoresist that were subjected to the edge distortion D, thus completely removing any record of the edge distortion from the photoresist. Due to the nature of the process, there is virtually no distortion to the grating pattern.

At step S10, the photoresist is developed to embody the incoupling SRG grating structure by removing only those parts of that photoresist that have not been exposed to light using a developing fluid. All the exposed, undevelopable photoresist 74e is left substantially unchanged by the development of step S10. As illustrated in the figures to the right of S10 in FIG. 11, substantially no photoresist outside of the portions 62, 63 is removed in step S10; the only removed photoresist is lines of unexposed photoresist in the incoupling and dummy portions 62, 63 corresponding to the locations of the dark bands of the interference pattern as projected on the photoresist at S6.

At step S11, a chromium etching procedure is performed to etch the chromium layer 72 (but not the plate 70 itself) with the incoupling SRG pattern, such as dry etching of the chrome hard mask 72. In etching step S11, the photoresist serves as an etching mask to restrict etching of the chromium layer 72 to the incoupling and dummy grating surface portions only, whereby structure is imposed from the photoresist to the incoupling and dummy portions 62, 63. However, the exposed, undeveloped photoresist 74e outside of the portions 62, 63 inhibits etching outside of those portions 62, 63 so that no structure is imposed on the chromium 72 outside of those portions 9 (i.e. outside of those portions, the chromium is substantially unchanged).

Once the chromium 72 has been etched thus, the exposed photoresist 74e is removed (S12) and the chromium 72 recoated with fresh, unexposed negative photoresist 74 (S13).

As indicated above, the relative orientation angle between incoupling and fold SRGs is intended to be A as defined in equation (11) above and shown in FIG. 9B (with the incoupling and exit SRGs having a relative orientation angle 2A, as per equation (12)). This can be achieved by re-loading the plate 70 in the same exposure system (previously used at S6) supported again by the same mechanical clamps or other fixing method, and rotating the plate 70 by an amount that matches A relative to the exposure system so that any subsequently projected pattern is oriented to the original incoupling SRG pattern by A (S14). By using a suitable drive mechanism, it is possible to achieve highly accurate rotation of the plate 70.

However, due to inaccuracy of mechanical stoppers, the position of the plate 70 is not accurately the same as in step S6. This is illustrated in the plan view aside step S14 of FIG. 11, in which an angle α is shown to denote slight rotation relative to the plate's initial orientation at the previous exposure step S6 caused by unloading/reloading of the plate 70.

For this reason, prior to rotating the plate 70 at S14, the offset α between the plate position in S6 and S14 is first measured. The measurement is done using a fringe pattern 81. The fringe pattern 81 changes when the plate is rotated and this can be used to measure the angle of the plate with better than 0.001 degrees resolution.

To create the fringe pattern 81, the dummy grating portion is re-exposed to the same interference pattern it was exposed to at step S6 (or at least an interference pattern having the same angular orientation), as shown on the right-hand side of FIG. 11. The fringe pattern is evident notwithstanding the presence of the photoresist atop the dummy grating. The fringe pattern is created as a result of the interaction between the interference pattern and the dummy grating, and when the angular alignment is better than e.g. 0.01 degrees, has a fringe spacing—typically of the order of few mm—and thus clearly visible when the offset α is about 5 thousandths of a degree, and which increases as a is reduced towards zero, becoming maximal (effectively infinite) upon a reaching zero. The fringe spacing is determined by the offset α and, conversely, can be used to measure a.

This leaves the photoresist atop the dummy grating partially exposed; as will become apparent, this is inconsequential. Notably, the dummy grating portion 63 is sufficiently offset from the fold grating portion 64 for the photoresist atop the fold grating portion to remain unexposed in creating the fringe pattern 81.

Once α has been measured, at step S16 the plate 70 is rotated from that initial orientation by an amount=A−α (thereby accounting for α in the rotation) so that the plate 70 now has an orientation A relative to its initial position at S6 to a high level of accuracy.

At step S18, an area substantially larger than and encompassing the fold portion 64 is exposed (shown in this example as a rectangle containing the desired area 64) again by directing two laser beams 67i, 67ii to coincide in an interference arrangement, leaving the parts of the photoresist on which light bands fall undevelopable in a manner equivalent to S6 (but without any additional dummy grating area being exposed). In S18, the interference pattern has a period $d/(2 \cos A)$ when incident on the photoresist. A shadow mask 69 is again used to restrict the interference pattern to this area, which is large enough not only to encompass the fold surface portion 64 but also such that all the edge distortion D created by the shadow mask lies outside of the incoupling portion 62 (or at least clear of the common border 16).

Some or all of the photoresist atop the incoupling grating will likely be exposed at S18, which is inconsequential as it has no effect on the incoupling pattern which has already been etched into the underlying chromium 72.

All other areas except fold portion 64 are then exposed (S19) to uniform light 65 with a suitable photo mask 80 in place to prevent exposure of the fold portion 64 (and only that portion) in a manner equivalent to step S8. This leaves all the photoresist covering the incoupling portion 62 (and also that covering an exit portion ultimately intended to be etched to form the exit grating 56) exposed and therefore undevelopable. The photoresist is then developed to remove only the unexposed parts (S20) in a manner equivalent to step S10, the chromium one again etched to transfer the fold SRG pattern from the photoresist to the chromium, and the photoresist removed following etching (equivalent to S11-S12). The incoupling portion is protected by the exposed and therefore undeveloped photoresist 70e, thereby preserving the incoupling grating pattern already etched into the chromium.

The use of photo mask 80 to define the incoupling and fold portions enables the location of the DOE areas to be controlled far more accurately then when simply using shadow masks to define those areas (as in the positive photoresist technique outlined above). It thus becomes possible to reduce the separation of those portions to $W \leq W_{max}$ whilst still retaining separation of those portions (i.e. without the etched patterns overlapping).

Although not shown explicitly in FIG. 11, it will be apparent that the chromium covering the grating area ultimately intended for the exit SRG 56 (vertically below the incoupling and fold SRGs 52, 54) is unaffected by the etching of both S11 and S22 as in both of those steps it is protected by undeveloped photoresist.

A similar process could be repeated to etch the desired fold grating structure into the chromium, again using a fringe pattern to achieve a highly accurate angular orientation of 2 A between the incoupling and exit grating structures. The exit grating in the present configuration is relatively far away from the input grating. Thus input grating and exit grating can be exposed to the same photoresist layer with large enough shadow masks to avoid edge distortions.

Once all three structures have been etched into the chromium, the plate 70 itself is subject to an etching procedure (e.g. ion-beam etching) in which the chromium now serves as an etching mask, whereby the grating structures are transferred from the etched chromium 72 to the plate 70 itself to form the desired incoupling, exit and fold SRGs 52, 54, 56 on the plate itself with very good angular accuracy, narrow gap $W \leq W_{max}$ between SRgs 52, 54, and good quality edges free form edge distortion.

Note that the dummy grating pattern is not etched onto the plate itself as it is not desired on the final optical component.

Once the plate itself has been etched, the chromium is removed and the plate 70, can e.g. be used in a display system of the kind shown in FIG. 1, to mould further optical components, or indeed to make such moulds.

It has been demonstrated that, using the process of FIG. 11, substrates can be patterned, free from edge distortion, with the actual relative orientation angle between the incoupling and fold zones 14, 16 consistently being $\arccos(d_1/(2d_2))$ (see equations 11, 12 above) and/or one half of the relative orientation angle between the incoupling and exit SRGs 12, 16 (see equation 13, above) to within ±one thousandth of a degree (as measured from a representative statistical population of substrates fabricated using the present techniques). However two thousandths of a degree may be still acceptable angular error in some practical contexts.

Whilst the above uses a dummy grating for re-alignment, it is possible in other embodiments to use the exit grating for re-alignment. The input and exit grating are in practice done without taking the plate out of the sample holder in laser system because they are ~one centimeter apart and thus enable easy shadowing with standard mask. The exit grating is relatively large and thus a fraction of it (which is far enough away from fold grating) could be used for re-alignment when the plate is inserted back in the laser system for fold grating interference exposure.

Whilst in the above an intermediate metallic layer is deposited between the master plate and the substrate, a photoresist layer may alternatively be applied to the substrate directly and selective regions of the photoresist so that the photo resist functions in a similar manner to the aforementioned mask. However, using a separate metallic mask layer can facilitate better selectivity of etching.

Note that, whilst the process of FIG. 11 is described with reference to etching, the techniques can be adapted to effect patterning by way of deposition instead in a manner that will be apparent.

According to a first aspect, a display system comprising an optical waveguide and a light engine is provided. The optical waveguide has an incoupling grating, an intermediate grating and an exit grating. The light engine is configured to generate multiple input beams. Each beam is substantially collimated and directed to the incoupling grating in a unique inward direction, whereby the multiple input beams form a virtual image. The intermediate and exit grating have widths substantially larger than the beams' diameters. The incoupling grating is arranged to couple each beam into the intermediate grating, in which that beam is guided onto multiple splitting regions of the intermediate grating in a direction along the width of the intermediate grating. The intermediate grating is arranged to split that beam at the splitting regions to provide multiple substantially parallel versions of that beam. Those multiple versions are coupled into the exit grating, in which the multiple versions are guided onto multiple exit regions of the exit grating. The exit regions lie in a direction along the width of the exit grating. The exit grating is arranged to diffract the multiple versions of that beam outwardly. The multiple input beams thus cause multiple exit beams to exit the waveguide which form a version of the virtual image. The incoupling and intermediate gratings are substantially contiguous, separated by no more than 100 micrometers (and optionally no more than 50 micrometers) in width along a common border.

According to a second aspect, an optical waveguide for a display system which has an incoupling grating, an intermediate grating and an exit grating is provided. The incoupling grating is arranged to receive multiple input beams, each beam being substantially collimated and directed to the incoupling grating in a unique inward direction, whereby the multiple input beams form a virtual image. The intermediate and exit grating have widths substantially larger than the beams' diameters. The incoupling grating is arranged to couple each beam into the intermediate grating, in which that beam is guided onto multiple splitting regions of the intermediate grating in a direction along the width of the intermediate grating. The intermediate grating is arranged to split that beam at the splitting regions to provide multiple substantially parallel versions of that beam which are coupled into the exit grating, in which the multiple versions are guided onto multiple exit regions of the exit grating, the exit regions lying in a direction along the width of the exit grating. The exit grating is arranged to diffract the multiple versions of that beam outwardly, the multiple input beams thus causing multiple exit beams to exit the waveguide which form a version of the virtual image. The incoupling and intermediate gratings are substantially contiguous, being separated by no more than 100 (and optionally no more than 50 micrometers) micrometers in width along a common border.

In embodiments, the incoupling and intermediate gratings may exhibit substantially no edge distortion at least in the vicinity of the common border.

The incoupling and intermediate gratings may have a relative orientation angle that is one half that between the incoupling and exit gratings to within two thousandths of a degree, and possibly to within one thousandth of a degree.

The incoupling grating may have a grating period $d_1$, the intermediate grating may have a grating period $d_2$, and the incoupling and intermediate gratings may have a relative orientation angle that is $\arccos(d_1/(2d_2))$ to within two thousandths of a degree, and possibly to within one thousandth of a degree.

The common border may be arcuate, the incoupling and intermediate gratings having edges that are arcuate along the common border. For instance, the common border may substantially semi-circular, the edges of the incoupling and intermediate gratings being substantially semi-circular along the common border. For instance, the edge of the incoupling grating may be substantially circular.

The intermediate grating may have a height that increases in a direction along its width and away from the incoupling grating.

The display system of the first aspect may be wearable by a user. For example, the display system may be embodied in a wearable headset, the exit grating positioned forward of an eye of the user when worn to make the image visible to the user.

The display system may comprise two such optical waveguides, each of which provides image light to a different eye of the user.

According to a third aspect a microfabrication process for making an optical component comprises a patterning stage in which one or more portions of a substrate's surface are patterned by performing at least the following steps. At least a region of the substrate's surface is coated in negative photoresist, the region encompassing said portions. The negative photoresist becomes undevelopable when exposed to light. Light which forms a grating structure is projected over each of the portions. Light of substantially uniform intensity is projected over the entirety of the region but for the portions, thereby leaving the negative photoresist outside of the portions undevelopable. The negative photoresist is developed so as to embody the grating structure in the photoresist covering the portions. The substrate's surface is patterned to impose the grating structure on the substrate's surface from the developed photoresist; the undevelopable photoresist inhibits patterning of the surface region outside of the portions. The optical component comprises the patterned substrate.

In embodiments the microfabrication process may comprise a first such patterning stage followed by a second such patterning stage, wherein a second grating structure imposed on the substrate's surface at the second stage is offset from a first grating structure imposed on the substrate's surface at the first stage by a non-zero angle.

The projecting steps of the first stage may be performed with the substrate supported in a first orientation in an exposure system, and the second stage may comprise: prior to the projecting steps of the second stage, rotating the substrate relative to the exposure system to a second orientation before performing the projecting steps of the second stage, wherein the second orientation is offset from the first orientation by said non-zero angle.

The substrate may be removed from the exposure system following the projecting steps of the first stage and re-loaded in the exposure system prior to performing the projecting steps of the second stage, and the second stage may comprise: after re-loading the substrate but before rotating the substrate to the second orientation, creating a fringe pattern by projecting light which forms a grating structure onto a portion of the substrate's surface already patterned at the first stage, wherein the fringe pattern is used when rotating the substrate to the second orientation to account for any unintended rotation of the substrate away from the first orientation caused by removing and re-loading the substrate.

The first grating structure may have a period different from the second grating structure.

A first portion may be patterned at the first stage with the first grating structure and a second portion patterned at the second stage with the second grating structure have a common border, wherein at the first stage a first shadow mask is used to restrict light which forms the first grating structure to a first area larger than and encompassing that first portion, wherein at the second stage a second shadow mask is used to restrict light which forms the second grating structure onto a second area larger than and encompassing that second portion, and wherein the first and second areas are large enough that those first and second portions are free from edge distortion created by the first and second mask respectively at least in the vicinity of the common border.

The first and second portions may be separated by no more than 50 micrometers in width along the common border.

For at least one of the portions, a shadow mask may be used in the first projecting step to restrict the light which forms a grating structure to an area larger than and encompassing that portion, the area sufficiently large for that portion to be entirely free from edge distortion created by the mask.

The substrate may initially comprises a master plate on which a metallic film is deposited, wherein the metallic film is patterned in the patterning step of the third aspect to impose the grating structure on the metallic film from the photoresist.

The process may comprise patterning the plate to impose the grating structure on the plate from the metallic film, and subsequently removing the metallic film, wherein the optical component comprises the patterned plate with the metallic film removed.

The common border may be arcuate. For example, one of said first and second portions may be substantially circular.

One of said first and second portions may have a height that increases in a direction along its width and away from the other of said first and second portions.

An optical component, made according to any manufacturing process disclosed herein, may itself be used to make at least one further optical component. The further optical component may for instance be moulded from polymer using the optical component.

The further optical component may be for use in a display system.

A fourth aspect provides a product made by any of the manufacturing processes disclosed herein.

The further optical component may be used to make at least one yet further optical component. The yet further optical component may for instance be moulded from polymer using the further optical component.

According to a fifth aspect an optical component has a first and a second diffraction grating, the first grating formed by a first series of substantially parallel, elongate grooves in a first portion of the optical component's surface, the second grating formed by a second series of substantially parallel, elongate grooves in a second portion of the optical component's surface distinct from the first portion. The second grating is offset from the first grating by a non-zero angle. The first and second portions are substantially contiguous, separated by no more than 100 micrometers (optionally 50 micrometers) in width along a common border. The first and second gratings exhibit substantially no edge distortion at least in the vicinity of the common border.

A display system comprising a display, an optical waveguide and collimating optics is provided. An image is generated on the display. The optical waveguide has an incoupling grating, an intermediate grating and an exit grating. The collimating optics is arranged to substantially collimate the image into multiple input beams. Each beam is formed by collimating light from a respective image point, that beam directed to the incoupling grating in a unique inward direction which depends on the location of that point in the image. The multiple input beams thus forming a virtual version of the image. The intermediate and exit grating have widths substantially larger than the beams' diameters. The incoupling grating is arranged to couple each beam into the intermediate grating, in which that beam is guided onto multiple splitting regions of the intermediate grating in a direction along the width of the intermediate grating. The intermediate grating is arranged to split that beam at the splitting regions to provide multiple substantially parallel versions of that beam. Those multiple versions are coupled into the exit grating, in which the multiple versions are guided onto multiple exit regions of the exit grating. The exit regions lie in a direction along the width of the exit grating. The exit grating is arranged to diffract the multiple versions of that beam outwardly, substantially in parallel and in an outward direction which substantially matches the unique inward direction in which that beam was incoupled. The multiple input beams thus cause multiple exit beams to exit the waveguide which form substantially the same virtual version of the image. The incoupling and intermediate gratings are substantially contiguous, separated by no more than 100 micrometers (and optionally no more than 50 micrometers) in width along a common border.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A microfabrication process for making an optical component, the process comprising a patterning stage in which one or more first portions of a substrate's surface are patterned by at least:
    coating at least a region of the substrate's surface in negative photoresist, said region encompassing said first portions, whereby the negative photoresist becomes undevelopable when exposed to light;
    projecting light which forms a first grating structure over each of said first portions;
    projecting light of substantially uniform intensity over the entirety of said region but for said first portions, thereby leaving the negative photoresist outside of said first portions undevelopable;
    developing the negative photoresist so as to embody the grating structure in the photoresist covering said first portions;
    patterning the substrate's surface to impose the grating structure on the substrate's surface from the developed photoresist, the undevelopable photoresist inhibiting patterning of the surface region outside of said first portions, wherein the optical component comprises the patterned substrate; and
    following a first such patterning stage that forms the first grating structure with a second such patterning stage that patterns one or more second portions to form a second grating structure, the first grating structure and the second grating structure being separated by 50 to 100 micrometers along an entire common arcuate border between the first grating structure and the second grating structure.

2. A microfabrication process according to claim 1, wherein the second grating structure imposed on the substrate's surface at the second stage is offset from the first grating structure imposed on the substrate's surface at the first stage by a non-zero angle.

3. A microfabrication process according to claim 2, wherein the projecting steps of the first stage are performed with the substrate supported in a first orientation in an exposure system, and wherein the second stage comprises:
    prior to the projecting steps of the second stage, rotating the substrate relative to the exposure system to a second orientation before performing the projecting steps of the second stage, wherein the second orientation is offset from the first orientation by said non-zero angle.

4. A microfabrication process according to claim 3 wherein the substrate is removed from the exposure system following the projecting steps of the first stage and re-loaded in the exposure system prior to performing the projecting steps of the second stage, wherein the second stage comprises:
    after re-loading the substrate but before rotating the substrate to the second orientation, creating a fringe pattern by projecting light which forms a grating structure onto a portion of the substrate's surface already patterned at the first stage, wherein the fringe pattern is used when rotating the substrate to the second orientation to account for any unintended rotation of the substrate away from the first orientation caused by removing and re-loading the substrate.

5. A microfabrication process according to claim 2 wherein the first grating structure has a period different from the second grating structure.

6. A microfabrication process according to claim 2 wherein at the first stage a first shadow mask is used to restrict light which forms the first grating structure to a first area larger than and encompassing that first portion, wherein at the second stage a second shadow mask is used to restrict light which forms the second grating structure onto a second area larger than and encompassing that second portion, and wherein the first and second areas are large enough that those first and second portions are free from edge distortion created by the first and second mask respectively at least in the vicinity of the common border.

7. A microfabrication process according to claim 1, wherein, for at least one of said first portions, a shadow mask is used in the first projecting step to restrict the light which forms the first grating structure to an area larger than and encompassing that portion, the area sufficiently large for that portion to be entirely free from edge distortion created by the mask.

8. A microfabrication process according to claim 1, wherein the substrate initially comprises a master plate on which a metallic film is deposited, wherein the metallic film is patterned in the patterning step of claim 1 to impose the first and second grating structures on the metallic film from the photoresist.

9. A microfabrication process according to claim 8, comprising patterning the plate to impose the first and second grating structures on the plate from the metallic film, and subsequently removing the metallic film, wherein the optical component comprises the patterned plate with the metallic film removed.

10. A microfabrication process according to claim 1 wherein one of said first and second grating structures is substantially circular.

11. A microfabrication process according to claim 1 wherein one of said first and second grating structures has a height that increases in a direction along its width and away from the other of said first and second grating structures.

12. A microfabrication process according to claim 1 wherein the projecting the light of substantially uniform intensity removes a record of edge distortion including non-uniformity of the first grating structure outside said first portions.

13. A microfabrication process according to claim 1 wherein first grating structure and the second grating structure are separated along the entire common arcuate border by a constant width.

14. A microfabrication process according to claim 1 wherein the first grating structure and the second grating structure are separated along the entire common arcuate border by 50 micrometers when the patterned substrate thickness is 0.6 millimeters and by 100 micrometers when the patterned substrate thickness is 1 millimeter.

15. A manufacturing process comprising using an optical component to make at least one further optical component, the optical component made using a microfabrication process comprising a patterning stage in which one or more first portions of a substrate's surface are patterned by at least:
  coating at least a region of the substrate's surface in negative photoresist, said region encompassing said first portions, whereby the negative photoresist becomes undevelopable when exposed to light;
  projecting light which forms a first grating structure over each of said first portions;
  projecting light of substantially uniform intensity over the entirety of said region but for said first portions, thereby leaving the negative photoresist outside of said first portions undevelopable;
  developing the negative photoresist so as to embody the first grating structure in the photoresist covering said first portions;
  patterning the substrate's surface to impose the first grating structure on the substrate's surface from the developed photoresist, the undevelopable photoresist inhibiting patterning of the surface region outside of said first portions, wherein the optical component comprises the patterned substrate; and
  following a first such patterning stage that forms the first grating structure with a second such patterning stage that patterns one or more second portions to form a second grating structure, the first grating structure and the second grating structure being separated by 50 to 100 micrometers along an entire common arcuate border between the first grating structure and the second grating structure.

16. A manufacturing process according to claim 15 wherein the further optical component is moulded from polymer using the optical component and/or the further optical component is for use in a display system.

17. A manufacturing process according to claim 15 comprising using the further optical component to make at least one yet further optical component.

18. A manufacturing process according to claim 17 wherein the yet further optical component is moulded from polymer using the further optical component.

19. A manufacturing process according to claim 15 wherein the first grating structure and the second grating structure are separated along the entire common arcuate border by a constant width.

20. A manufacturing process according to claim 15 wherein the first grating structure and the second grating structure are separated along the entire common arcuate border by 50 micrometers when the patterned substrate thickness is 0.6 millimeters and by 100 micrometers when the patterned substrate thickness is 1 millimeter.

* * * * *